United States Patent
Blomgren et al.

(10) Patent No.: US 12,263,163 B2
(45) Date of Patent: Apr. 1, 2025

(54) CRYSTALLINE SUCCINATE SALT OF 6-(6-AMINOPYRAZIN-2-YL)-N-(4-(4-(OXETAN-3-YL)PIPERAZIN-1-YL) PHENYL)IMIDAZO[1,2-A]PYRAZIN-8-AMINE AS A SYK INHIBITOR

(71) Applicant: Kronos Bio, Inc., San Mateo, CA (US)

(72) Inventors: Peter A. Blomgren, Issaquah, WA (US); Kevin S. Currie, North Bend, WA (US); Jeffrey E. Kropf, Issaquah, WA (US); Seung H. Lee, Sammamish, WA (US); Jennifer R. Lo, Seattle, WA (US); Scott A. Mitchell, Kenmore, WA (US); Aaron C. Schmitt, Hamden, CT (US); Jin-Ming Xiong, Bel Air, MD (US); Jianjun Xu, Bellevue, WA (US); Sundaramoorthi Swaminathan, Burlingame, CA (US); Zhongdong Zhao, Bellevue, WA (US)

(73) Assignee: Kronos Bio, Inc., San Mateo, CA (US)

( * ) Notice: Subject to any disclaimer, the term of this patent is extended or adjusted under 35 U.S.C. 154(b) by 0 days.

(21) Appl. No.: 18/057,195

(22) Filed: Nov. 18, 2022

(65) Prior Publication Data

US 2023/0158023 A1 May 25, 2023

Related U.S. Application Data

(60) Continuation of application No. 17/082,595, filed on Oct. 28, 2020, now Pat. No. 11,517,570, which is a division of application No. 16/413,458, filed on May 15, 2019, now Pat. No. 10,828,299, which is a continuation of application No. 15/945,685, filed on Apr. 4, 2018, now Pat. No. 10,342,794, which is a continuation of application No. 14/578,973, filed on Dec. 22, 2014, now Pat. No. 9,290,505.

(60) Provisional application No. 61/920,407, filed on Dec. 23, 2013.

(51) Int. Cl.
*A61K 31/4985* (2006.01)
*A61K 9/00* (2006.01)
*A61K 31/5377* (2006.01)
*C07D 487/04* (2006.01)

(52) U.S. Cl.
CPC ........ *A61K 31/4985* (2013.01); *A61K 9/0053* (2013.01); *A61K 31/5377* (2013.01); *C07D 487/04* (2013.01)

(58) Field of Classification Search
CPC ............. A61K 31/4985; C07D 487/04
USPC ................. 514/249; 544/117, 350, 359, 405
See application file for complete search history.

(56) References Cited

U.S. PATENT DOCUMENTS

| | | |
|---|---|---|
| 5,593,997 A | 1/1997 | Dow et al. |
| 5,658,857 A | 8/1997 | Andree et al. |
| 5,783,576 A | 7/1998 | Roos et al. |
| 5,846,514 A | 12/1998 | Foster et al. |
| 6,334,997 B1 | 1/2002 | Foster et al. |
| 6,911,443 B2 | 6/2005 | Yura et al. |
| 6,919,340 B2 | 7/2005 | Currie et al. |
| 6,919,341 B2 | 7/2005 | Paruch et al. |
| 7,160,885 B2 | 1/2007 | Currie et al. |
| 7,189,723 B2 | 3/2007 | Mitchell et al. |
| 7,259,164 B2 | 8/2007 | Mitchell et al. |
| 7,312,341 B2 | 12/2007 | Desimone et al. |
| 7,405,295 B2 | 7/2008 | Currie et al. |
| 8,354,526 B2 | 1/2013 | Ding et al. |
| 8,440,667 B2 | 5/2013 | Mitchell et al. |
| 8,450,321 B2 | 5/2013 | Mitchell et al. |

(Continued)

FOREIGN PATENT DOCUMENTS

| | | |
|---|---|---|
| CA | 2175837 | 5/1995 |
| CN | 101124227 | 2/2008 |

(Continued)

OTHER PUBLICATIONS

Abrisqueta et al., Personalizing treatment for chronic lymphocytic leukemia, Expert Review of Hematology, 2011, 4(1):27-35.

(Continued)

*Primary Examiner* — Douglas M Willis
(74) *Attorney, Agent, or Firm* — Knobbe, Martens, Olson & Bear, LLP

(57) ABSTRACT

The present disclosure relates to compounds that are Syk inhibitors or pharmaceutically acceptable salts or co-crystals thereof, and pharmaceutical compositions thereof, and to their use in the treatment of various disease states, including cancer and inflammatory conditions. In particular embodiments, a Syk inhibitor is a crystalline monomesylate salt of 6-(6-aminopyrazin-2-yl)-N-(4-(4-(oxetan-3-yl)piperazin-1-yl)phenyl)imidazo-[1,2-a]pyrazin-8-amine of formula 2:

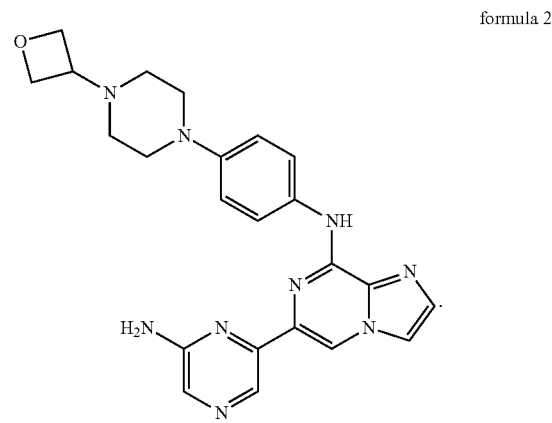

formula 2

19 Claims, 16 Drawing Sheets

(56) References Cited

U.S. PATENT DOCUMENTS

| | | |
|---|---|---|
| 8,455,493 B2 | 6/2013 | Mitchell et al. |
| 8,546,370 B2 | 10/2013 | Okram et al. |
| 8,697,699 B2 | 4/2014 | Mitchell et al. |
| 8,748,607 B2 | 6/2014 | Mitchell et al. |
| 8,765,761 B2 | 7/2014 | Mitchell et al. |
| 8,796,270 B2 | 8/2014 | Mitchell |
| 8,962,835 B2 | 2/2015 | Mitchell et al. |
| 9,120,811 B2 | 9/2015 | Mitchell et al. |
| 9,212,191 B2 | 12/2015 | Mitchell et al. |
| 9,290,505 B2 | 3/2016 | Blomgren et al. |
| 9,376,441 B2 | 6/2016 | Currie et al. |
| 9,382,256 B2 | 7/2016 | Casteel et al. |
| 9,504,684 B2 | 11/2016 | Blomqren et al. |
| 9,562,056 B2 | 2/2017 | Blomgren et al. |
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 9,918,939 B2 | 3/2018 | Casteel |
| 9,949,932 B2 | 4/2018 | Casteel et al. |
| 9,968,601 B2 | 5/2018 | Blomgren et al. |
| 9,974,792 B2 | 5/2018 | Di Paolo |
| 10,005,774 B2 | 6/2018 | Blomgren et al. |
| 10,080,756 B2 | 9/2018 | Di Paolo et al. |
| 10,092,583 B2 | 10/2018 | Blomqren et al. |
| 10,093,684 B2 | 10/2018 | Blomgren et al. |
| 10,111,882 B2 | 10/2018 | Abella et al. |
| 10,266,539 B2 | 4/2019 | Elford et al. |
| 10,342,794 B2 | 7/2019 | Blomgren et al. |
| 10,828,299 B2 | 11/2020 | Blomgren et al. |
| 10,842,803 B2 | 11/2020 | Blomgren et al. |
| 11,339,168 B2 | 5/2022 | Andres et al. |
| 11,517,570 B2 | 12/2022 | Blomgren et al. |
| 12,152,037 B2 | 11/2024 | Andres |
| 2002/0037852 A1 | 3/2002 | Browning et al. |
| 2003/0212073 A1 | 11/2003 | Currie et al. |
| 2004/0063715 A1 | 4/2004 | Paruch et al. |
| 2004/0067951 A1 | 4/2004 | Desimone et al. |
| 2004/0072081 A1 | 4/2004 | Coleman et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0044648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0222199 A1 | 10/2005 | Hayman et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0027135 A1 | 2/2007 | Bruncko et al. |
| 2007/0072860 A1 | 3/2007 | Bruncko et al. |
| 2007/0117804 A1 | 5/2007 | Zhao et al. |
| 2009/0197809 A1 | 8/2009 | Anderson et al. |
| 2010/0305122 A1 | 12/2010 | Bruncko et al. |
| 2010/0305125 A1 | 12/2010 | Borchardt et al. |
| 2011/0002989 A1 | 1/2011 | Curatolo et al. |
| 2011/0152273 A1 | 6/2011 | Arikawa et al. |
| 2012/0157470 A1 | 6/2012 | Catron et al. |
| 2013/0267496 A1 | 10/2013 | Mitchell et al. |
| 2013/0338142 A1 | 12/2013 | Blomgren et al. |
| 2014/0051696 A1 | 2/2014 | Lannutti et al. |
| 2014/0148430 A1 | 5/2014 | Blomgren et al. |
| 2015/0175626 A1 | 6/2015 | Cagulada et al. |
| 2015/0237860 A1 | 8/2015 | Anderson et al. |
| 2016/0168155 A1 | 6/2016 | Fung et al. |
| 2016/0220573 A1 | 8/2016 | Di Paolo et al. |
| 2016/0368918 A1 | 12/2016 | Blomgren et al. |
| 2016/0375019 A1 | 12/2016 | Di Paolo et al. |
| 2017/0035755 A1 | 2/2017 | Blomgren et al. |
| 2017/0217967 A1 | 8/2017 | Elford et al. |
| 2018/0071302 A1 | 3/2018 | Abella et al. |
| 2018/0071303 A1 | 3/2018 | Abella et al. |
| 2018/0086769 A1 | 3/2018 | Armistead et al. |
| 2018/0117052 A1 | 5/2018 | Di Paolo et al. |
| 2018/0280387 A1 | 10/2018 | Blomgren et al. |

FOREIGN PATENT DOCUMENTS

| | | |
|---|---|---|
| DE | 4337609 | 5/1995 |
| EP | 0 480 713 | 4/1992 |
| JP | 2001-302667 | 10/2001 |
| JP | 2004-528295 | 9/2004 |
| JP | 2005-530739 | 10/2005 |
| JP | 2008-519843 | 6/2008 |
| NZ | 593460 | 11/2013 |
| WO | WO 88/04298 | 6/1988 |
| WO | WO 95/12594 | 5/1995 |
| WO | WO 96/04298 | 2/1996 |
| WO | WO 96/004298 | 2/1996 |
| WO | WO 96/034866 | 11/1996 |
| WO | WO 96/34866 | 11/1996 |
| WO | WO 99/28322 | 6/1999 |
| WO | WO 01/27119 | 4/2001 |
| WO | WO 01/027119 | 4/2001 |
| WO | WO 01/34119 | 5/2001 |
| WO | WO 01/47495 | 7/2001 |
| WO | WO 01/083485 | 11/2001 |
| WO | WO 01/83485 | 11/2001 |
| WO | WO 02/010170 | 2/2002 |
| WO | WO 02/10170 | 2/2002 |
| WO | WO 02/030428 | 4/2002 |
| WO | WO 02/30428 | 4/2002 |
| WO | WO 02/060492 | 8/2002 |
| WO | WO 02/066481 | 8/2002 |
| WO | WO 02/076985 | 10/2002 |
| WO | WO 03/070732 | 8/2003 |
| WO | WO 03/089434 | 10/2003 |
| WO | WO 04/022562 | 3/2004 |
| WO | WO 04/026310 | 4/2004 |
| WO | WO 04/026867 | 4/2004 |
| WO | WO 04/072080 | 8/2004 |
| WO | WO 04/072081 | 8/2004 |
| WO | WO 05/005429 | 1/2005 |
| WO | WO 05/014599 | 2/2005 |
| WO | WO 05/019220 | 3/2005 |
| WO | WO 05/04 7290 | 5/2005 |
| WO | WO 05/085252 | 9/2005 |
| WO | WO 06/009769 | 1/2006 |
| WO | WO 06/044687 | 4/2006 |
| WO | WO 06/053121 | 5/2006 |
| WO | WO 08/025821 | 3/2008 |
| WO | WO 08/033854 | 3/2008 |
| WO | WO 09/039397 | 3/2009 |
| WO | WO 09/070639 | 6/2009 |
| WO | WO 09/077334 | 6/2009 |
| WO | WO 09/102252 | 8/2009 |
| WO | WO 09/137596 | 11/2009 |
| WO | WO 09/156284 | 12/2009 |
| WO | WO 10/000633 | 1/2010 |
| WO | WO 10/006947 | 1/2010 |
| WO | WO 10/027500 | 3/2010 |
| WO | WO 11/074961 | 6/2011 |
| WO | WO 11/112995 | 9/2011 |
| WO | WO 12/147832 | 11/2012 |
| WO | WO 13/188856 | 12/2013 |
| WO | WO 14/028665 | 2/2014 |

OTHER PUBLICATIONS

Ackler et al., 2012, Navitoclax (ABT-263) and bendamustine rituximab induce enhanced killing of non-Hodgkin's lymphoma tumours in vivo, British Journal of Pharmacology, 167:881-891.

Al-Dabbagh et al., 1984, Species Differences in Oxidative Drug Metabolism: Some Basic Considerations, Archives of Toxicology, Suppl. 7:219-231.

Ashizawa, 2002, en/kesshokei no saitekika to kesshokagijutsu (optimization of salt/crystal form and crystallization technique), Pharm Tech Japan, 18(10):81-96.

(56) References Cited

OTHER PUBLICATIONS

Bastin et al., 2000, Salt Selection and Optimisation Procedures for Pharmaceutical New Chemical Entities, Organic Process Research and Development, American Chemical Society, 4(5):427-435.

Berge et al., Jan. 1977, Pharmaceutical Salts, Journal of Pharmaceutical Sciences, 66(1):1-19.

Blazar et al., 2013, Advances in graft-versus host disease biology and therapy, Nat Rev Immunol., 12(6):443-458.

Bouloc et al., 2010, Structure-based design of imidazo[1,2-α]pyrazine derivatives as selective inhibitors of Aurora kinase in cells. Bioorganic & Medicinal Chemistry Letters, 20:5988-5993.

Brittain, 2009, Theory and principles of polymorphic systems, in Polymorphism in Pharmaceutical Solids, Informa Healthcare, New York, pp. 1-23.

Buchner et al., Jun. 2010, Spleen tyrosine kinase inhibition prevents chemokine- and integrin-mediated stromal protective effects in chronic lymphocytic leukemia, Blood, 115(22):4497-4506.

Bundgaard, H., (1985). Design of prodrugs: Bioreversible derivatives for various functional groups and chemical entities, Elsevier Science Publishers, B.V., The Netherlands, p. 1.

Burke et al., 2014, A potential therapeutic strategy for chronic lymphocytic leukemia by combining Idelalisib and GS-9973, a novel spleen tyrosine kinase (Syk) inhibitor, Oncotarget, 5(4):908-915.

Burrell et al., 2013, The causes and consequences of genetic heterogeneity in cancer evolution, Nature, 501:338-345.

CancerConnect.com, Aug. 17, 2013, Ibrutinib Highly Active in Patients with Chronic Lymphocytic Leukemia with 17p Deletion, 2 pp.

ClinicalTrials.gov, Jun. 2013, A Phase 2 of GS-9973 in Subjects With Relapsed or Refractory Hematologic Malignancies, NCT01799889, 5 pp.

Currie et al., 2014, Discovery of GS-9973, a Selective and Orally Efficacious Inhibitor of Spleen Tyrosine Kinase, J. Med. Chem., 57:3856-3873.

Dean, 2000, Recent Advances in the Synthesis and Applications of Radiolabeled Compounds for Drug Discovery and Development, Curr. Pharm Des. 6(10):Preface, 1 p.

Dean, D.C. (2000). "Recent Advances in the Synthesis and Applications of Radiolabeled Compounds for drug Discovery and Development," Curr. Pharm Des. 6(10): Preface, 1 page.

Ding et al., 2002, A Combinatorial Scaffold Approach Toward Kinase-Directed Heterocycle Libraries, J. Am Chem Soc., 124(8):1594-1596.

Ding, S. et al. (2002) "A Combinatorial Scaffold Approach Toward Kinase-Directed Heterocycle Libraries," J. Am Chem Soc., 124(8):1594-1596.

Elder et al., 2010, The Utility of Sulfonate Salts in Drug Development, J Pharm Sci, 99(7)2948-2961.

Evans, 1981, Synthesis of Radiolabeled Compounds, J. Radioanal. Chem. 64(1-2):9-32.

Flynn, Aug. 2014, B cells, T follicular helpers, and germinal centers as facilitators of chronic Graft-versus-Host disease. Doctoral Dissertation, University of Minnesota, 182 pp.

Gavezzotti, 1994, Are Crystal Structures Predictable? Acc. Chem. Res. 27(10):309-314.

GenBank Accession No. AY050647.1, created on Oct. 7, 2001, located at<http://www.ncbi.nlm.nih.gov/nuccore/AY050647.1>, last visited on Dec. 28, 2011, 1 page.

Golub et al., Oct. 15, 1999, Molecular Classification of Cancer: Class Discovery and Class Prediction by Gene Expression Monitoring, Science, 286"531-537.

Hackam et al., 2006, Translation of Research Evidence From Animals to Humans, JAMA, 296(14):1731-1732.

Hill et al., 2013, B-Cell Antigen Receptor Signaling in Chronic Lymphocytic Leukemia: Therapeutic Targets and Translational Opportunities, International Reviews of Immunology, 32:377-396.

Hirayama, Jul. 25, 2008, Handbook for creating organic compound crystals—principle and technical know-how, Maruzen KK, pp. 17-23, 37-40, 45-51 and 57-65.

Jeffrey et al., 1998, Phosphodiesterase III and V Inhibitors on Pulmonary Artery from Pulmonary Hypertensive Rats: Differences Between Early and established Pulmonary Hypertension, J. Cardiovascular Pharmacology, 32(2):213-219.

Jordan Mar. 2003, Tamoxifen: A Most Unlikely Pioneering Medicine, Nature Reviews: Drug Discovery 2:205-213.

Kabalka et al., 1989, The Synthesis of Radiolabeled Compounds via Organometallic Intermediates, Tetrahedron 45(21):6601-6621.

Kojima, Sep. 2008, Iyakuhin Kaihatsu ni okeru kettushousei sentaku no kouritsuka womezashite (Aiming at efficient crystallinity selection in medicine development), Journal of Pharmaceutical Science and Technology, Japan, 68(5)344-349.

Krisenko et al., Jan. 2015, Calling in SYK: SYK's Dual Role as a Tumor Promoter and Tumor Suppressor in Cancer, Biochim Biophys Acta., 1853(1):254-263.

Kuhnz et al., Jun. 11, 1998, Predicting the Oral Bioavailab ty of 19-Nortestosterone Progestins In Vivo From Their Metabolic Stab ty in Human Liver Microsomal Preparation In Vitro, The American Society for Pharmacology and Experimental Therapeutics, 26(11):1120-1127.

Le Huu et al., 2014, Blockade of Syk ameliorates the development of murine sclerodermatous chronic graft-vershost disease, Journal of Dermatological Science, 74:214-221.

Lumma et al., 1983, Piperazinylimidazo [1,2-α]pyrazines with Selective affinity for in Vitro adrenergic Receptor Subtypes, J. Med. Chem. 26(3):357-363.

Ma et al., 2011, Signal transduction inhibitors in chronic lymphocytic leukemia, Current Opinion in Oncology, 23:601-608.

Merino et al., 2012, Bcl-2, Bcl-xl, and Bcl-w are not equivalent targets of ABT-737 and navitoclax (ABT-263) in lymphoid and leukemic cells, Blood. 119(24):5807-5816.

National Cancer Institute, 2017, Cancer Types, A to Z List of Cancer Types, 8 pp.

Oracova et al., 1996, Drug-Protein Binding Studies New Trends in Analytical and Experimental Methodology, J Chromatography B, 677:1-28.

Owen et al., 2012, Obinutuzumab for the treatment of lymphoproliferative disorders, Expert Opinion Biol. Ther. 12(3):343-351.

Paulekuhn et al., 2007, Trends in Active Pharmaceutical Ingredient Salt Selection based on Analysis of the Orange Book Database, J. Med. Chem., 50:6665-6672.

Roberts et al., 2012, Substantial Susceptibility of Chronic Lymphocytic Leukemia to BCL2 Inhibition: Results of a Phase I Study of Navitoclax in Patients With Relapsed or Refractory Disease, J Clin Oncol, 30:488-496.

Serajuddin, 2007, Salt formation to improve drug solubility, Advanced Drug Delivery Reviews, 59:603-616.

Silverman, 1992, Prodrugs and drug delivery systems, in The Organic Chemistry of Drug Design and Drug Action, Academic Press, Inc., San Diego, CA, pp. 352-400.

Stenberg et al., 2000, KinMutBase, a Database of Human Disease-Causing Protein Kinase Mutations, Nucleic Acids Research 28(1):369-371.

Takata, 2007, API form screening and selection in drug discovery stage, Pharmstage, 6(10):20-25.

Taylor et al., 1984, Hydrogen-Bond Geometry in Organic Crystals, Acc. Chem Res. 17:320-326.

Vassilev et al., 2004, Therapeutic Potential of Inhibiting Bruton's Tyrosine Kinase, (BTK), Current Pharmaceutical Design, 10:1757-1766.

Vippagunta et al., 2011, Crystalline solids, Advanced Drug Delivery Reviews 48:3-26.

Vitze et al., 1999, New Imidazo [1,2-a]pyrazine Derivatives with Bronchodilatory and Cyclic Nucleotide Phosphodiesterase Inh tory Activities, Bioorganic and Medicinal Chemistry 7:1059-1065.

Willander et al, 2013, NOTCH1 Mutations Influence Survival in Chronic Lymphocytic Leukemia Patients, BMC Cancer , 13:274, 6 pp.

Zaragoza Dorwald, 2005, Side Reactions in Organic Synthesis: A Guide to Successful Synthesis Design, Weinheim; WILEY-VCH Verlag Gmbh & Co., Preface, 2 p.

(56) References Cited

OTHER PUBLICATIONS

European Communication mailed on Jun. 18, 2013, for EP Patent Application No. 11 709 600.8 filed on Mar. 11, 2011, 6 pages. (39.45).
European Communication mailed on Jun. 6, 2013, for EP Patent Application No. 09 832 228.2 filed on Jun. 21, 2011, 5 pages. (27.49).
European Communication mailed on Oct. 24, 2012, for European Patent Application No. 09710901.1, filed on Feb. 12, 2009, five pages. (38.43).
Examination Report for AU Appln. No. 2017228612 dated Jun. 8, 2018, 3 pages.
Examination Report for IN Appln. No. 201627023163 dated Aug. 31, 2018, 6 pages.
Extended European Search Report for EP Appln. No. 18156034.3 dated Jun. 6, 2018, 6 pages.
Extended European search report for European Application No. 19177110.4 dated Dec. 13, 2019. (1O paoes).
Extended European Search Report mailed on Apr. 26, 2012, for EP 09 83 2229, filed on Jun. 21, 2011, 6 pages. (28.48).
Extended European Search Report mailed on Jul. 27, 2012, for EP 09 83 2228.2, filed on Jun. 21, 2011, 12 pages. (27.49).
Extended European Search Report mailed on Mar. 12, 2014, for EP 13005979.3, filed on Dec. 20, 2013, 5 pages. (27.64).
Final Office Action mailed on Jan. 27, 2012, for U.S. Appl. No. 12/632,151, filed Dec. 7, 2009, 15 pages. (28.00).
Final Office Action mailed on May 2, 2013 for U.S. Appl. No. 13/343,624, filed Jan. 4, 2012, 9 pages. (38.01).
Final Office Action mailed on May 25, 2012, for U.S. Appl. No. 12/632,140, filed Dec. 7, 2009, 9 pages. (27.00).
Final Office Action mailed on Oct. 30, 2012, for U.S. Appl. No. 12/632,140, filed Dec. 7, 2009, 9 pages. (27.00).
Final Office Action mailed on Sep. 15, 2011, for U.S. Appl. No. 12/632,140, filed Dec. 7, 2009, 15 pages. (27.00).
Final Office Action mailed on Sep. 5, 2012, for U.S. Appl. No. 12/632,151, filed Dec. 7, 2009, 11 pages. (28.00).
International Preliminary Examination Report mailed on Aug. 5, 2004, for PCT Application No. PCT/US2003/12222, filed Apr. 21, 2003, 11 pages.
International Preliminary Examination Report mailed on Oct. 27, 2004, for PCT Application No. PCT/US2003/28329, filed on Sep. 9, 2003, 5 oaaes.
International Preliminary Report on Patentab ty mailed on Aug. 17, 2010, for PCT Application No. PCT/US2009/000919, filed on Feb. 12, 2009, 8 pages. (38.40).
International Preliminary Report on Patentab ty mailed on Jan. 5, 2011, for PCT Application No. PCT/US2009/006445, filed on Dec. 7, 2009, 6 pages. (27.40).
International Preliminary Report on Patentab ty mailed on Oct. 29, 2010, for PCT Application No. PCT/US/2009/006446, filed on Dec. 7, 2009, 6 pages. (28.40).
International Search Report and Written Opinion for International Application No. PCT/US2014/049032 dated Sep. 19, 2014. (8 pages).
International Search Report and Written Opinion mailed Mar. 3, 2015, for PCT Application No. PCT/US2014/068423, Filed Dec. 3, 2014.
International Search Report and Written Opinion mailed Oct. 13, 2014, for PCT Application No. PCT/US2014/048741, Filed Jul. 29, 2014.
International Search Report and Written Opinion mailed Dec. 30, 2004, for PCT Aoolication No. PCT/US2004/018227, filed on Jun. 4, 2004, 10 pages.
International Search Report and Written Opinion mailed on Dec. 8, 2004, for PCT Application No. PCT/US2004/021150, filed on Jun. 30, 2004, 10 pages.
International Search Report and Written Opinion mailed on Feb. 1, 2005 for PCT Application No. PCT/US2004/025884, filed on Aug. 11, 2004, 8 oaaes.
International Search Report and Written Opinion mailed on Jul. 7, 2004, for PCT Application No. PCT/US2004/003922, filed on Feb. 10, 2004, 12 pages.
International Search Report and Written Opinion mailed on Jul. 7, 2004, for PCT Application No. PCT/US2004/003923, filed on Feb. 10, 2004, 12 pages.
International Search Report and Written Opinion mailed on Jun. 23, 2005, for PCT Application No. PCT/US2004/037433, filed on Nov. 10, 2004, 15 paqes.
International Search Report and Written Opinion mailed on Oct. 8, 2014, for PCT Application No. PCT/US2014/048733, filed on Jul. 29, 2014.
International Search Report mailed Apr. 26, 2011, for Application No. PCT/US2011/028194, filed on Mar. 11, 2011, 5 oaaes. (39.40).
International Search Report mailed on Feb. 12, 2010, for PCT Application No. PCT/US/2009/006446, filed on Dec. 7, 2009, 3 pages. (28.40).
International Search Report mailed on Feb. 12, 2010, for PCT Application No. PCT/US2009/006445, filed on Dec. 7, 2009, 3 pages. (27.40).
International Search Report mailed on Feb. 9, 2004, for PCT Application No. PCT/US2003/28329, filed on Sep. 9, 2003.
International Search Report mailed on May 12, 2009, for PCT Application No. PCT/US2009/000919, filed on Feb. 12, 2009, 5 paqes. (38.40).
International Search Report mailed on Oct. 22, 2003, for PCT Application No. PCT/US2003/12222, filed on Apr. 21, 2003.
Invitation to Pay Additional Fees with Partial International Search Report mailed May 3, 2005, for PCT Application No. PCT/US2004/037433, filed on Nov. 10, 2004, 9 pages.
Japanese Decision of Patent mailed Feb. 4, 2014, for Japanese Patent Application No. 2010-546786, filed on Aug. 1, 2010, 4 oaaes. (with Enalish translation). (38.45).
Japanese Notice of Reasons for Rejection mailed on Feb. 4, 2014 for Japanese Patent Application No. 2011-539524, filed on Jun. 6, 2011, 10 pages. (with English translation). (27.53).
Japanese Notice of Reasons for Rejection mailed on Feb. 6, 2014, for Japanese Patent Application No. 2011-539525, filed on Jun. 6, 2011, 11 pages. (with English translation). (28.52).
Non-Final Office Action mailed on Apr. 13, 2011 for U.S. Appl. No. 12/370,103, filed Feb. 12, 2009, 11 pages. (38.00).
Non-Final Office Action mailed on Apr. 3, 2006, for U.S. Appl. No. 10/776,002, filed Feb. 10, 2004, 13 oaaes. (33.30).
Non-Final Office Action mailed on Dec. 31, 2013, for U.S. Appl. No. 13/901,523, filed May 23, 2013, 22 pages. (27.02).
Non-Final Office Action mailed on Feb. 17, 2012 for U.S. Appl. No. 12/632,140, filed Dec. 7, 2009, 11 pages. (27.00).
Non-Final Office Action mailed on Jan. 25, 2013, for U.S. Appl. No. 13/343,624, filed Jan. 4, 2012, 18 pages. (38.01).
Non-Final Office Action mailed on Jan. 8, 2007, for U.S. Appl. No. 10/915,696, filed Aug. 11, 2004, 8 pages. (34.00).
Non-Final Office Action mailed on Jun. 29, 2011, for U.S. Appl. No. 12/632,151, filed Dec. 7, 2009, 17 pages. (28.00).
Non-Final Office Action mailed on May 10, 2011 for U.S. Appl. No. 12/632,140, filed Dec. 7, 2009, 18 pages. (27.00).
Non-Final Office Action mailed on May 17, 2012, for U.S. Appl. No. 12/632,151, filed Dec. 7, 2009, 15 paoes. (28.00).
Non-Final Office Action mailed on May 24, 2006, for U.S. Appl. No. 10/776,631, filed Feb. 10, 2004, 10 pages. (33.00).
Non-Final Office Action mailed on Nov. 4, 2013, for U.S. Appl. No. 13/862,147, filed Apr. 12, 2013, 18 oaaes. (28.01).
Non-Final Office Action mailed on Oct. 11, 2012, for U.S. Appl. No. 13/441,441, filed Apr. 6, 2012, 8 pages. (27.20).
Non-Final Office Action mailed on Oct. 11, 2013, for U.S. Appl. No. 13/868,967, filed Apr. 23, 2013, 17 pages. (27.01).
Non-Final Office Action mailed on Oct. 16, 2013, for U.S. Appl. No. 13/868,971, filed Apr. 23, 2013, 16 pages. (27.10).
Non-Final Office Action mailed on Sep. 26, 2006, for U.S. Appl. No. 10/658,121, filed Sep. 9, 2003, 7 paqes. (32.00).
Notice of Allowance mailed Apr. 20, 2007, for U.S. Appl. No. 10/915,696, filed Aug. 11, 2004, 7 pages. (34.00).
Notice of Allowance mailed Aug. 11, 2006, for U.S. Appl. No. 10/776,002, filed Feb. 10, 2004, 10 paqes. (33.30).

(56) References Cited

OTHER PUBLICATIONS

Notice of Allowance mailed Aug. 8, 2007, for U.S. Appl. No. 10/658,121, filed Sep. 9, 2003, 4 pages. (32.00).
Notice of Allowance mailed Mar. 6, 2007, for U.S. Appl. No. 10/658,121, filed Sep. 9, 2003, 6 oaaes. (32.00).
Notice of Allowance mailed on Aug. 12, 2013, for U.S. Appl. No. 13/343,624, filed Jan. 4, 2012 , 9 pages. (38.01).
Notice of Allowance mailed on Dec. 26, 2013, for U.S. Appl. No. 13/343,624, filed Jan. 4, 2012 , 10 paqes. (38.01).
Notice of Allowance mailed on Feb. 12, 2014, for U.S. Appl. No. 13/862,147, filed Apr. 12, 2013, 9 pages. (28.01).
Notice of Allowance mailed on Feb. 5, 2014, for U.S. Appl. No. 13/868,967, filed Apr. 23, 2013, 8 oaaes. (27.01).
Notice of Allowance mailed on Jan. 14, 2013, for U.S. Appl. No. 12/632,151, filed Dec. 7, 2009, 8 pages. (28.00).
Notice of Allowance mailed on Jan. 25, 2013, for U.S. Appl. No. 12/632,140, filed Dec. 7, 2009, 8 pages. (27.00).
Notice of Allowance mailed on Jan. 28, 2013, for U.S. Appl. No. 13/441,441, filed Apr. 6, 2012, 8 pages. (27.20).
Notice of Allowance mailed on Jan. 30, 2014, for U.S. Appl. No. 13/868,971, filed Apr. 23, 2013, 8 paqes. (27.10).
Notice of Allowance mailed Sep. 7, 2006, for U.S. Appl. No. 10/776,631, filed Feb. 10, 2004, 7 pages. (33.00).
Office Action Dated Dec. 15, 2014 for Japan Patent Application No. 2014-095907.
Office Action Dated Jan. 15, 2015 for Chilean Patent Application No. 1360-11.
Office Action Dated Jan. 30, 2015 for Vietnamese Patent Application No. 1-2011-01623.
Office Action Dated Feb. 18, 2015 for Eurasian Patent Application No. 201400197.
Office Action Dated Mar. 30, 2015 for European Patent Application No. 13 005 979.3.
Office Action dated Jun. 8, 2017 for JP Appl. No. 2016-560876, 3 pages.
Office Action for BO Appln. No. SP-0316-2014 dated Aug. 2, 2018, 2 pages.
Office Action for BO Appln. No. SP-0316-2014 dated Feb. 8, 2018, 5 pages.
Office Action for CL Appln. No. 1537-2016 dated Sep. 20, 2018, 7 pages.
Office Action for CU Appln. No. 2016-0097 dated May 17, 2018, 2 pages.
Office Action for DO Appln. No. P2016-0140 dated Feb. 13, 2018, 2 pages.
Office Action for DO Appln. No. P2016-0140 dated Oct. 12, 2018, 2 pages.
Office Action for JP Appln. No. 2017-172941 dated Nov. 22, 2018, 2 pages.
Office Action for SV Appln. No. 2016005229 dated May 2, 2018, 6 pages.
Office Action for TT Appln. No. TT/A/2016/00058 dated Jun. 8, 2018, 1 page.
Office Action for TW Appln. No. 103144664 dated Jul. 6, 2018, 4 pages.
Office Action for UA Appln. No. A201606436 dated Jun. 17, 2018, 4 pages.
Office Action for UA Appln. No. A201606436 dated Mar. 1, 2018, 5 pages.
Partial European Search Report for European Application No. 19177110.4 dated Aug. 29, 2019 (1O pages).
Resolution Dated Dec. 18, 2014 for Colombian Patent Application No. 14-049.611.
Restriction Requirement mailed Dec. 8, 2010, for U.S. Appl. No. 12/632,140, filed Dec. 7, 2009, 1O oaaes. (27.00).
Restriction Requirement mailed Jan. 27, 2006, for U.S. Appl. No. 10/776,631, filed Feb. 10, 2004, 6 pages. (33.00).
Restriction Requirement mailed Jan. 30, 2006, for U.S. Appl. No. 10/658,121, filed Sep. 9, 2003, 5 pages. (32.00).
Restriction Requirement mailed Jan. 4, 2006, for U.S. Appl. No. 10/776,002, filed Feb. 10, 2004, 7 pages. (33.30).
Restriction Requirement mailed May 18, 2006, for U.S. Appl. No. 10/658,121, filed Sep. 9, 2003, 5 pages. (32.00).
Restriction Requirement mailed Oct. 13, 2006, for U.S. Appl. No. 10/915,696, filed Aug. 11, 2004, 5 pages. (34.00).
Restriction Requirement mailed Oct. 20, 2004, for U.S. Appl. No. 10/419,682, filed Apr. 21, 2003, 9 paoes.
Restriction Requirement mailed on Apr. 14, 2014, for U.S. Appl. No. 13/862,194, filed Apr. 12, 2013, 5 pages. (28.10).
Restriction Requirement mailed on Dec. 8, 2010, for U.S. Appl. No. 12/632,151, filed Dec. 7, 2009, 10 oaaes. (28.00).
Restriction Requirement mailed on Feb. 17, 2011, for U.S. Appl. No. 12/370,103, filed Feb. 12, 2009, 10 pages. (38.00).
Restriction Requirement mailed on Jan. 27, 2014, for U.S. Appl. No. 13/609,068, filed Nov. 26, 2012, 8 pages. (39.00).
Restriction Requirement mailed on Jul. 26, 2012, for U.S. Appl. No. 13/441,441, filed Apr. 6, 2012, 9 pages. (27.20).
Restriction Requirement mailed on Jul. 3, 2013, for U.S. Appl. No. 13/868,971, filed Apr. 23, 2013, 5 paqes. (27.10).
Restriction Requirement mailed on Jun. 14, 2013, for U.S. Appl. No. 13/862,147, filed Apr. 12, 2013, 1O pages. (28.01).
Restriction Requirement mailed on Jun. 24, 2013, for U.S. Appl. No. 13/868,967, filed Apr. 23, 2013, 1O paoes. (27.01).
Restriction Requirement mailed on Nov. 27, 2012, for U.S. Appl. No. 13/343,624, filed Jan. 4, 2012, 10 pages. (38.01).
Restriction Requirement mailed on Oct. 15, 2013, for U.S. Appl. No. 13/901,523, filed May 23, 2013, 5 paoes. (27.02).
Restriction Requirement mailed on Sep. 8, 2014, for U.S. Appl. No. 14/274,618, filed May 9, 2014, 6 pages. (27.03).
Second Written Opinion mailed on Apr. 13, 2004, for PCT Application No. PCT/US2003/12222, filed Apr. 21, 2003, 7 oaaes.
Written Opinion mailed Apr. 26, 2011, for Application No. PCT/US2011/028194, filed on Mar. 11, 2011, 6 pages. (39.40).
Written Opinion mailed Dec. 5, 2003, for PCT Application No. PCT/US2003/12222, filed Apr. 21, 2003, 6 pages.
Written Opinion mailed Jul. 6, 2004, for PCT Application No. PCT/US2003/28329, filed on Sep. 9, 2003, 5 pages. (32.40).
Written Opinion mailed on Feb. 12, 2010, for PCT Application No. PCT/US/2009/006446, filed on Dec. 7, 2009, 4 paoes. (28.40).
Written Opinion mailed on Feb. 12, 2010, for PCT Application No. PCT/US2009/006445, filed on Dec. 7, 2009, 4 pages. (27.40).
Written Opinion mailed on May 12, 2009, for PCT Application No. PCT/US2009/000919, filed on Feb. 12, 2009, 7 pages.(38.40).
Caira, Jan. 1998, Crystalline polymorphism of organic compounds, Topics in Current Chemistry, 198:163-208.
Sarma et al., 2011, Solid formation of pharmaceuticals: Polymorphs, salt and cocrystals. Korean J.Chem.Eng., 28(2):315-322.
Variankaval et al., 2008, From form to function: Crystallization of active pharmaceutical ingredients, AIChE, 54(7):1682-1688.

XRPD Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I NMR Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I DSC Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I TGA Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I XRPD Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II NMR Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II DSC Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II XRPD Analysis of 6-(6-aminopyrazin-2-yl)-N-(4-(4-(oxetan-3-yl)piperazin-1-yl)phenyl)imidazo[1,2-a]pyrazin-8-amine Succinate Form I NMR Analysis of 6-(6-aminopyrazin-2-yl)-N-(4-(4-(oxetan-3-yl)piperazin-1-yl)phenyl)imidazo[1,2-a]pyrazin-8-amine Succinate Form I DSC Analysis of 6-(6-aminopyrazin-2-yl)-N-(4-(4-(oxetan-3-yl)piperazin-1-yl)phenyl)imidazo[1,2-a]pyrazin-8-amine Succinate Form I TGA Analysis of 6-(6-aminopyrazin-2-yl)-N-(4-(4-(oxetan-3-yl)piperazin-1-yl)phenyl)imidazo[1,2-a]pyrazin-8-amine Succinate Form I XRPD Analysis of 6-(6-aminopyrazin-2-yl)-N-(4-(4-(oxetan-3-yl)piperazin-1-yl)phenyl)imidazo[1,2-a]pyrazin-8-amine Succinate Form II NMR Analysis of 6-(6-aminopyrazin-2-yl)-N-(4-(4-(oxetan-3-yl)piperazin-1-yl)phenyl)imidazo[1,2-a]pyrazin-8-amine Succinate Form II DSC Analysis of 6-(6-aminopyrazin-2-yl)-N-(4-(4-(oxetan-3-yl)piperazin-1-yl)phenyl)imidazo[1,2-a]pyrazin-8-amine Succinate Form II

CRYSTALLINE SUCCINATE SALT OF 6-(6-AMINOPYRAZIN-2-YL)-N-(4-(4-(OXETAN-3-YL)PIPERAZIN-1-YL)PHENYL)IMIDAZO[1,2-A]PYRAZIN-8-AMINE AS A SYK INHIBITOR

CROSS-REFERENCE TO RELATED APPLICATIONS

This application is a continuation of U.S. application Ser. No. 15/945,685, filed Apr. 4, 2018, now U.S. Pat. No. 10,342,794, which is a continuation of U.S. application Ser. No. 15/017,394, filed Feb. 5, 2016, now U.S. Pat. No. 9,968,601, which is a continuation of U.S. application Ser. No. 14/578,973, filed Dec. 22, 2014, now U.S. Pat. No. 9,290,505, which claims benefit under 35 U.S.C. § 119(e) to U.S. Provisional Application No. 61/920,407, filed Dec. 23, 2013, each of which is hereby incorporated by reference in its entirety.

FIELD

The present disclosure relates to compounds and to their use in the treatment of various diseases, including cancer and inflammatory conditions. The disclosure also relates to methods for preparation of the compounds and to pharmaceutical compositions comprising such compounds.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

The inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may also be useful in treating certain types of cancer, including B-cell lymphoma and leukemia. U.S. Pat. Nos. 8,455,493 and 8,440,667 disclose Syk inhibitors, the disclosures of which are hereby incorporated by reference in their entirety.

There is a continued need to provide compounds that are effective Syk inhibitors, including compounds having desirable pharmacokinetic properties for use as therapeutics for treating cancers and other diseases.

SUMMARY

Accordingly, the present disclosure provides compounds that function as Syk inhibitors. In one embodiment, the disclosure provides a compound of Formula I:

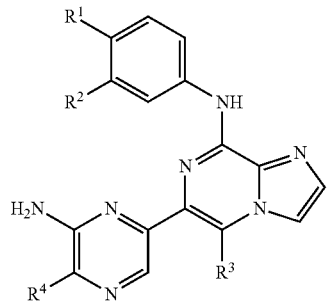

Formula I or a pharmaceutically acceptable salt, pharmaceutically acceptable co-crystal, pharmaceutically acceptable ester, stereoisomer, mixture of stereoisomers or tautomer thereof, wherein:

$R^1$ is selected from the group consisting of

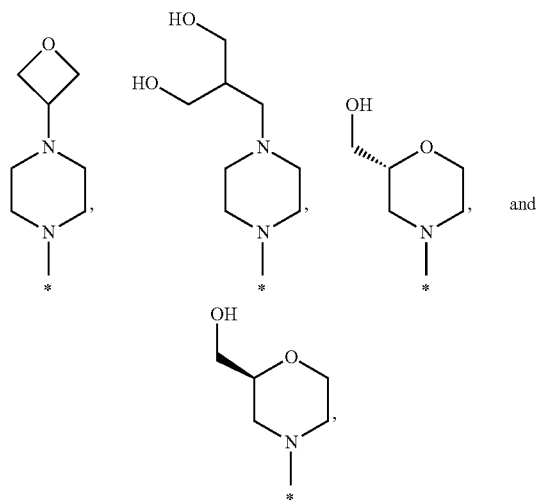

wherein * indicates the carbon atom of the indicated phenyl ring of Formula I to which $R^1$ is attached;
$R^2$ is H or 2-hydroxyethoxyl;
$R^3$ is H or methyl; and
$R^4$ is H or methyl.

Within each of the embodiments described herein comprising a compound of Formula I, there is a further embodiment wherein each of $R^2$, $R^3$, and $R^4$ is H. Within each of the embodiments described herein comprising a compound of Formula I, there is a another embodiment wherein $R^2$ is H, $R^3$ is methyl, and $R^4$ is H. Within each of the embodiments described herein comprising a compound of Formula I, there is also another embodiment wherein $R^2$ is H, $R^3$ is H, and $R^4$ is methyl.

Within each of the embodiments described herein comprising a compound of Formula I, there is still another embodiment wherein $R^2$ is 2-hydroxyethoxyl, $R^3$ is methyl, and $R^4$ is H. Within each of the embodiments described herein comprising a compound of Formula I, there is still another embodiment wherein $R^2$ is 2-hydroxyethoxyl, $R^3$ is methyl, and $R^4$ is H. Within each of the embodiments described herein comprising a compound of Formula I, there is still further embodiment wherein $R^2$ is 2-hydroxyethoxyl, $R^3$ is H. and $R^4$ is methyl.

Provided herein are also methods of using the compound of Formula I, or a pharmaceutically acceptable salt or co-crystal thereof, in the treatment of a disease or condition in a subject, such as a human. Provided herein are also methods of using the compound of Formula II, shown below, or a pharmaceutically acceptable salt or co-crystal thereof, in the treatment of a disease or condition in a subject, such as a human. Also provided is a compound of Formula I, or a pharmaceutically acceptable salt or co-crystal thereof, for use in therapy. Also provided is a compound of Formula II, or a pharmaceutically acceptable salt or co-crystal thereof, for use in therapy. Also provided is a compound of Formula I, or a pharmaceutically acceptable salt or co-crystal thereof, for use in the treatment of a disease or condition in a subject, such as a human. Also provided is a compound of Formula II, or a pharmaceutically acceptable salt or co-crystal thereof, for use in the treatment of a disease or condition in a subject, such as a human. Also provided are uses of the compound of Formula I, or a pharmaceutically acceptable salt or co-crystal thereof, in the manufacture of a medicament for the treatment of disease or condition in a subject, such as a human. Also provided are uses of the compound of Formula II, or a pharmaceutically acceptable salt or co-crystal thereof, in the manufacture of a medicament for the treatment of disease or condition in a subject, such as a human. Such diseases and conditions include inflammatory disorders, allergic disorders, autoimmune diseases, or a cancer (including carcinoma, sarcoma, melanoma, lymphoma and leukemia).

In some instances, the diseases and conditions that may be treated with the compounds disclosed herein include cancers such as bladder cancer, breast cancer, colorectal cancer, endometrial cancer, kidney/renal-cell cancer, lung cancer, pancreatic cancer, prostate cancer, thyroid cancer, leukemia, melanoma, and non-Hodgkin's lymphoma.

In some embodiments, the disease is cancer, including a hematologic malignancy or a solid tumor. In some embodiments, the cancer is lymphoma, multiple myeloma, or leukemia. In some embodiments, the hematologic malignancy is leukemia or lymphoma.

In some embodiments, the disclosure provides pharmaceutical compositions comprising a compound of Formula I, or a pharmaceutically acceptable salt or co-crystal thereof, and a pharmaceutically acceptable vehicle. In other embodiments, the disclosure provides pharmaceutical compositions comprising a compound of Formula II, or a pharmaceutically acceptable salt or co-crystal thereof, and a pharmaceutically acceptable vehicle.

In some embodiments, the disclosure provides pharmaceutical compositions comprising a therapeutically effective amount of a compound of Formula I, or a pharmaceutically acceptable salt, pharmaceutically acceptable co-crystal, pharmaceutically acceptable ester, stereoisomer, mixture of stereoisomers or tautomer thereof, and at least one pharmaceutically acceptable vehicle. In other embodiments, the disclosure provides pharmaceutical compositions comprising a therapeutically effective amount of a compound of Formula II, or a pharmaceutically acceptable salt, pharmaceutically acceptable co-crystal, pharmaceutically acceptable ester, stereoisomer, mixture of stereoisomers or tautomer thereof, and at least one pharmaceutically acceptable vehicle. Examples of pharmaceutically acceptable vehicle may be selected from carriers and other excipients, adjuvants and the like.

Also provided are methods of treating a disease or condition in a subject in need thereof by administering to the subject a therapeutically effective amount of a compound of Formula I, or a pharmaceutically acceptable salt, pharmaceutically acceptable co-crystal, pharmaceutically acceptable ester, stereoisomer, mixture of stereoisomers or tautomer thereof, or a pharmaceutical composition thereof. In one variation of a method of treating a disease or condition in a subject in need thereof (e.g., a human in need thereof), the method comprises administering to the subject a therapeutically effective amount of a compound of Formula I, or a pharmaceutically acceptable salt or co-crystal thereof. In some embodiments, the disease or condition is an inflammatory disorder, an allergic disorder, an autoimmune disease, or a cancer.

Also provided is a method of inhibiting kinase activity of a Syk kinase polypeptide by contacting the polypeptide with a compound of Formula I or a pharmaceutically acceptable salt, pharmaceutically acceptable co-crystal, pharmaceutically acceptable ester, stereoisomer, mixture of stereoisomers or tautomer thereof. Also provided is a method of inhibiting kinase activity of a Syk kinase polypeptide by contacting the polypeptide with a compound of Formula II or a pharmaceutically acceptable salt, pharmaceutically acceptable co-crystal, pharmaceutically acceptable ester, stereoisomer, mixture of stereoisomers or tautomer thereof. In one aspect is provided a method of inhibiting kinase activity of a Syk kinase polypeptide by contacting the polypeptide with a compound of Formula I or a pharmaceutically acceptable salt or co-crystal thereof. In one aspect, these methods of inhibiting kinase activity are performed in vitro. In another aspect is provided a method of inhibiting kinase activity of a Syk kinase polypeptide by contacting the polypeptide with a compound of Formula II or a pharmaceutically acceptable salt or co-crystal thereof. In one aspect, these methods of inhibiting kinase activity are performed in vitro.

Also provided is a kit that includes a compound of Formula I, or a pharmaceutically acceptable salt, pharmaceutically acceptable co-crystal, pharmaceutically acceptable ester, stereoisomer, mixture of stereoisomers or tautomer thereof. Also provided is a kit that includes a compound of Formula II, or a pharmaceutically acceptable salt, pharmaceutically acceptable co-crystal, pharmaceutically acceptable ester, stereoisomer, mixture of stereoisomers or tautomer thereof. In one aspect, the kit comprises a compound of Formula I, or a pharmaceutically acceptable salt or co-crystal thereof. In a further aspect, the kit comprises a compound of Formula II, or a pharmaceutically acceptable salt or co-crystal thereof. The kit may comprise a label and/or instructions for use of the compound in the treatment of a disease or condition in a subject (e.g., human) in need thereof. In some embodiments, the disease or condition may be associated with or mediated by Syk activity.

Also provided are articles of manufacture that include a compound of Formula I, or a pharmaceutically acceptable salt, pharmaceutically acceptable co-crystal, pharmaceutically acceptable ester, stereoisomer, mixture of stereoisomers or tautomer thereof, and a container. Also provided are articles of manufacture that include a compound of Formula II, or a pharmaceutically acceptable salt, pharmaceutically acceptable co-crystal, pharmaceutically acceptable ester, stereoisomer, mixture of stereoisomers or tautomer thereof, and a container. In one aspect, the article of manufacture comprises a compound of Formula I, or a pharmaceutically acceptable salt or co-crystal thereof. In one embodiment, the container may be a vial, jar, ampoule, preloaded syringe, or an intravenous bag. In another aspect, the article of manufacture comprises a compound of Formula II, or a pharmaceutically acceptable salt or co-crystal thereof. In one embodiment, the container may be a vial, jar, ampoule, preloaded syringe, or an intravenous bag.

In some embodiments, the invention relates to a compound of Formula I, or a pharmaceutically acceptable salt or co-crystal thereof. In some embodiments, the invention relates to a compound of Formula II, or a pharmaceutically acceptable salt or co-crystal thereof.

Additional aspects and embodiments of this disclosure are described throughout.

DETAILED DESCRIPTION

Figure 1:
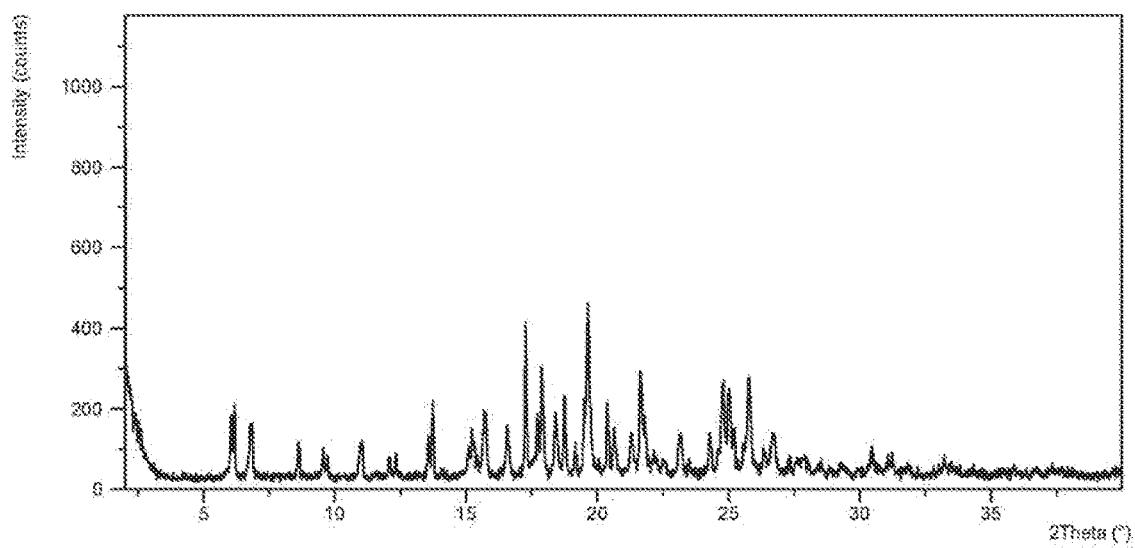
FIG. 1 is an XRPD Analysis of Mono MSA Salt Form I of the compound of Example 2.

It has surprisingly been discovered that compounds of Formula I, or pharmaceutically acceptable salts or co-crystals thereof, possess advantageous properties, making them attractive compounds for use as described herein. The compounds, in addition to being Syk inhibitors, possess desirable solubility and pharmacokinetic properties. These findings are particularly striking in view of the properties of comparable parameters of compounds of similar base structure.

The following description sets forth exemplary methods, parameters and the like. It should be recognized, however, that such description is not intended as a limitation on the scope of the present disclosure but is instead provided as a description of exemplary embodiments.

Also described for a compound of Formula I are the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds.

The compounds of the disclosure may possess an asymmetric center, and can be produced as a racemic mixture or as individual enantiomers. The individual enantiomers may be obtained by asymmetric synthesis or by resolving a racemic or non-racemic mixture of an intermediate at some appropriate stage of the synthesis. The individual enantiomers may also be obtained by resolution of the compound by conventional means, such as crystallization in the presence of a resolving agent, or chromatography, using, for example a chiral high pressure liquid chromatography (HPLC) column. The individual enantiomers as well as racemic and non-racemic mixtures of enantiomers are within the scope of the present disclosure, all of which are intended to be included within the structures depicted in this specification unless otherwise specifically indicated.

Definitions

As used in the present disclosure, the following words and phrases are generally intended to have the meanings as set forth below, except to the extent that the context in which they are used indicates otherwise.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" or "pharmaceutically effective amount" refers to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I, or a pharmaceutically acceptable salt or co-crystal thereof, is an amount sufficient to modulate Syk expression or activity, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition of Syk activity.

The term "polymorph" refers to different crystal structures of a crystalline compound. The different polymorphs may result from differences in crystal packing (packing polymorphism) or differences in packing between different conformers of the same molecule (conformational polymorphism). It is understood that any polymorph of a compound of Formula I, or a pharmaceutically acceptable salt or co-crystal thereof, used in the treatment of a disease or condition as described herein, while possibly providing varied properties, including pharmacokinetic properties, once absorbed into the subject, results in the compound of Formula I or a compound of Formula II, such that the use of a compound of Formula I or a compound of Formula II encompasses the use of any polymorph of a compound of Formula I or a compound of Formula II, respectively, or a pharmaceutically acceptable salt or co-crystal thereof.

The term "solvate" refers to a complex formed by the combining of a compound of Formula I or a compound of Formula II and a solvent. It is understood that any solvate of a compound of Formula I or a compound of Formula II used in the treatment of a disease or condition as described herein, while possibly providing varied properties, including pharmacokinetic properties, once absorbed into the subject, results in the compound of Formula I or a compound of Formula II, such that the use of a compound of Formula I or a compound of Formula H encompasses the use of any solvate of a compound of Formula I or a compound of Formula II, respectively.

The term "hydrate" refers to the complex formed by the combining of a compound of Formula I or a compound of Formula II, or a pharmaceutically acceptable salt or co-crystal thereof, and water. It is understood that any hydrate of a compound of Formula I or a compound of Formula II, or a pharmaceutically acceptable salt or co-crystal thereof, used in the treatment of a disease or condition as described herein, while possibly providing varied properties, including pharmacokinetic properties, once absorbed into the subject, results in the compound of Formula I or of Formula II, such that the use of a compound of Formula I or Formula II encompasses the use of any hydrate of a compound of Formula I or Formula II, respectively.

The term "prodrug" refers to a compound derived from or readily converted to a compound of Formula I or of Formula II that include chemical groups which, in vivo, can be converted and/or can be split off from the remainder of the molecule to provide a compound of Formula I or of Formula II or active moiety of the drug, or a pharmaceutically acceptable salt or co-crystal thereof or a biologically active metabolite thereof. It is understood that any prodrug of a compound of Formula I or of Formula II used in the treatment of a disease or condition as described herein, while possibly providing varied properties, including pharmacokinetic properties, once absorbed into the subject, results in the compound of Formula I or Formula II, such that the use of a compound of Formula I or Formula II encompasses the use of any prodrug of a compound of Formula I or Formula II, respectively. Prodrugs can, for example, be produced by replacing functionalities present in the compounds of the invention with appropriate moieties which are metabolized in vivo to form a compound of the invention. The design of prodrugs is well-known in the art, as discussed in Bundgaard, Design of Prodrugs 1985 (Elsevier), The Practice of Medicinal Chemistry 2003, 2nd Ed, 561-585 and Leinweber, Drug Metab. Res. 1987, 18: 379.

Examples of prodrugs of compounds of the invention are esters and amides of the compounds of the invention. For example, where the compound of the invention contains an alcohol group (—OH), the hydrogen atom of the alcohol group may be replaced in order to form an ester (e.g. the hydrogen atom may be replaced by —C(O)C$_{1-6}$alkyl. Where the compound of the invention contains a primary or secondary amino group, one or more hydrogen atoms of the amino group may be replaced in order to form an amide (e.g. one or more hydrogen atoms may be replaced by C(O)C$_{1-6}$alkyl).

Also provided herein are isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}$H (deuterium, D), $^{3}$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^{3}$H, $^{13}$C and $^{14}$C are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, pharmaceutically acceptable esters, pharmaceutically acceptable solvates, hydrates, enantiomers, mixture of enantiomers, tautomers, polymorphs, and pharmaceutically acceptable prodrugs thereof.

The disclosure also includes the compound of Formula I, or a pharmaceutically acceptable salt or co-crystal thereof, in which from 1 to n hydrogens attached to a carbon atom is/are replaced by deuterium, in which n is the number of hydrogens in the molecule. Such compounds may exhibit increased resistance to metabolism and are thus useful for increasing the half life of the compound of Formula I, or a pharmaceutically acceptable salt or co-crystal thereof, when administered to a mammal See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "inhibition" indicates a decrease, such as a significant decrease, in the baseline activity of a biological activity or process. "Inhibition of Syk activity" refers to a decrease in Syk activity as a direct or indirect response to the presence of a compound of Formula I, or a pharmaceutically acceptable salt or co-crystal thereof, relative to the activity of Syk in the absence of such compound or a pharmaceutically acceptable salt or co-crystal thereof. The decrease in activity may be due to the direct interaction of the compound with Syk, or due to the interaction of the compound(s) described herein with one or more other factors that in turn affect Syk activity. For example, the presence of the compound(s) may decrease Syk activity by directly binding to the Syk, by causing (directly or indirectly) another factor to decrease Syk activity, or by (directly or indirectly) decreasing the amount of Syk present in the cell or organism. In some embodiments, the inhibition of Syk activity may be compared in the same subject prior to treatment, or other subjects not receiving the treatment.

Inhibition of Syk activity also refers to observable inhibition of Syk activity in a standard biochemical assay for Syk activity, such as the ATP hydrolysis assay described in Example 12 below.

In some embodiments, the compound described herein, e.g. a compound of Formula I, or a pharmaceutically acceptable salt or co-crystal thereof, inhibits Syk kinase activity with an $IC_{50}$ value less than or equal to 1 micromolar, such as 0.1 nM to 1 µM or 1 nM to 1 µM. In some embodiments, the compound or a pharmaceutically acceptable salt or co-crystal thereof has an $IC_{50}$ value less than or equal to less than 500 nanomolar, such as 0.1 nM to 500 nM or 1 nM to 500 nM. In some embodiments, the compound or a pharmaceutically acceptable salt or co-crystal thereof has an $IC_{50}$ value less than or equal to less than 200 nanomolar, such as 0.1 nM to 200 nM or 1 nM to 200 nM. In some embodiments, the compound or a pharmaceutically acceptable salt or co-crystal thereof has an $IC_{50}$ value less than or equal to less than 100 nanomolar, such as 0.1 nM to 100 nM or 1 nM to 100 nM. In some embodiments, the compound or a pharmaceutically acceptable salt or co-crystal thereof has an $IC_{50}$ value less than or equal to 50 nanomolar, such as 0.1 nM to 50 nM or 1 nM to 50 nM. In some embodiments, the compound or a pharmaceutically acceptable salt or co-crystal thereof has an $IC_{50}$ value less than or equal to 20 nanomolar, such as 0.1 nM to 20 nM or 1 nM to 20 nM. In some embodiments, the compound or a pharmaceutically acceptable salt or co-crystal thereof has an $IC_{50}$ value less than or equal to 10 nanomolar, such as 0.1 nM to 10 nM or 1 nM to 10 nM. In some embodiments, the $IC_{50}$ value is measured as described in the assay of Example 12.

"Inhibition of B-cell activity" refers to a decrease in B-cell activity as a direct or indirect response to the presence of a compound of Formula I, or a pharmaceutically acceptable salt or co-crystal thereof, relative to the activity of B-cells in the absence of such compound or a pharmaceutically acceptable salt or co-crystal thereof. The decrease in activity may be due to the direct interaction of the compound with Syk or with one or more other factors that in turn affect B-cell activity.

Inhibition of B-cell activity also refers to observable inhibition of CD86 expression in a standard assay. In some embodiments, the compound described herein has an $IC_{50}$ value less than or equal to 10 micromolar, such as 1 nM to 10 µM or 10 nM to 10 µM. In some embodiments, the compound has an $IC_{50}$ value less than or equal to less than 1 micromolar, such as 1 nM to 1 µM or 10 nM to 1 µM. In some embodiments, the compound has an $IC_{50}$ value less than or equal to 500 nanomolar, such as 1 nM to 500 nM or 10 nM to 500 nM.

"B cell activity" also includes activation, redistribution, reorganization, or capping of one or more various B cell membrane receptors, or membrane-bound immunoglobulins, e.g., IgM, IgG, and IgD. Most B cells also have membrane receptors for the Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with a compound of Formula I, or a pharmaceutically acceptable salt or co-crystal thereof as compared to a matched sample not contacted with the compound(s).

Inhibition of B-cell proliferation also refers to observable inhibition of B-cell proliferation in a standard thymidine incorporation assay for B-cell proliferation, e.g. such assay as known in the art. In some embodiments, the compounds described herein, e.g. a compound of Formula I, or a pharmaceutically acceptable salt or co-crystal thereof, has an $IC_{50}$ value less than or equal to 10 micromolar, such as 1 nM to 10 µM or 10 nM to 10 µM. In some embodiments, the compound or a pharmaceutically acceptable salt or co-crystal thereof has an $IC_{50}$ value less than or equal to less than 1 micromolar, such as 1 nM to 1 µM or 10 nM to 1 µM. In some embodiments, the compound or a pharmaceutically acceptable salt or co-crystal thereof has an $IC_{50}$ value less than or equal to 500 nanomolar, such as 1 nM to 500 nM or 10 nM to 500 nM. In some embodiments, the compound or a pharmaceutically acceptable salt or co-crystal thereof has an $IC_{50}$ value less than or equal to 200 nanomolar, such as 1 nM to 200 nM or 10 nM to 200 nM. In some embodiments, the compound or a pharmaceutically acceptable salt or co-crystal thereof has an $IC_{50}$ value less than or equal to 100 nanomolar, such as 1 nM to 100 nM or 10 nM to 100 nM.

The "reduction in basophil activation" refers to the ability of compounds as described herein to reduce the activation of basophils. Basophil activation is involved, for example, in inflammatory and autoimmune diseases as described herein, and the reduction of activation of basophils is desired in compounds as described herein, e.g. a compound of Formula I, or a pharmaceutically acceptable salt or co-crystal thereof. The activation of basophils can be assessed by the measurement of CD63 expression by basophils, such as by a CD63 human whole blood basophil cellular assay (25% blood), e.g. such as the assay described in Example 9 below.

In some embodiments, the compound described herein e.g. a compound of Formula I, or a pharmaceutically acceptable salt or co-crystal thereof, has an $EC_{50}$ value in a suitable CD63 assay of less than or equal to 10 micromolar, such as 1 nM to 10 μM or 10 nM to 10 μM. In some embodiments, the compound or a pharmaceutically acceptable salt or co-crystal thereof, has an $EC_{50}$ value less than or equal to less than 1 micromolar, such as 1 nM to 1 μM or 10 nM to 1 μM. In some embodiments, the compound or a pharmaceutically acceptable salt or co-crystal thereof has an $EC_{50}$ value less than or equal to 500 nanomolar, such as 1 nM to 500 nM or 10 nM to 500 nM. In some embodiments, the compound or a pharmaceutically acceptable salt or co-crystal thereof has an $EC_{50}$ value less than or equal to 200 nanomolar, such as 1 nM to 200 nM or 10 nM to 200 nM. In some embodiments, the compound or a pharmaceutically acceptable salt or co-crystal thereof has an $EC_{50}$ value less than or equal to 150 nanomolar, such as 1 nM to 150 nM or 10 nM to 150 nM. In some embodiments, the compound or a pharmaceutically acceptable salt or co-crystal thereof has an $IC_{50}$ value less than or equal to 100 nanomolar, such as 1 nM to 100 nM or 10 nM to 100 nM. In some embodiments, the compound or a pharmaceutically acceptable salt or co-crystal thereof has an $EC_{50}$ value less than or equal to 75 nanomolar, such as 1 nM to 75 nM or 10 nM to 75 nM. In some embodiments, the $EC_{50}$ value is measured as described in the assay of Example 9.

The "kinetic solubility" refers to an assessment of the solubility of a compound in a suitable buffer, such as phosphate buffer at pH 7.4, at a given temperature, for example at 37° C. In one instance, kinetic solubility is measured at 37° C. in phosphate buffer at pH 7.4, such as by the assay as described in Example 10.

In some embodiments, the compounds described herein, e.g. a compound of Formula I, or a pharmaceutically acceptable salt or co-crystal thereof, has a kinetic solubility at 37° C. in phosphate buffer at pH 7.4 of greater than or equal to 10 μM, such as 10 μM to 500 μM or 10 μM to 250 μM. In some embodiments, the compound or a pharmaceutically acceptable salt or co-crystal thereof has a kinetic solubility at 37° C. in phosphate buffer at pH 7.4 of greater than or equal to 20 μM, such as 20 μM to 500 μM or 20 μM to 250 μM. In some embodiments, the compound or a pharmaceutically acceptable salt or co-crystal thereof has a kinetic solubility at 37° C. in phosphate buffer at pH 7.4 of greater than or equal to 30 μM, such as 30 μM to 500 μM or 30 μM to 250 μM. In some embodiments, the compound or a pharmaceutically acceptable salt or co-crystal thereof has a kinetic solubility at 37° C. in phosphate buffer at pH 7.4 of greater than or equal to 40 μM, such as 40 μM to 500 μM or 40 μM to 250 μM. In some embodiments, the compound or a pharmaceutically acceptable salt or co-crystal thereof has a kinetic solubility at 37° C. in phosphate buffer at pH 7.4 of greater than or equal to 50 μM, such as 50 μM to 500 μM or 50 μM to 250 μM. In some embodiments, the compound or a pharmaceutically acceptable salt or co-crystal thereof has a kinetic solubility at 37° C. in phosphate buffer at pH 7.4 of greater than or equal to 60 μM, such as 60 μM to 500 μM or 60 μM to 250 μM. In some embodiments, the compound or a pharmaceutically acceptable salt or co-crystal thereof has a kinetic solubility at 37° C. in phosphate buffer at pH 7.4 of greater than or equal to 70 μM, such as 70 μM to 500 μM or 70 μM to 250 μM. In some embodiments, the compound or a pharmaceutically acceptable salt or co-crystal thereof has a kinetic solubility at 37° C. in phosphate buffer at pH 7.4 of greater than or equal to 80 μM, such as 80 μM to 500 μM or 80 μM to 250 μM. In some embodiments, the compound or a pharmaceutically acceptable salt or co-crystal thereof has a kinetic solubility at 37° C. in phosphate buffer at pH 7.4 of greater than or equal to 90 μM, such as 90 μM to 500 μM or 90 μM to 250 μM. In some embodiments, the kinetic solubility is measured by the assay as described in Example 10.

The "human hepatocyte stability" is a measure of the stability of the compounds to metabolism by human hepatocytes, and is assessed as the predicted hepatic plasma clearance of the compounds in L/hr/kg. The predicted hepatocyte clearance can be measured, for example, by the assay described in Example 11.

In some embodiments, the compounds described herein, e.g. a compound of Formula I or of Formula II has a predicted hepatic plasma clearance of less than or equal to 0.50 L/hr/kg, such as 0.005 L/hr/kg to 0.50 L/hr/kg or 0.01 L/hr/kg to 0.50 L/hr/kg. In some embodiments, the compound has a predicted hepatic plasma clearance of less than or equal to 0.40 L/hr/kg, such as 0.005 L/hr/kg to 0.40 L/hr/kg or 0.01 L/hr/kg to 0.40 L/hr/kg. In some embodiments, the compound has a predicted hepatic plasma clearance of less than or equal to 0.30 L/hr/kg, such as 0.005 L/hr/kg to 0.30 L/hr/kg or 0.01 L/hr/kg to 0.30 L/hr/kg. In some embodiments, the compound has a predicted hepatic plasma clearance of less than or equal to 0.20 L/hr/kg, such as 0.005 L/hr/kg to 0.20 L/hr/kg or 0.01 L/hr/kg to 0.20 L/hr/kg. In some embodiments, the compound has a predicted hepatic plasma clearance of less than or equal to 0.10 L/hr/kg, such as 0.005 L/hr/kg to 0.10 L/hr/kg or 0.01 L/hr/kg to 0.10 L/hr/kg. In some embodiments, the compound has a predicted hepatic plasma clearance of less than or equal to 0.09 L/hr/kg, such as 0.005 L/hr/kg to 0.09 L/hr/kg or 0.01 L/hr/kg to 0.09 L/hr/kg. In some embodiments, the compound has a predicted hepatic plasma clearance of less than or equal to 0.08 L/hr/kg, such as 0.005 L/hr/kg to 0.08 L/hr/kg or 0.01 L/hr/kg to 0.08 L/hr/kg. In some embodiments, the compound has a predicted hepatic plasma clearance of less than or equal to 0.07 L/hr/kg, such as 0.005 L/hr/kg to 0.07 L/hr/kg or 0.01 L/hr/kg to 0.07 L/hr/kg. In some embodiments, the compound has a predicted hepatic plasma clearance of or less than or equal to 0.06 L/hr/kg, such as 0.005 L/hr/kg to 0.06 L/hr/kg or 0.01 L/hr/kg to 0.06 L/hr/kg. In some embodiments, the predicted hepatocyte clearance is measured by the assay described in Example 11.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p<0.05$.

A "disease responsive to inhibition of Syk activity" is a disease in which inhibiting Syk kinase provides a therapeutic benefit such as an amelioration of symptoms, decrease in disease progression, delay of disease onset, or inhibition of aberrant activity of certain cell-types (monocytes, B-cells, and mast cells).

"Subject" refers to an animal, such as a mammal, that has been or will be the object of treatment, observation or experiment. The methods described herein may be useful in both human therapy and veterinary applications. In some embodiments, the subject is a mammal; in some embodiments the subject is human; and in some embodiments the subject is chosen from cats and dogs. "Subject in need thereof" or "human in need thereof" refers to a subject, such as a human, who may have or is suspected to have diseases or conditions that would benefit from certain treatment; for example treatment with a compound of Formula I, or a pharmaceutically acceptable salt or co-crystal thereof, as described herein. This includes a subject who may be determined to be at risk of or susceptible to such diseases or conditions, such that treatment would prevent the disease or condition from developing.

"Treatment" or "treating" is an approach for obtaining beneficial or desired results including clinical results. Beneficial or desired clinical results may include one or more of the following:

(i) inhibiting the disease or condition (e.g., decreasing one or more symptoms resulting from the disease or condition, and/or diminishing the extent of the disease or condition);

(ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

In many cases, the compounds of this disclosure are capable of forming acid and/or base salts by virtue of the presence of amino and/or carboxyl groups or groups similar thereto.

"Pharmaceutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesulfonate (besylate), p-toluenesulfonate (tosylate), 2-hydroxyethylsulfonate, benzoate, salicylate, stearate, and alkanoate (such as acetate, $HOOC-(CH_2)_n-COOH$ where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

The compound of Formula I or the compound of Formula II can also be a pharmaceutically acceptable co-crystal or a co-crystal salt. The "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method. The terms co-crystal (or cocrystal) or co-crystal salt also refer to a multicomponent system in which there exists a host API (active pharmaceutical ingredient) molecule or molecules, such as a compound of Formula I, and a guest (or co-former) molecule or molecules. In particular embodiments said pharmaceutically acceptable co-crystal of the compound of Formula I or of the compound of Formula II with a co-former molecule is in a crystalline form selected from a malonic acid co-crystal, a succinic acid co-crystal, a decanoic acid co-crystal, a salicylic acid co-crystal, a vanillic acid co-crystal, a maltol co-crystal, or a glycolic acid co-crystal. Co-crystals may have improved properties as compared to the parent form (i.e., the free molecule, zwitter ion, etc.) or a salt of the parent compound. Improved properties can include increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like.

The term "crystal forms" and related terms herein refer to the various crystalline modifications of a given substance, including, but not limited to, polymorphs, solvates, hydrates, co-crystals, and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

As used herein, "pharmaceutically acceptable excipient" is a pharmaceutically acceptable vehicle that includes, without limitation, any and all carriers, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "carrier" refers to an excipient or vehicle that includes without limitation diluents, disintegrants, precipitation inhibitors, surfactants, glidants, binders, lubricants, and the like with which the compound is administered. Carriers are generally described herein and also in "Remington's Pharmaceutical Sciences" by E.W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term "diluent" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent from a supersaturated solution. One example of a precipitation inhibitor includes hydroxypropylmethylcellulose (HPMC).

The term "surfactants" generally refers to a substance that lowers the surface tension between a liquid and a solid that could improve the wetting of the active agent or improve the solubility of the active agent. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, and ethyl cellulose.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

Compounds

Compounds are provided here and elsewhere throughout, such as in the Summary and in the Examples.

The compounds provided herein are named using ChemBioDraw Ultra 12.0, and one skilled in the art understands that the compound structure may be named or identified using other commonly recognized nomenclature systems and symbols including CAS and IUPAC.

In some embodiments of the compound of Formula I, or a pharmaceutically acceptable salt or co-crystal thereof, $R^2$ is H. In some embodiments of the compound of Formula I, or a pharmaceutically acceptable salt or co-crystal thereof, $R^2$ is 2-hydroxyethoxyl.

In some embodiments of the compound of Formula I, or a pharmaceutically acceptable salt or co-crystal thereof, $R^3$ is H. In some embodiments of the compound of Formula I, or a pharmaceutically acceptable salt or co-crystal thereof, $R^3$ is methyl.

In some embodiments of the compound of Formula I, or a pharmaceutically acceptable salt or co-crystal thereof, $R^4$ is H or methyl. In some embodiments of the compound of Formula I, or a pharmaceutically acceptable salt or co-crystal thereof, $R^4$ is H. In some embodiments of the compound of Formula I, or a pharmaceutically acceptable salt or co-crystal thereof, $R^4$ is methyl.

In some embodiments of the compound of Formula I, or a pharmaceutically acceptable salt thereof, $R^1$ is selected from the group consisting of

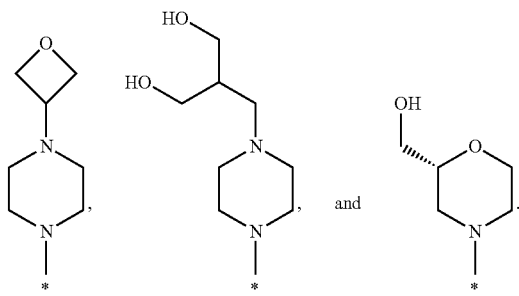

In some embodiments, $R^1$ is

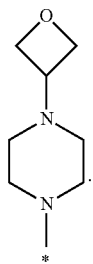

In some embodiments, $R^1$ is

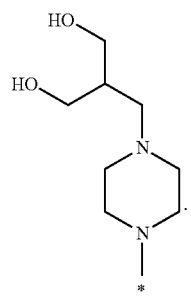

In some embodiments, $R^1$ is

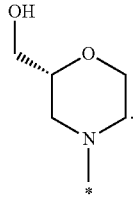

In some embodiments, $R^1$ is

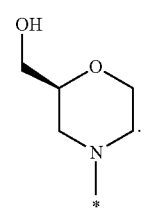

Separate embodiments herein, each providing a compound of Formula I, or a pharmaceutically acceptable salt or co-crystal thereof, in which $R^1$ is selected from the group consisting of

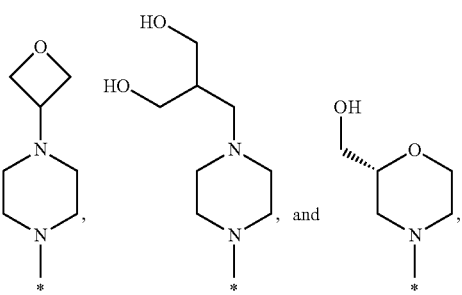

include embodiments A-1 through A-27 wherein $R^2$, $R^3$, and $R^4$ are as defined in Table A for each of the embodiments.

TABLE A

| Embodiment No. | $R^1$ selected from | $R^2$ | $R^3$ | $R^4$ |
|---|---|---|---|---|
| A-1 | 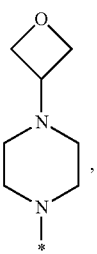 | H or 2-hydroxyethoxyl | H or methyl | H or methyl |
| A-2 | 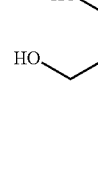 | H or 2-hydroxyethoxyl | H | H or methyl |

TABLE A-continued
| Embodiment No. | R¹ selected from | R² | R³ | R⁴ |
|---|---|---|---|---|
| A-3 | 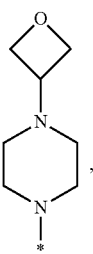, 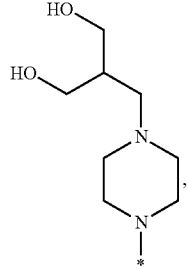, and 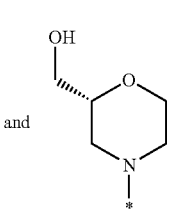 | H or 2-hydroxyethoxyl | methyl | H or methyl |
| A-4 | 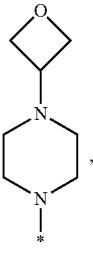, 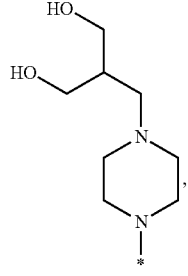, and 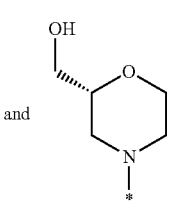 | H or 2-hydroxyethoxyl | H or methyl | H |
| A-5 | 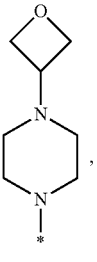, 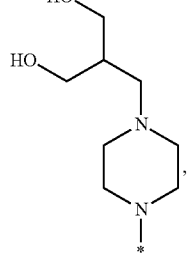, and 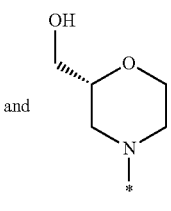 | H or 2-hydroxyethoxyl | H or methyl | Methyl |
| A-6 | 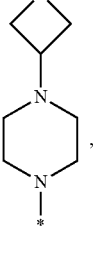, 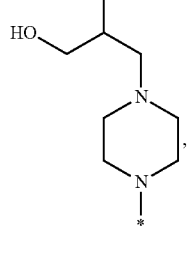, and 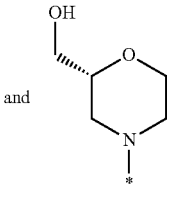 | H or 2-hydroxyethoxyl | H | H |
| A-7 | 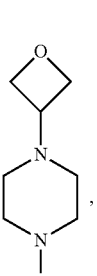, 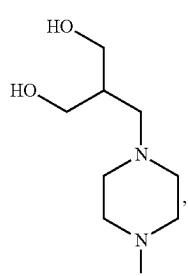, and 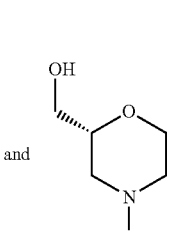 | H or 2-hydroxyethoxyl | H | methyl |

TABLE A-continued
| Embodiment No. | R¹ selected from | R² | R³ | R⁴ |
|---|---|---|---|---|
| A-8 | 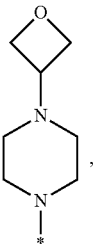 | H or 2-hydroxyethoxyl | methyl | H |
| A-9 | 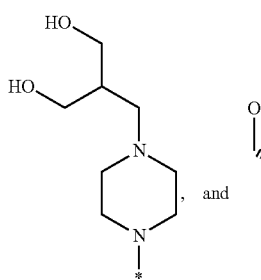 | H or 2-hydroxyethoxyl | methyl | methyl |
| A-10 | 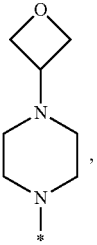 | H | H or methyl | H or methyl |
| A-11 | 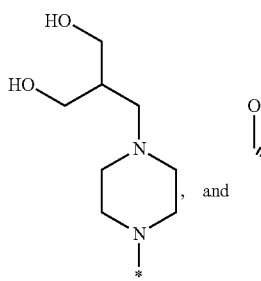 | H | H | H or methyl |
| A-12 | 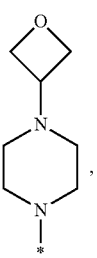 | H | methyl | H or methyl |

TABLE A-continued
| Embodiment No. | R¹ selected from | R² | R³ | R⁴ |
|---|---|---|---|---|
| A-13 | 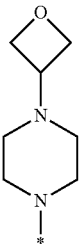, 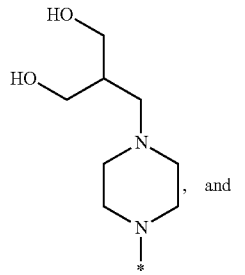, and 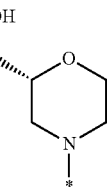 | H | H or methyl | H |
| A-14 | 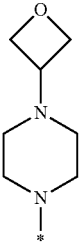, 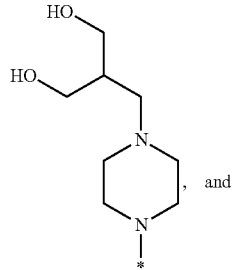, and 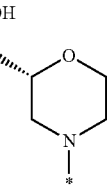 | H | H or methyl | methyl |
| A-15 | 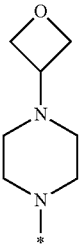, 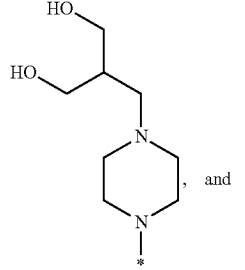, and 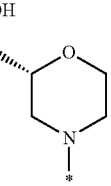 | H | H | H |
| A-16 | 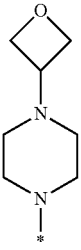, 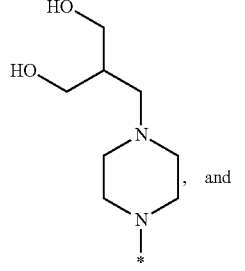, and 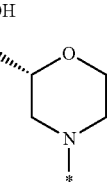 | H | methyl | H |
| A-17 | 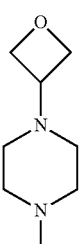, 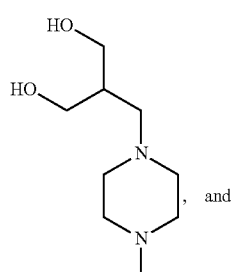, and 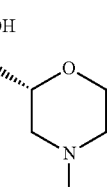 | H | H | methyl |

TABLE A-continued
| Embodiment No. | R¹ selected from | R² | R³ | R⁴ |
|---|---|---|---|---|
| A-18 | 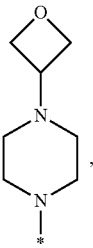, 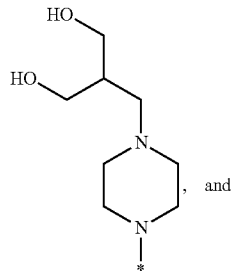, and 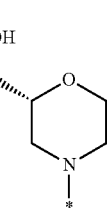 | H | methyl | methyl |
| A-19 | 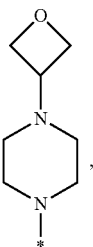, 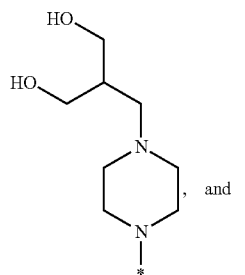, and 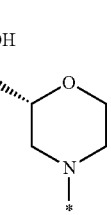 | 2-hydroxyethoxyl | H or methyl | H or methyl |
| A-20 | 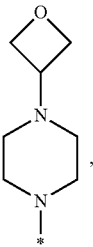, 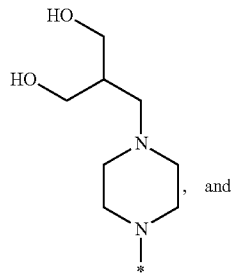, and 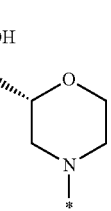 | 2-hydroxyethoxyl | H | H or methyl |
| A-21 | 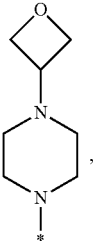, 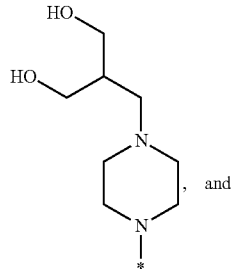, and 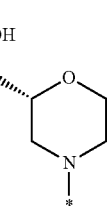 | 2-hydroxyethoxyl | methyl | H or methyl |
| A-22 | 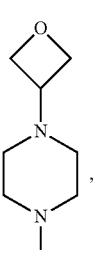, 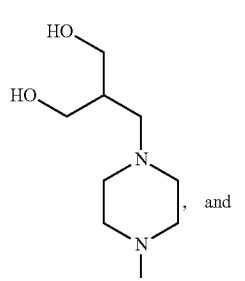, and 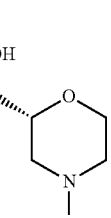 | 2-hydroxyethoxyl | H or methyl | H |

TABLE A-continued
| Embodiment No. | R¹ selected from | R² | R³ | R⁴ |
|---|---|---|---|---|
| A-23 | 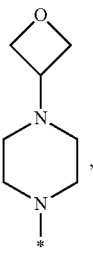 | 2-hydroxyethoxyl | H or methyl | methyl |
| A-24 | 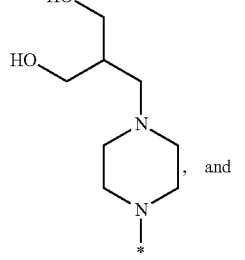 | 2-hydroxyethoxyl | H | H |
| A-25 | 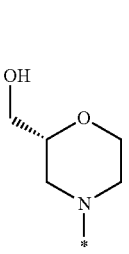 | 2-hydroxyethoxyl | methyl | H |
| A-26 | 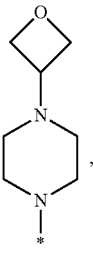 | 2-hydroxyethoxyl | H | methyl |
| A-27 | 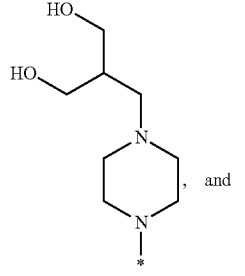 | 2-hydroxyethoxyl | methyl | methyl |

Separate embodiments herein, each providing a compound of Formula I, or a pharmaceutically acceptable salt or co-crystal thereof, in which R¹ is

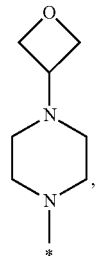

include embodiments B-1 through B-27 wherein R², R³, and R⁴ are as defined in Table B for each of the embodiments.

TABLE B

| Embodiment No. | R¹ | R² | R³ | R⁴ |
|---|---|---|---|---|
| B-1 | | H or 2-hydroxyethoxyl | H or methyl | H or methyl |
| B-2 | | H or 2-hydroxyethoxyl | H | H or methyl |
| B-3 | | H or 2-hydroxyethoxyl | methyl | H or methyl |
| B-4 | | H or 2-hydroxyethoxyl | H or methyl | H |

TABLE B-continued

| Embodiment No. | R¹ | R² | R³ | R⁴ |
|---|---|---|---|---|
| B-5 | oxetanyl-piperazine | H or 2-hydroxyethoxyl | H or methyl | Methyl |
| B-6 | oxetanyl-piperazine | H or 2-hydroxyethoxyl | H | H |
| B-7 | oxetanyl-piperazine | H or 2-hydroxyethoxyl | H | methyl |
| B-8 | oxetanyl-piperazine | H or 2-hydroxyethoxyl | methyl | H |
| B-9 | oxetanyl-piperazine | H or 2-hydroxyethoxyl | methyl | methyl |
| B-10 | oxetanyl-piperazine | H | H or methyl | H or methyl |

TABLE B-continued
| Embodiment No. | R[1] | R[2] | R[3] | R[4] |
|---|---|---|---|---|
| B-11 | 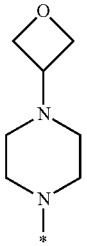 | H | H | H or methyl |
| B-12 | 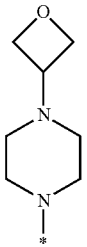 | H | methyl | H or methyl |
| B-13 | 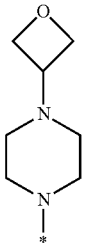 | H | H or methyl | H |
| B-14 | 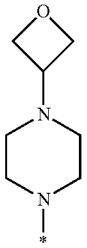 | H | H or methyl | methyl |
| B-15 | 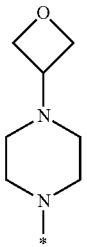 | H | H | H |
| B-16 | 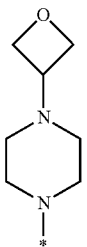 | H | methyl | H |

TABLE B-continued

| Embodiment No. | R¹ | R² | R³ | R⁴ |
| --- | --- | --- | --- | --- |
| B-17 | oxetan-3-yl-piperazinyl | H | H | methyl |
| B-18 | oxetan-3-yl-piperazinyl | H | methyl | methyl |
| B-19 | oxetan-3-yl-piperazinyl | 2-hydroxyethoxyl | H or methyl | H or methyl |
| B-20 | oxetan-3-yl-piperazinyl | 2-hydroxyethoxyl | H | H or methyl |
| B-21 | oxetan-3-yl-piperazinyl | 2-hydroxyethoxyl | methyl | H or methyl |
| B-22 | oxetan-3-yl-piperazinyl | 2-hydroxyethoxyl | H or methyl | H |

TABLE B-continued
| Embodiment No. | R¹ | R² | R³ | R⁴ |
|---|---|---|---|---|
| B-23 | 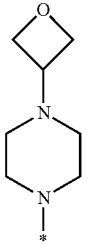 | 2-hydroxyethoxyl | H or methyl | methyl |
| B-24 | 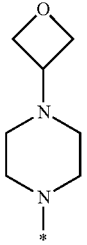 | 2-hydroxyethoxyl | H | H |
| B-25 | 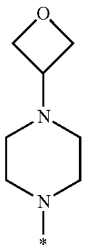 | 2-hydroxyethoxyl | methyl | H |
| B-26 | 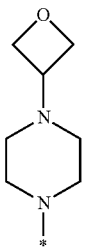 | 2-hydroxyethoxyl | H | methyl |
| B-27 | 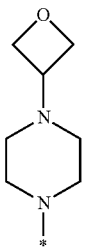 | 2-hydroxyethoxyl | methyl | methyl |

Separate embodiments herein, each providing a compound of Formula I, or a pharmaceutically acceptable salt or co-crystal thereof, in which $R^1$ is

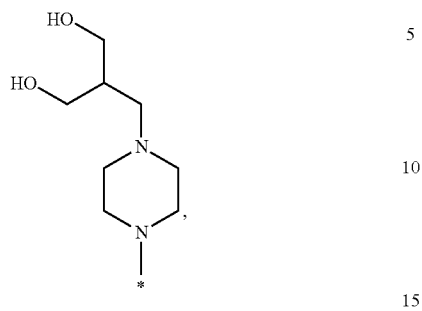

include embodiments C-1 through C-27 wherein $R^2$, $R^3$, and $R^4$ are as defined in Table C for each of the embodiments.

TABLE C

| Embodiment No. | $R^1$ | $R^2$ | $R^3$ | $R^4$ |
|---|---|---|---|---|
| C-1 | HO, HO, N–N–* (piperazine with dihydroxymethyl propyl) | H or 2-hydroxyethoxyl | H or methyl | H or methyl |
| C-2 | HO, HO, N–N–* | H or 2-hydroxyethoxyl | H | H or methyl |
| C-3 | HO, HO, N–N–* | H or 2-hydroxyethoxyl | methyl | H or methyl |
| C-4 | HO, HO, N–N–* | H or 2-hydroxyethoxyl | H or methyl | H |

TABLE C-continued

| Embodiment No. | R¹ | R² | R³ | R⁴ |
|---|---|---|---|---|
| C-5 | HO-CH2-CH(CH2-OH)-CH2-N(piperazine)-* | H or 2-hydroxyethoxyl | H or methyl | Methyl |
| C-6 | HO-CH2-CH(CH2-OH)-CH2-N(piperazine)-* | H or 2-hydroxyethoxyl | H | H |
| C-7 | HO-CH2-CH(CH2-OH)-CH2-N(piperazine)-* | H or 2-hydroxyethoxyl | H | methyl |
| C-8 | HO-CH2-CH(CH2-OH)-CH2-N(piperazine)-* | H or 2-hydroxyethoxyl | methyl | H |
| C-9 | HO-CH2-CH(CH2-OH)-CH2-N(piperazine)-* | H or 2-hydroxyethoxyl | methyl | methyl |

TABLE C-continued

| Embodiment No. | R¹ | R² | R³ | R⁴ |
| --- | --- | --- | --- | --- |
| C-10 | HO-CH₂-CH(CH₂-OH)-CH₂-piperazine-* | H | H or methyl | H or methyl |
| C-11 | HO-CH₂-CH(CH₂-OH)-CH₂-piperazine-* | H | H | H or methyl |
| C-12 | HO-CH₂-CH(CH₂-OH)-CH₂-piperazine-* | H | methyl | H or methyl |
| C-13 | HO-CH₂-CH(CH₂-OH)-CH₂-piperazine-* | H | H or methyl | H |
| C-14 | HO-CH₂-CH(CH₂-OH)-CH₂-piperazine-* | H | H or methyl | methyl |

TABLE C-continued

| Embodiment No. | R¹ | R² | R³ | R⁴ |
| --- | --- | --- | --- | --- |
| C-15 | HO−, HO− substituted CH with CH₂-piperazinyl (N* attachment) | H | H | H |
| C-16 | HO−, HO− substituted CH with CH₂-piperazinyl (N* attachment) | H | methyl | H |
| C-17 | HO−, HO− substituted CH with CH₂-piperazinyl (N* attachment) | H | H | methyl |
| C-18 | HO−, HO− substituted CH with CH₂-piperazinyl (N* attachment) | H | methyl | methyl |
| C-19 | HO−, HO− substituted CH with CH₂-piperazinyl (N* attachment) | 2-hydroxyethoxyl | H or methyl | H or methyl |

TABLE C-continued

| Embodiment No. | R¹ | R² | R³ | R⁴ |
| --- | --- | --- | --- | --- |
| C-20 | HO-CH₂-CH(CH₂-OH)-CH₂-piperazine-* | 2-hydroxyethoxyl | H | H or methyl |
| C-21 | HO-CH₂-CH(CH₂-OH)-CH₂-piperazine-* | 2-hydroxyethoxyl | methyl | H or methyl |
| C-22 | HO-CH₂-CH(CH₂-OH)-CH₂-piperazine-* | 2-hydroxyethoxyl | H or methyl | H |
| C-23 | HO-CH₂-CH(CH₂-OH)-CH₂-piperazine-* | 2-hydroxyethoxyl | H or methyl | methyl |
| C-24 | HO-CH₂-CH(CH₂-OH)-CH₂-piperazine-* | 2-hydroxyethoxyl | H | H |

TABLE C-continued

| Embodiment No. | R¹ | R² | R³ | R⁴ |
|---|---|---|---|---|
| C-25 | HO-CH2-C(CH2OH)-CH2-piperazine-* | 2-hydroxyethoxyl | methyl | H |
| C-26 | HO-CH2-C(CH2OH)-CH2-piperazine-* | 2-hydroxyethoxyl | H | methyl |
| C-27 | HO-CH2-C(CH2OH)-CH2-piperazine-* | 2-hydroxyethoxyl | methyl | methyl |

Separate embodiments herein, each providing a compound of Formula I, or a pharmaceutically acceptable salt or co-crystal thereof, in which R¹ is

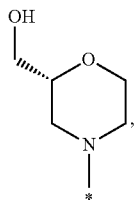

include embodiments D-1 through D-27 wherein R², R³, and R⁴ are as defined in Table D for each of the embodiments.

TABLE D

| Embodiment No. | R¹ | R² | R³ | R⁴ |
|---|---|---|---|---|
| D-1 | OH-CH2-morpholine-* | H or 2-hydroxyethoxyl | H or methyl | H or methyl |
| D-2 | OH-CH2-morpholine-* | H or 2-hydroxyethoxyl | H | H or methyl |
| D-3 | OH-CH2-morpholine-* | H or 2-hydroxyethoxyl | methyl | H or methyl |
| D-4 | OH-CH2-morpholine-* | H or 2-hydroxyethoxyl | H or methyl | H |

TABLE D-continued

| Embodiment No. | R¹ | R² | R³ | R⁴ |
|---|---|---|---|---|
| D-5 | OH, (S)-morpholin-2-ylmethyl | H or 2-hydroxyethoxyl | H or methyl | Methyl |
| D-6 | OH, (S)-morpholin-2-ylmethyl | H or 2-hydroxyethoxyl | H | H |
| D-7 | OH, (S)-morpholin-2-ylmethyl | H or 2-hydroxyethoxyl | H | methyl |
| D-8 | OH, (S)-morpholin-2-ylmethyl | H or 2-hydroxyethoxyl | methyl | H |
| D-9 | OH, (S)-morpholin-2-ylmethyl | H or 2-hydroxyethoxyl | methyl | methyl |
| D-10 | OH, (S)-morpholin-2-ylmethyl | H | H or methyl | H or methyl |
| D-11 | OH, (S)-morpholin-2-ylmethyl | H | H | H or methyl |
| D-12 | OH, (S)-morpholin-2-ylmethyl | H | methyl | H or methyl |
| D-13 | OH, (S)-morpholin-2-ylmethyl | H | H or methyl | H |
| D-14 | OH, (S)-morpholin-2-ylmethyl | H | H or methyl | methyl |
| D-15 | OH, (S)-morpholin-2-ylmethyl | H | H | H |
| D-16 | OH, (S)-morpholin-2-ylmethyl | H | methyl | H |
| D-17 | OH, (S)-morpholin-2-ylmethyl | H | H | methyl |
| D-18 | OH, (S)-morpholin-2-ylmethyl | H | methyl | methyl |
| D-19 | OH, (S)-morpholin-2-ylmethyl | 2-hydroxyethoxyl | H or methyl | H or methyl |

TABLE D-continued

| Embodiment No. | R¹ | R² | R³ | R⁴ |
|---|---|---|---|---|
| D-20 | OH, morpholine structure | 2-hydroxyethoxyl | H | H or methyl |
| D-21 | OH, morpholine structure | 2-hydroxyethoxyl | methyl | H or methyl |
| D-22 | OH, morpholine structure | 2-hydroxyethoxyl | H or methyl | H |
| D-23 | OH, morpholine structure | 2-hydroxyethoxyl | H or methyl | methyl |
| D-24 | OH, morpholine structure | 2-hydroxyethoxyl | H | H |
| D-25 | OH, morpholine structure | 2-hydroxyethoxyl | methyl | H |
| D-26 | OH, morpholine structure | 2-hydroxyethoxyl | H | methyl |
| D-27 | OH, morpholine structure | 2-hydroxyethoxyl | methyl | methyl |

Embodiments herein that refer to the compound of Formula I or of Formula II in one aspect also refer to a pharmaceutically acceptable salt or co-crystal of the compound of Formula I or of Formula II, even if not explicitly stated as such.

Also provided herein is a compound of Formula II:

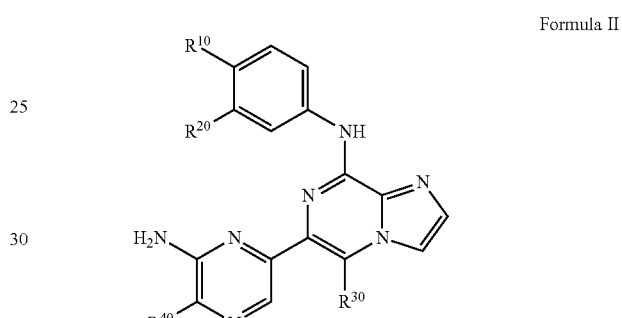

Formula II or a pharmaceutically acceptable salt, pharmaceutically acceptable co-crystal, pharmaceutically acceptable ester, stereoisomer, mixture of stereoisomers or tautomer thereof, wherein:

$R^{10}$ is selected from the group consisting of

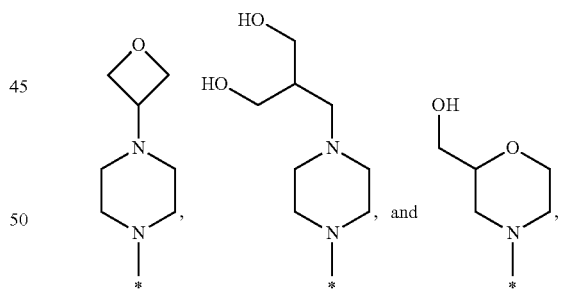

wherein * indicates the carbon atom of the indicated phenyl ring of Formula II to which $R^1$ is attached;

$R^{20}$ is H or 2-hydroxyethoxyl;

$R^{30}$ is H or methyl; and $R^{40}$ is H, halogen (i.e. F, Cl, Br, or I), methyl, or halo substituted methyl (i.e. methyl wherein 1 to 3 hydrogen atoms are substituted by 1 to 3 halogen atoms, which may be the same or different, e.g. fluoromethyl, chloromethyl, difluoromethyl, dichloromethyl, chlorofluoromethyl, trifluoromethyl, and the like).

In some embodiments of the compound of Formula II, or a pharmaceutically acceptable salt thereof, $R^{10}$ is selected from the group consisting of In some embodiments, $R^{10}$ is

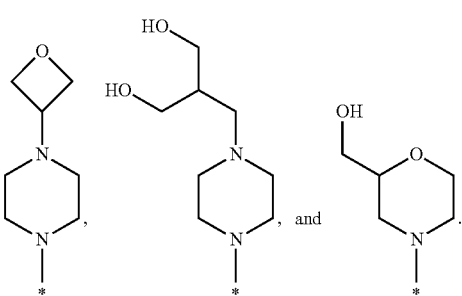

In some embodiments, $R^{10}$ is

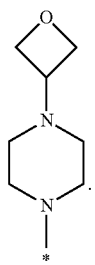

In some embodiments, $R^{10}$ is

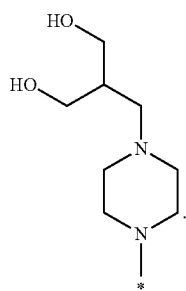

In some embodiments, $R^{10}$ is

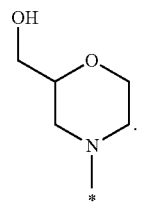

Within each of the embodiments described herein comprising a compound of Formula II, there is a further embodiment wherein each of $R^{20}$, $R^{30}$, and $R^{40}$ is H. Within each of the embodiments described herein comprising a compound of Formula II, there is a another embodiment wherein $R^{20}$ is H, $R^{31}$ is methyl, and $R^{40}$ is H. Within each of the embodiments described herein comprising a compound of Formula II, there is also another embodiment wherein $R^{20}$ is H, $R^{30}$ is H, and $R^{40}$ is methyl. Within each of the embodiments described herein comprising a compound of Formula II, there is still another embodiment wherein $R^{20}$ is 2-hydroxyethoxyl, $R^{30}$ is methyl, and $R^{40}$ is H. Within each of the embodiments described herein comprising a compound of Formula II, there is still another embodiment wherein $R^{20}$ is 2-hydroxyethoxyl, $R^{30}$ is methyl, and $R^{40}$ is H. Within each of the embodiments described herein comprising a compound of Formula II, there is still further embodiment wherein $R^{20}$ is 2-hydroxyethoxyl, $R^{30}$ is H, and $R^{40}$ is methyl.

Representative compounds of the invention are listed in Table A below. The compounds in Table A are named using ChemBioDraw Ultra 12.0 and it should be understood that other names be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). Any ambiguity in naming of compounds can be resolved by deferring to the structure, where provided.

TABLE A

| Representative Compounds | |
|---|---|
| Structure | Name |
|  | 6-(6-amino-5-methylpyrazin-2-yl)-N-(4-(4-(oxetan-3-yl)piperazin-1-yl)phenyl)imidazo[1,2-a]pyrazin-8-amine |

TABLE A-continued

Representative Compounds

| Structure | Name |
|---|---|
| 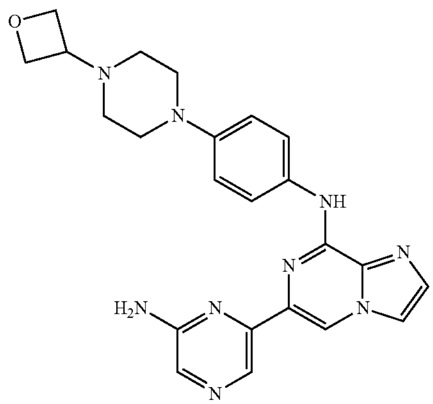 [SMILES: Nc1cncc(-c2cn3ccnc3c(Nc3ccc(N4CCN(C5COC5)CC4)cc3)n2)n1] | 6-(6-aminopyrazin-2-yl)-N-(4-(4-(oxetan-3-yl)piperazin-1-yl)phenyl)imidazo[1,2-a]pyrazin-8-amine |
| 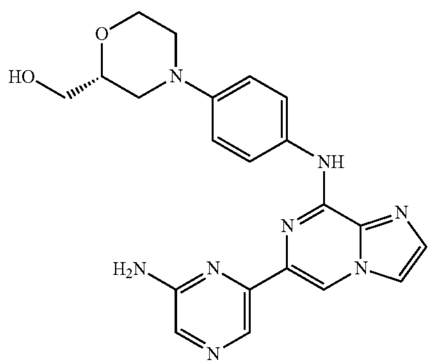 [SMILES: Nc1cncc(-c2cn3ccnc3c(Nc3ccc(N4CCO[C@@H](CO)C4)cc3)n2)n1] | (R)-(4-(4-((6-(6-aminopyrazin-2-yl)imidazo[1,2-a]pyrazin-8-yl)amino)phenyl)morpholin-2-yl)methanol |
| 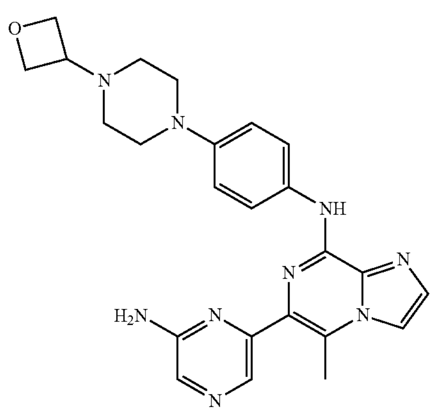 [SMILES: Cc1c(-c2cncc(N)n2)nc(Nc2ccc(N3CCN(C4COC4)CC3)cc2)c2nccn12] | 6-(6-aminopyrazin-2-yl)-5-methyl-N-(4-(4-(oxetan-3-yl)piperazin-1-yl)phenyl)imidazo[1,2-a]pyrazin-8-amine |
| 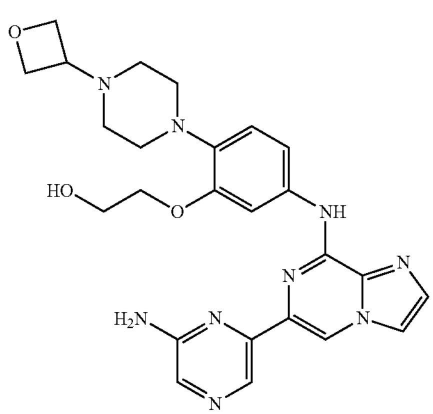 [SMILES: Nc1cncc(-c2cn3ccnc3c(Nc3ccc(N4CCN(C5COC5)CC4)c(OCCO)c3)n2)n1] | 2-(5-((6-(6-aminopyrazin-2-yl)imidazo[1,2-a]pyrazin-8-yl)amino)-2-(4-(oxetan-3-yl)piperazin-1-yl)phenoxy)ethanol |

TABLE A-continued

Representative Compounds

| Structure | Name |
|---|---|
| 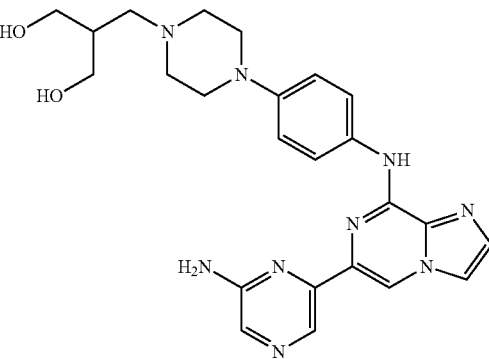 [SMILES: Nc1cncc(-c2cn3ccnc3c(Nc3ccc(N4CCN(CC(CO)CO)CC4)cc3)n2)n1] | 2-((4-(4-(((6-(6-aminopyrazin-2-yl)imidazo[1,2-a]pyrazin-8-yl)amino)phenyl)piperazin-1-yl)methyl)propane-1,3-diol |
| 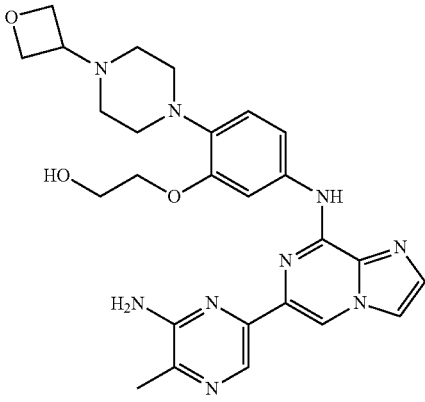 [SMILES: Cc1ncc(-c2cn3ccnc3c(Nc3ccc(N4CCN(C5COC5)CC4)c(OCCO)c3)n2)nc1N] | 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol |

An embodiment the invention provides 6-(6-aminopyrazin-2-yl)-N-(4-(4-(oxetan-3-yl)piperazin-1-yl)phenyl)imidazo[1,2-a]pyrazin-8-amine, pharmaceutically acceptable salts, pharmaceutically acceptable co-crystals, pharmaceutically acceptable esters, pharmaceutically acceptable solvates, hydrates, enantiomers, mixture of enantiomers, tautomers, polymorphs, and pharmaceutically acceptable prodrugs thereof. An embodiment of the invention provides 6-(6-aminopyrazin-2-yl)-N-(4-(4-(oxetan-3-yl)piperazin-1-yl)phenyl)imidazo[1,2-a]pyrazin-8-amine or a pharmaceutically acceptable salt or co-crystal thereof. An embodiment the invention provides 6-(6-aminopyrazin-2-yl)-N-(4-(4-(oxetan-3-yl)piperazin-1-yl)phenyl)imidazo[1,2-a]pyrazin-8-amine or a pharmaceutically acceptable salt thereof.

The invention provides 6-(6-aminopyrazin-2-yl)-N-(4-(4-(oxetan-3-yl)piperazin-1-yl)phenyl)imidazo[1,2-a]pyrazin-8-amine mesylate, for example 6-(6-aminopyrazin-2-yl)-N-(4-(4-(oxetan-3-yl)piperazin-1-yl)phenyl)imidazo[1,2-a]pyrazin-8-amine monomesylate. For example, the invention provides 6-(6-aminopyrazin-2-yl)-N-(4-(4-(oxetan-3-yl)piperazin-1-yl)phenyl)imidazo[1,2-a]pyrazin-8-amine monomesylate Form I, which may be characterized by XRPD peaks at about 19.7, about 17.3, about 17.9, about 21.6, and about 25.8 (2 theta degrees). Also provided is 6-(6-aminopyrazin-2-yl)-N-(4-(4-(oxetan-3-yl)piperazin-1-yl)phenyl)imidazo[1,2-a]pyrazin-8-amine monomesylate Form II, which may be characterized by XRPD peaks at about 17.3, about 25.1, about 20.4, about 19.6 and about 18.5 (2 theta degrees).

An embodiment of the present invention provides 6-(6-aminopyrazin-2-yl)-N-(4-(4-(oxetan-3-yl)piperazin-1-yl)phenyl)imidazo[1,2-a]pyrazin-8-amine succinate. For example the invention provides 6-(6-aminopyrazin-2-yl)-N-(4-(4-(oxetan-3-yl)piperazin-1-yl)phenyl)imidazo[1,2-a]pyrazin-8-amine succinate Form I, which may be characterized by XRPD peaks at about 16.5, about 24.5, about 17.7, about 28.4 and about 21.8 (2 theta degrees). The invention also provides 6-(6-aminopyrazin-2-yl)-N-(4-(4-(oxetan-3-yl)piperazin-1-yl)phenyl)imidazo[1,2-a]pyrazin-8-amine succinate Form II, which may be characterized by XRPD peaks at about 25.0, about 16.3, about 22.0, about 7.9, and about 7.6 (2 theta degrees).

The term "about" as used in relation to XRPD peaks means, for example, ±0.2, ±0.1, ±0.05 (2 theta degrees) etc.

The compounds described herein, e.g. a compound of Formula I, or a pharmaceutically acceptable salt or co-crystal thereof, or a compound of Formula II, or a pharmaceutically acceptable salt or co-crystal thereof, provide distinct advantages as Syk inhibitors. The compounds described herein are inhibitors of Syk kinase activity, as measured, for example, as the inhibition of Syk kinase activity in a biochemical assay or as the reduction in basophil activation as measured by CD63 expression, as described in the Examples. The compounds described herein also have desirable properties for use as a pharmaceutical, including kinetic solubility at 37° C. in phosphate buffer at pH 7.4 and low levels of hepatocyte clearance. These features result in Syk inhibitors for treatment of disease with pharmacokinetic characteristics that provide a therapeutic window such that the compounds can be effective in smaller doses than currently known compounds. As such, the compounds provide effective doses with minimal off target activity, which may reduce unwanted side effects, lessen the chance of drug-drug interactions, and increase a subject's compliance with a given therapeutic regimen.

In some embodiments, the compounds described herein, e.g. a compound of Formula I, or a pharmaceutically acceptable salt or co-crystal thereof, or a compound of Formula II, or a pharmaceutically acceptable salt or co-crystal thereof, is effective in one or more of Syk kinase activity inhibition or reduction of basophil activation as measured by CD63 expression, for example, the compound inhibits Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 12; and/or reduces CD63 expression activity with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 9.

In some embodiments, the compound of Formula I, or a pharmaceutically acceptable salt or co-crystal thereof, is effective in both of Syk kinase inhibition and reduction of CD63 expression, for example, the compound has Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 12; and has reduction in CD63 expression with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 9.

In some embodiments, in addition to having the property of one or more of Syk kinase inhibition or reduction of basophil activation as measured by CD63 expression, including having both of the properties of Syk kinase inhibition and reduction of basophil activation as measured by CD63 expression, the compound of Formula I, or a pharmaceutically acceptable salt or co-crystal thereof, has desirable properties for use as a pharmaceutical, including one or more of kinetic solubility and low levels of hepatocyte clearance. In some embodiments, the compound of Formula I, or a pharmaceutically acceptable salt or co-crystal thereof, has a desirable property of one or more of kinetic solubility and low levels of hepatocyte clearance, including kinetic solubility at 37° C. in phosphate buffer at pH 7.4 of greater than or equal to 10 µM, greater than or equal to 20 µM, greater than or equal to 30 µM, greater than or equal to 40 µM, greater than or equal to 50 µM, greater than or equal to 60 µM, greater than or equal to 70 µM, greater than or equal to 80 µM, or greater than or equal to 90 µM, as demonstrated by a suitable measure of kinetic solubility, such as the assay as described in Example 10; and/or predicted hepatocyte clearance of less than or equal to 0.50 L/hr/kg, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11.

In some embodiments, the compound of Formula I, or a pharmaceutically acceptable salt or co-crystal thereof, has a desirable property of kinetic solubility, and low levels of hepatocyte clearance, including kinetic solubility at 37° C. in phosphate buffer at pH 7.4 of greater than or equal to 10 µM, greater than or equal to 20 µM, greater than or equal to 30 µM, greater than or equal to 40 µM, greater than or equal to 50 µM, greater than or equal to 60 µM, greater than or equal to 70 µM, greater than or equal to 80 µM, or greater than or equal to 90 µM, as demonstrated by a suitable measure of kinetic solubility, such as the assay as described in Example 10; and predicted hepatocyte clearance of less than or equal to 0.50 L/hr/kg, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11.

In some embodiments, the compound of Formula I, or a pharmaceutically acceptable salt or co-crystal thereof, is effective in both of Syk kinase inhibition and reduction of CD63 expression, and has a desirable property of kinetic solubility, and low levels of hepatocyte clearance, for example, the compound has Syk kinase activity with an $IC_{50}$ value less than or equal to 1 micromolar, less than or equal to 500 nanomolar, less than or equal to 200 nanomolar, less than or equal to 100 nanomolar, less than or equal to 50 nanomolar, less than or equal to 20 nanomolar, or less than or equal to 10 nanomolar, as demonstrated by a suitable assay for Syk kinase activity, such as the assay as described in Example 12; and has reduced CD63 expression with an $EC_{50}$ value less than or equal to 1 micromolar, less than or equal to 500 nanomolar, less than or equal to 200 nanomolar, less than or equal to 150 nanomolar, less than or equal to 100 nanomolar, or less than or equal to 75 nanomolar, as demonstrated by a suitable assay for the measurement of CD63 expression in basophils, such as the assay as described in Example 10; and kinetic solubility at 37° C. in phosphate buffer at pH 7.4 of greater than or equal to 10 µM, greater than or equal to 20 µM, greater than or equal to 30 µM, greater than or equal to 40 µM, greater than or equal to 50 µM, greater than or equal to 60 µM, greater than or equal to 70 µM, greater than or equal to 80 µM, or greater than or equal to 90 µM, as demonstrated by a suitable measure of kinetic solubility, such as the assay as described in Example 10; and predicted hepatocyte clearance of less than or equal to 0.50 L/hr/kg, less than or equal to 0.40 L/hr/kg, less than or equal to 0.30 L/hr/kg, less than or equal to 0.20 L/hr/kg, less than or equal to 0.10 L/hr/kg, less than or equal to 0.09 L/hr/kg, less than or equal to 0.08 L/hr/kg, less than or equal to 0.07 L/hr/kg, or less than or equal to 0.06 L/hr/kg, as demonstrated by a suitable measure of predicted hepatocyte clearance, such as the assay as described in Example 11.

Methods of Use

The invention provides a compound of Formula I, or a pharmaceutically acceptable salt or co-crystal thereof, for use in therapy. Provided is a method of treating a subject, for example, a mammal, such as a human, having a disease responsive to inhibition of Syk activity, comprising administrating to the subject having, or suspected of having, such a disease, an effective amount of a compound of Formula I, or a pharmaceutically acceptable salt or co-crystal thereof. In one aspect, the subject, such as a human, is administered a pharmaceutical composition comprising a compound of Formula I, or a pharmaceutically acceptable salt or co-crystal thereof, and a pharmaceutically acceptable vehicle. The invention further provides a compound of Formula I, or a pharmaceutically acceptable salt or co-crystal thereof for use in such methods.

In some embodiments, the compound of Formula I, or a pharmaceutically acceptable salt or co-crystal thereof, may be administered to a subject (e.g., a human) who is at risk or has a family history of the disease or condition.

In some embodiments, the compound of Formula I, or a pharmaceutically acceptable salt or co-crystal thereof, may also inhibit other kinases, such that disease, disease symptoms, and conditions associated with these kinases are also treated.

Methods of treatment also include inhibiting Syk activity and/or inhibiting B-cell activity, by inhibiting ATP binding or hydrolysis by Syk or by some other mechanism, in vivo, in a subject suffering from a disease responsive to inhibition of Syk activity, by administering an effective concentration of a compound of Formula I, or a pharmaceutically acceptable salt or co-crystal thereof. An example of an effective concentration would be that concentration sufficient to inhibit Syk activity in vitro. An effective concentration may be ascertained experimentally, for example by assaying blood concentration of the compound following administration to a human, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of inhibiting B-cell activity in a subject in need thereof comprising administering an effective amount of a compound of Formula I, or a pharmaceutically acceptable salt or co-crystal thereof.

Also provided is a method of inhibiting B-cell proliferation in a subject in need thereof comprising administering an effective amount of a compound of Formula I, or a pharmaceutically acceptable salt or co-crystal thereof.

Also provided is a method of treating a subject having cancer, an allergic disorder and/or an autoimmune and/or inflammatory disease, and/or an acute inflammatory reaction, by administering an effective amount of a compound of Formula I, or a pharmaceutically acceptable salt or co-crystal thereof.

In some embodiments, the conditions and diseases that can be treated using a compound of Formula I, or a pharmaceutically acceptable salt or co-crystal thereof, include, but are not limited tolymphoma (e.g. small lymphocytic lymphoma (SLL), non-Hodgkin's lymphoma (NHL), indolent non-Hodgkin's lymphoma (iNHL), refractory iNHL, mantle cell lymphoma (MCL), follicular lymphoma (FL), lymphoplasmacytic lymphoma (LPL), marginal zone lymphoma (MZL), immunoblastic large cell lymphoma, lymphoblastic lymphoma, Splenic marginal zone B-cell lymphoma (+/-villous lymphocytes), Nodal marginal zone lymphoma (+/-monocytoid B-cells), Extranodal marginal zone B-cell lymphoma of mucosa-associated lymphoid tissue (MALT) type, T-cell lymphoma (e.g. cutaneous T-cell lymphoma, extranodal T-cell lymphoma, anaplastic large cell lymphoma, angioimmunoblastic T-cell lymphoma, mycosis fungoides), B-cell lymphoma, diffuse large B-cell lymphoma (DLBCL), Mediastinal large B-cell lymphoma, Intravascular large B-cell lymphoma, Primary effusion lymphoma, small non-cleaved cell lymphoma, or Burkitt's lymphoma), multiple myeloma, plasmacytoma, and leukemia (e.g. acute lymphocytic leukemia (ALL), T-cell acute lymphoblastic leukemia (T-ALL), B-cell acute lymphoblastic leukemia (B-ALL), B-cell prolymphocytic leukemia, acute myeloid leukemia (AML), chronic lymphocytic leukemia (CLL), juvenile myelomonocytic leukemia (JMML), minimal residual disease (MRD), hairy cell leukemia, myelofibrosis (e.g. primary or secondary myelofibrosis), or chronic myeloid leukemia (CML), myelodysplastic syndrome (MDS), myeloproliferative disease (MPD), Waldestrom's macroglobulinemia (WM), polycythemia vera, essential thrombocythemia, pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, ACTH-producing tumors, systemic lupus erythematosus (SLE), myestenia gravis, Goodpasture's syndrome, glomerulonephritis, hemorrhage, pulmonary hemorrhage, atherosclerosis, rheumatoid arthritis (RA), psoriatic arthritis, monoarticular arthritis, osteoarthritis, gouty arthritis, spondylitis, Beheet disease, autoimmune thyroiditis, Reynaud's syndrome, acute disseminated encephalomyelitis, chronic idiopathic thrombocytopenic purpura, multiple sclerosis (MS), Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, inflammatory bowel disease (e.g. chronic inflammatory bowel disease, ulcerative colitis, Crohn's disease, necrotizing enterocolitis), irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuloma, eczema, chronic bronchitis, acute respiratory distress syndrome, allergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, alcoholic hepatitis, gastritis, enteritis, contact dermatitis, atopic dermatitis, gingivitis, appendicitis, pancreatitis, cholocystitis, and polycystic kidney disease.

In some embodiments, provided is a method of treating a subject having an allergic disorder and/or an autoimmune and/or inflammatory disease, and/or an acute inflammatory reaction by administering an effective amount of a compound of Formula I, or a pharmaceutically acceptable salt or co-crystal thereof. In some embodiments, the disease is selected from the group consisting of systemic lupus erythematosus, myestenia gravis, Goodpasture's syndrome, glomerulonephritis, hemorrhage, pulmonary hemorrhage, atherosclerosis, rheumatoid arthritis, psoriatic arthritis, monoarticular arthritis, osteoarthritis, gouty arthritis, spondylitis, Beheet disease, autoimmune thyroiditis, Reynaud's syndrome, acute disseminated encephalomyelitis, chronic idiopathic thrombocytopenic purpura, multiple sclerosis, Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, chronic inflammatory bowel disease, ulcerative colitis, Crohn's disease, necrotizing enterocolitis, irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuloma, eczema, chronic bronchitis, acute respiratory distress syndrome, allergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, alcoholic hepatitis, gastritis, enteritis, contact dermatitis, atopic dermatitis, gingivitis, appendicitis, pancreatitis, cholocystitis, and polycystic kidney disease.

In some embodiments, provided is a method of treating a subject having an autoimmune disease selected from the group consisting of a systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease by administering an effective amount of a compound of Formula I, or a pharmaceutically acceptable salt or co-crystal thereof. In some embodiments, the autoimmune disease has excessive or destructive immune reactions, such as asthma, rheumatoid arthritis, multiple sclerosis, chronic obstructive pulmonary disease, or systemic lupus erythematosus.

In some embodiments, provided is a method of treating a subject having rheumatoid arthritis, by administering an effective amount of a compound of Formula I, or a pharmaceutically acceptable salt or co-crystal thereof.

Syk is a known inhibitor of apoptosis in lymphoma B-cells. Defective apoptosis contributes to the pathogenesis and drug resistance of human leukemias and lymphomas.

Thus, further provided is a method of promoting or inducing apoptosis in cells expressing Syk comprising contacting the cell with a compound of Formula I, or a pharmaceutically acceptable salt or co-crystal thereof.

In some embodiments, provided is a method of treating a subject having cancer selected from the group consisting of carcinoma, sarcoma, melanoma, lymphoma and leukemia. In some embodiments the cancer is a solid tumor or a hematologic malignancy.

In some embodiments, provided is a method of treating a subject having a hematologic malignancy selected from the group consisting of small lymphocytic lymphoma, non-Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/−villous lymphocytes), Nodal marginal zone lymphoma (+/−monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldestrom's macroglobulinemia.

In some embodiments, provided is a method of treating a subject having cancer, wherein the cancer is leukemia or lymphoma, by administering an effective amount of a compound of Formula I, or a pharmaceutically acceptable salt or co-crystal thereof. In some embodiments, the cancer is selected from the group consisting of acute lymphocytic leukemia, acute myeloid leukemia, chronic lymphocytic leukemia, small lymphocytic lymphoma, myelodysplastic syndrome, myeloproliferative disease, chronic myeloid leukemia, multiple myeloma, indolent non-Hodgkin's lymphoma, refractory iNHL, non-Hodgkin's lymphoma, mantle cell lymphoma, follicular lymphoma, Waldestrom's macroglobulinemia, T-cell lymphoma, B-cell lymphoma, and diffuse large B-cell lymphoma. In one embodiment, the cancer is T-cell acute lymphoblastic leukemia, or B-cell acute lymphoblastic leukemia. The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt's lymphoma, diffuse large B-cell lymphoma and mantle cell lymphoma. In one embodiment, the cancer is indolent non-Hodgkin's lymphoma.

In some embodiments, provided is a method of treating a subject having a hematologic malignancy by administering an effective amount of a compound of Formula I, or a pharmaceutically acceptable salt or co-crystal thereof. In specific embodiments, the hematologic malignancy is leukemia (e.g., chronic lymphocytic leukemia) or lymphoma (e.g., non-Hodgkin's lymphoma).

In some embodiments, provided is a method of treating a subject having chronic lymphocytic leukemia by administering an effective amount of a compound of Formula I, or a pharmaceutically acceptable salt or co-crystal thereof.

In some embodiments, provided is a method of treating a subject having a solid tumor by administering an effective amount of a compound of Formula I, or a pharmaceutically acceptable salt or co-crystal thereof. In some embodiments, the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas. Kaposi's sarcomas, myxoid carcinoma, round cell carcinoma, squamous cell carcinomas, esophageal squamous cell carcinomas, oral carcinomas, cancers of the adrenal cortex, and ACTH-producing tumors. In some embodiments, the solid tumor is from non-small cell lung cancer, small-cell lung cancer, colon cancer, CNS cancer, melanoma, ovarian cancer, renal cancer, prostate cancer, and breast cancer.

Also provided herein is a compound as described herein, e.g. a compound of Formula I, or a pharmaceutically acceptable salt or co-crystal thereof, for use in the treatment of a disease or condition as described herein, e.g. a cancer (including carcinoma, sarcoma, melanoma, lymphoma and leukemia), an allergic disorder and/or an autoimmune and/or inflammatory disease, and/or an acute inflammatory reaction. Also provided herein is a compound of formula I, or a pharmaceutically acceptable salt or co-crystal thereof, for use in a method of treatment described in this disclosure.

Also provided herein is a compound as described herein, e.g. a compound of Formula I, or a pharmaceutically acceptable salt or co-crystal thereof, for use in the manufacture of a medicament for the treatment of a disease or condition as described herein, e.g. a cancer (including carcinoma, sarcoma, melanoma, lymphoma and leukemia), an allergic disorder and/or an autoimmune and/or inflammatory disease, and/or an acute inflammatory reaction.

Subjects

Any of the methods of treatment provided may be used to treat a subject who has been diagnosed with or is suspected of having an allergic disorder and/or an autoimmune and/or inflammatory disease, and/or an acute inflammatory reaction or a cancer.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, the compound of Formula I, or a pharmaceutically acceptable salt or co-crystal thereof, administered before, during, or after administration of chemotherapy, radiotherapy, immunotherapy, and/or surgery.

In another aspect, provided herein are methods for treating a subject (e.g., a human) who is "refractory" to a cancer treatment or who is in "relapse" after treatment for cancer (e.g., a hematologic malignancy). A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g. after a treatment has shown effective reduction in the cancer, such as after a subject is in remission or partial remission.

In some embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapies (including, for example, standard or experimental chemotherapies).

In some embodiments, the subject is refractory to at least one, at least two, at least three, or at least four anti-cancer therapies (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab;

temsirolimus and Velcade*; Iodine-131 tositumomab (Bexxar*) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); D.T. PACE (dexamethasone, thalidomide, cisplatin, Adriamycin*, cyclophosphamide, etoposide); and idelalisib.

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" Hematology 2006, p. 285-294. Lymphoma incidence patterns in the United States is profiled in Morton, L. M., et al. "Lymphoma Incidence Patterns by WHO Subtype in the United States, 1992-2001" Blood 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A combination of Rituximab and chemotherapy agents is especially effective. A modified approach is radioimmunotherapy, wherein a monoclonal antibody is combined with a radioisotope particle, such as Iodine-131 tositumomab (Bexxar*) and Yttrium-90 ibritumomab tiuxetan (Zevalin*). In another example, Bexxar* is used in sequential treatment with CHOP. Another immunotherapy example includes using cancer vaccines, which is based upon the genetic makeup of an individual subject's tumor. A lymphoma vaccine example is GTOP-99 (MyVax*). Yet other approaches to treating mantle cell lymphoma includes autologous stem cell transplantation coupled with high-dose chemotherapy, or treating mantle cell lymphoma includes administering proteasome inhibitors, such as Velcade* (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan*, Velcade* or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, lenalidomide (Revlimid*, CC-5013), and Geldanamycin (17-AAG).

Examples of other therapeutic agents used to treat Waldenstrom's Macroglobulinemia (WM) include perifosine, bortezomib (Velcade*), rituximab, sildenafil citrate (Viagra*), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant ft3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody C19, monoclonal antibody CD20, omega-3 fatty acids, mitoxantrone hydrochloride, octreotide acetate, tositumomab and iodine 1-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (Blood 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include idelalisib (Zydelig®), Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin*, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a compound of Formula I, or a pharmaceutically acceptable salt or co-crystal thereof, or a pharmaceutical composition thereof, to the subject. A subject who is sensitized is a subject who is responsive to the treatment involving administration of the compound of Formula I, or a pharmaceutically acceptable salt or co-crystal thereof, or who has not developed resistance to such treatment.

In another aspect, provided herein are methods for treating a subject (e.g., a human) for a cancer, with comorbidity, wherein the treatment is also effective in treating the comorbidity. A "comorbidity" to cancer is a disease that occurs at the same time as the cancer.

In some embodiments, provided herein are methods for treating a subject (e.g., a human) for chronic lymphocytic leukemia (CLL), with comorbidity, wherein the treatment is also effective in treating the comorbidity. Many subjects with CLL will have one or more other diseases, for example diseases affecting the blood pressure system, vascular and heart systems, endocrine and metabolic systems, genitourinary system, musculoskeletal system, respiratory system, neurological system, upper and lower gastrointestinal systems, psychiatric system, ear, nose and throat systems, renal system, or liver system. Specific morbidities of CLL include, but are not limited to, one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis (Satram-Hoang et al., *Journal of Cancer Therapy,* 2013; 4:1321-1329; Thurmes et al., *Leukemia & Lymphoma,* 2008; 49(1):49-56).

In some embodiments, a method of treating a comorbidity of CLL in a subject (e.g., a human), wherein the method comprises administering a compound of Formula I, or a pharmaceutically acceptable salt or co-crystal thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Monotherapy and Combination Therapies

Also provided are methods of treatment in which a compound of Formula I, or a pharmaceutically acceptable salt or co-crystal thereof, is the only active agent given to a subject and also includes methods of treatment in which a compound of Formula I, or a pharmaceutically acceptable salt or co-crystal thereof, is given to a subject in combination with one or more additional active agents. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof an effective amount of a compound of Formula I, or a pharmaceutically acceptable salt or co-crystal thereof, wherein the subject is not undergoing therapy for the same disease or condition with another agent or procedure.

In some embodiments where the compound of Formula I, or a pharmaceutically acceptable salt or co-crystal thereof, is administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapies (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof, (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of the compound of Formula I, or a pharmaceutically acceptable salt or co-crystal thereof, as a monotherapy).

It should be understood that when a subject (e.g. a human) is treated with the compound of Formula I, or a pharmaceutically acceptable salt or co-crystal thereof, as a monotherapy, the subject may also undergo one or more other therapies that are not anti-cancer therapies.

In some embodiments, a method of treating a comorbidity of a cancer, including but not limited to CLL, in a subject (e.g., a human) who has been diagnosed with cancer, e.g. CLL, wherein the method comprises administering a therapy to treat the comorbidity in combination with a compound of Formula I, or a pharmaceutically acceptable salt or co-crystal thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Combination Therapies

In some embodiments, a method of treating cancer, an allergic disorder and/or an autoimmune and/or inflammatory disease, and/or an acute inflammatory reaction comprises administering to a subject in need thereof an effective amount of a compound of Formula I, or a pharmaceutically acceptable salt or co-crystal thereof, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of Formula I, or a pharmaceutically acceptable salt or co-crystal thereof. In some embodiments, a compound of Formula I, or a pharmaceutically acceptable salt or co-crystal thereof is combined with another active agent in a single dosage form. In one embodiment, the invention provides a product comprising a compound of the Formula I, or a pharmaceutically acceptable salt or co-crystal thereof, and an additional therapeutic agent as a combined preparation for simultaneous, separate or sequential use in therapy, e.g. a method of treating a cancer, an allergic disorder and/or an autoimmune and/or inflammatory disease, and/or an acute inflammatory reaction.

Provided herein are also methods of treatment in which the compound of Formula I, or a pharmaceutically acceptable salt or co-crystal thereof, administered to a subject (e.g., a human) who has been diagnosed with or is suspected of having a cancer is given to the subject in combination with one or more additional therapies, including one or more of the anti-cancer therapies described above. Thus, in some embodiments, the method for treating cancer in a subject (e.g., a human) in need thereof, comprises administering to the subject a therapeutically effective amount of a compound of Formula I, or a pharmaceutically acceptable salt or co-crystal thereof, or a pharmaceutical composition thereof, together with one or more additional therapies, which can be useful for treating the cancer. The one or more additional therapies may involve the administration of one or more therapeutic agents. Suitable anti-cancer therapeutics that may be used in combination with a compound of Formula I, or a pharmaceutically acceptable salt or co-crystal thereof include, but are not limited to, one or more agents selected from the group consisting of chemotherapeutic agents (e.g. mitomycin C, carboplatin, taxol, cisplatin, paclitaxel, etoposide, doxorubicin), radiotherapeutic antitumor agents, topoisomerase I inhibitors (e.g. camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), PI3K inhibitors (e.g. compounds A, B, and C below), inhibitors of lysyl oxidase-like 2, and biological agents (e.g. antibodies such as anti CD20 antibody, IDEC 8, immunotoxins, and cytokines).

In some embodiments, the method for treating cancer in a subject (e.g., a human) in need thereof, comprises administering to the subject a therapeutically effective amount of a compound of Formula I, or a pharmaceutically acceptable salt or co-crystal thereof, or a pharmaceutical composition thereof with one or more additional therapies selected from the group consisting of fludarabine, rituximab, obinutuzumab, alemtuzumab, cyclophosphamide, chlorambucil, doxorubicin, doxorubicin hydrochloride, vincristine, vincristine sulfate, melphalan, busulfan, carmustine, prednisone, prednisolone, dexamethasone, methotrexate, cytarabine, mitoxantrone, mitoxantrone hydrochloride, bortezomib, temsirolimus, carboplatin, etoposide, thalidomide, cisplatin, lumiliximab, anti-TRAIL, bevacizumab, galiximab, epratuzumab, SGN-40, anti-CD74, ofatumumab, ha20, PRO131921, CHIR-12.12, apolizumab, milatuzumab, bevacizumab, yttrium-90-labeled ibritumomab tiuxetan, tositumomab, iodine-131 tositumomab, iphosphamide, GTOP-99 vaccine, oblimersen, Flavopiridol, PD0332991, R-roscovitine, Styryl sulphones, Obatoclax, TRAIL, Anti-TRAIL DR4 and DR5 antibodies, Everolimus, BMS-345541, Curcumin, Vorinostat, lenalidomide, Geldanamycin, perifosine, sildenafil citrate, CC-5103, simvastatin, enzastaurin, campath-1H, DT PACE, antineoplaston A10, antineoplaston AS2-1, beta alethine, filgrastim, recombinant interferon alfa, dolastatin 10, indium In 111 monoclonal antibody MN-14, anti-thymocyte globulin, cyclosporine, mycophenolate mofetil, therapeutic allogeneic lymphocytes, tacrolimus, thiotepa, paclitaxel, aldesleukin, docetaxel, ifosfamide, mesna, recombinant interleukin-12, recombinant interleukin-11, ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, octreotide acetate, motexafin gadolinium, arsenic trioxide, tipifarnib, autologous human tumor-derived HSPPC-96, veltuzumab, bryostatin 1, PEGylated liposomal hydrochloride, peripheral blood stem cell transplantation, autologous hematopoietic stem cell transplantation, autologous bone marrow transplantation, infusion of stem cells, bone marrow ablation with stem cell support, in vitro-treated peripheral blood stem cell transplantation, umbilical cord blood transplantation, low-LET cobalt-60 gamma ray therapy, bleomycin, conventional surgery, radiation therapy, and nonmyeloablative allogeneic hematopoietic stem cell transplantation.

In some embodiments, the one or more additional therapies involve the use of a phosphatidylinositol 3-kinase (PI3K) inhibitor, including for example, Compounds A, B or C, or a pharmaceutically acceptable salt of such compounds. The structures of Compounds A, B and C are provided below.

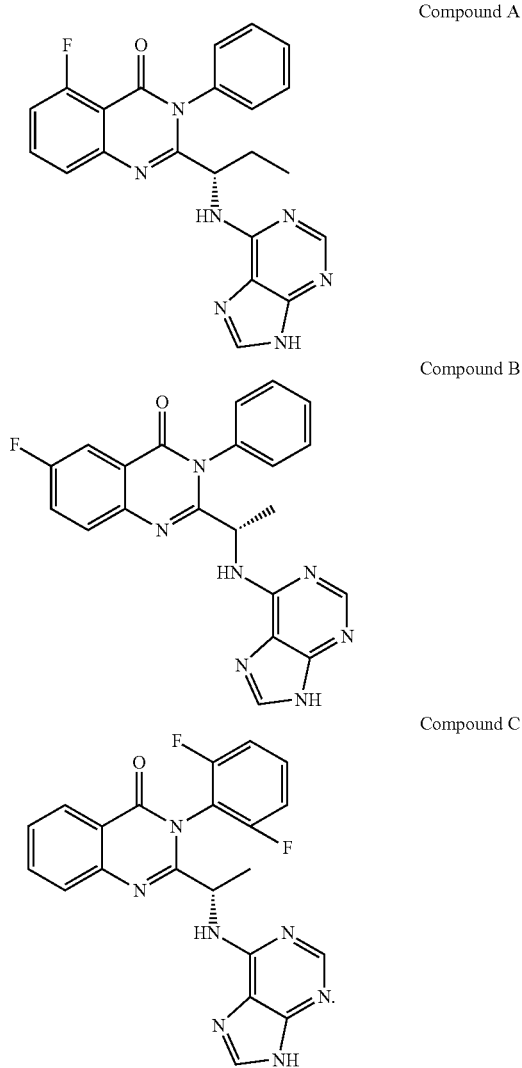

Compound A

Compound B

Compound C

In other embodiments of the methods described above involving the use of the compound of Formula I, or a pharmaceutically acceptable salt or co-crystal thereof, in combination with one or more additional therapies, the one or more additional therapies is other than a therapy using Compound A, Compound B, or Compound C, or a pharmaceutically acceptable salt of such compounds. In one embodiment of the methods described above involving the use of the compound of Formula I, or a pharmaceutically acceptable salt or co-crystal thereof, in combination with one or more additional therapies, the one or more additional therapies is other than a therapy using Compound A, or a pharmaceutically acceptable salt or co-crystal thereof. In another embodiment of the methods described above involving the use of the compound of Formula I, or a pharmaceutically acceptable salt or co-crystal thereof, in combination with one or more additional therapies, the one or more additional therapies is other than a therapy using Compound B, or a pharmaceutically acceptable salt or co-crystal thereof. In yet another embodiment of the methods described above involving the use of the compound of Formula I, or a pharmaceutically acceptable salt or co-crystal thereof, in combination with one or more additional therapies, the one or more additional therapies is other than a therapy using Compound C, or a pharmaceutically acceptable salt or co-crystal thereof.

In other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

The compound of Formula I, or a pharmaceutically acceptable salt or co-crystal thereof, can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with a compound of Formula I, or a pharmaceutically acceptable salt or co-crystal thereof, or a pharmaceutical composition thereof, in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase 11 inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines). In one embodiment of the method for increasing sensitivity of cancer cells to chemotherapy, the chemotherapeutic agent is other than Compound A, or a pharmaceutically acceptable salt or co-crystal thereof. In another embodiment of the method for increasing sensitivity of cancer cells to chemotherapy, the chemotherapeutic agent is other than Compound B, or a pharmaceutically acceptable salt or co-crystal thereof. In yet another embodiment of the method for increasing sensitivity of cancer cells to chemotherapy, the chemotherapeutic agent is other than Compound C, or a pharmaceutically acceptable salt or co-crystal thereof.

In some embodiments, the compound of Formula I, or a pharmaceutically acceptable salt or co-crystal thereof, or a pharmaceutical composition thereof, is used in combination with Rituxan® (Rituximab) or other agents that work by selectively depleting CD20+ B-cells.

Included herein are methods of treating cancer, an allergic disorder and/or an autoimmune and/or inflammatory disease, and/or an acute inflammatory reaction comprising administering to a subject in need thereof an effective amount of a compound of Formula I, or a pharmaceutically acceptable salt or co-crystal thereof, or a pharmaceutical composition thereof, in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

Provided herein are also methods of treatment in which the compound of Formula I, or a pharmaceutically acceptable salt or co-crystal thereof, administered to a subject (e.g., a human) who has been diagnosed with or is suspected of having an autoimmune disease is given to the subject in combination with one or more anti-inflammatory or immunosuppressant agents selected from the group consisting of ibuprofen, flurbiprofen, naproxen, naproxen sodium, diclofenac, diclofenac sodium, misoprostol, sulindac, oxaprozin, diflunisal, piroxicam, indomethacin, etodolac, fenoprofen calcium, ketoprofen, sodium nabumetone, sulfasalazine, tolmetin sodium, hydroxychloroquine, celecoxib, valdecoxib, lumiracoxib, etoricoxib, rofecoxib, acetylsalicylic acid, sodium salicylate, choline salicylate, magnesium salicylate, cortisone, dexamethasone, methylprednisolone, prednisolone, prednisolone sodium phosphate, prednisone, gold sodium thiomalate, auranofin, methotrexate, dihydroorotate leflunomide, leflunomide, cyclosporine, tacrolimus, azathioprine, mycophenolate mofetil, eculizumab, pexelizumab, entanercept, and infliximab.

It should be understood that any combinations of the additional therapeutic agents described above may be used, as if each and every combination was individually listed. For example, in some embodiments, the additional therapeutic agents include a PI3K inhibitor and a LOXL2 inhibitor.

Pharmaceutical Compositions and Administration Compounds of Formula I, or a pharmaceutically acceptable salt or co-crystal thereof, are usually administered in the form of pharmaceutical compositions. This disclosure therefore provides pharmaceutical compositions that contain, as the active ingredient, one or more of the compounds described, or a pharmaceutically acceptable salt, pharmaceutically acceptable co-crystal or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents.

Such compositions are prepared in a manner well known in the pharmaceutical art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of Formula I, or a pharmaceutically acceptable salt or co-crystal thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of the compound of Formula I, or a pharmaceutically acceptable salt or co-crystal thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound of Formula I, or a pharmaceutically acceptable salt or co-crystal thereof. Administration may be via capsule or enteric coated tablets, or the like. In making the pharmaceutical compositions that include the compound of Formula I, or a pharmaceutically acceptable salt or co-crystal thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions described herein are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 1 mg to about 5000 mg, about 1 mg to about 4000 mg, about 1 mg to about 3000 mg, about 1 mg to about 2000 mg, about 2 mg to about 2000 mg, about 5 mg to about 2000 mg, about 10 mg to about 2000 mg, about 1 mg to about 1000 mg, about 2 mg to about 1000 mg, about 5 mg to about 1000 mg, about 10 mg to about 1000 mg, about 25 mg to about 1000 mg, about 50 mg to about 1000 mg, about 75 mg to about 1000 mg, about 100 mg to about 1000 mg, about 125 mg to about 1000 mg, about 150 mg to about 1000 mg, about 175 mg to about 1000 mg, about 200 mg to about 1000 mg, about 225 mg to about 1000 mg, about 250 mg to about 1000 mg, about 300 mg to about 1000 mg, about 350 mg to about 1000 mg, about 400 mg to about 1000 mg, about 450 mg to about 1000 mg, about 500 mg to about 1000 mg, about 550 mg to about 1000 mg, about 600 mg to about 1000 mg, about 650 mg to about 1000 mg, about 700 mg to about 1000 mg, about 750 mg to about 1000 mg, about 800 mg to about 1000 mg, about 850 mg to about 1000 mg, about 900 mg to about 1000 mg, about 950 mg to about 1000 mg, about 1 mg to about 750 mg, about 2 mg to about 750 mg, about 5 mg to about 750 mg, about 10 mg to about 750 mg, about 25 mg to about 750 mg, about 50 mg to about 750 mg, about 75 mg to about 750 mg, about 100 mg to about 750 mg, about 125 mg to about 750 mg, about 150 mg to about 750 mg, about 175 mg to about 750 mg, about 200 mg to about 750 mg, about 225 mg to about 750 mg, about 250 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 1 mg to about 500 mg, about 2 mg to about 500 mg, about 5 mg to about 500 mg, about 10 mg to about 500 mg, about 25 mg to about 500 mg, about 50 mg to about 500 mg, about 75 mg to about 500 mg, about 100 mg to about 500 mg, about 125 mg to about 500 mg, about 150 mg to about 500 mg, about 175 mg to about 500 mg, about 200 mg to about 500 mg, about 225 mg to about 500 mg, about 250 mg to about 500 mg, about 300 mg to about 500 mg, about 350 mg to about 500 mg, about 400 mg to about 500 mg, about 450 mg to about 500 mg, about 1 mg to about 400 mg, about 2 mg to about 400 mg, about 5 mg to about 400 mg, about 10 mg to about 400 mg, about 25 mg to about 400 mg, about 50 mg to about 400 mg, about 75 mg to about 400 mg, about 100 mg to about 400 mg, about 125 mg to about 400 mg, about 150 mg to about 400 mg, about 175 mg to about 400 mg, about 200 mg to about 400 mg, about 225 mg to about 400 mg, about 250 mg to about 400 mg, about 300 mg to about 400 mg, about 350 mg to about 400 mg, about 1 mg to about 300 mg, about 2 mg to about 300 mg, about 5 mg to about 300 mg, about 10 mg to about 300 mg, about 25 mg to about 300 mg, about 50 mg to about 300 mg, about 75 mg to about 300 mg, about 100 mg to about 300 mg, about 125 mg to about 300 mg, about 150 mg to about 300 mg, about 175 mg to about 300 mg, about 200 mg to about 300 mg, about 225 mg to about 300 mg, about 250 mg to about 300 mg, about 1 mg to about 250 mg, about 2 mg to about 250 mg, about 5 mg to about 250 mg, about 10 mg to about 250 mg, about 25 mg to about 250 mg, about 50 mg to about 250 mg, about 75 mg to about 250 mg, about 100 mg to about 250 mg, about 125 mg to about 250 mg, about 150 mg to about 250 mg, about 175 mg to about 250 mg, about 200 mg to about 250 mg, about 225 mg to about 250 mg, about 1 mg to about 225 mg, about 2 mg to about 225 mg, about 5 mg to about 225 mg, about 10 mg to about 225 mg, about 25 mg to about 225 mg, about 50 mg to about 225 mg, about 75 mg to about 225 mg, about 100 mg to about 225 mg, about 125 mg to about 225 mg, about 150 mg to about 225 mg, about 175 mg to about 225 mg, about 200 mg to about 225 mg, about 1 mg to about 200 mg, about 2 mg to about 200 mg, about 5 mg to about 200 mg, about 10 mg to about 200 mg, about 25 mg to about 200 mg, about 50 mg to about 200 mg, about 75 mg to about 200 mg, about 100 mg to about 200 mg, about 125 mg to about 200 mg, about 150 mg to about 200 mg, about 175 mg to about 200 mg, about 1 mg to about 175 mg, about 2 mg to about 175 mg, about 5 mg to about 175 mg, about 10 mg to about 175 mg, about 25 mg to about 175 mg, about 50 mg to about 175 mg, about 75 mg to about 175 mg, about 100 mg to about 175 mg, about 125 mg to about 175 mg, about 150 mg to about 175 mg, about 1 mg to about 150 mg, about 2 mg to about 150 mg, about 5 mg to about 150 mg, about 10 mg to about 150 mg, about 25 mg to about 150 mg, about 50 mg to about 150 mg, about 75 mg to about 150 mg, about 100 mg to about 150 mg, about 125 mg to about 150 mg, about 1 mg to about 125 mg, about 2 mg to about 125 mg, about 5 mg to about 125 mg, about 10 mg to about 125 mg, about 25 mg to about 125 mg, about 50 mg to about 125 mg, about 75 mg to about 125 mg, about 100 mg to about 125 mg, about 1 mg to about 100 mg, about 2 mg to about 100 mg, about 5 mg to about 100 mg, about 10 mg to about 100 mg, about 25 mg to about 100 mg, about 50 mg to about 100 mg, or about 75 mg to about 100 mg of a compound of Formula I, about or a pharmaceutically acceptable salt or co-crystal thereof.

In some embodiments, for oral administration, each dosage unit contains about 1 mg, about 2 mg, about 5 mg, about 10 mg, about 15 mg, about 20 mg, about 25 mg, about 30 mg, about 35 mg, about 40 mg, about 45 mg, about 50 mg, about 75 mg, about 100 mg, about 125 mg, about 150 mg, about 175 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of a compound of Formula I, or a pharmaceutically acceptable salt or co-crystal thereof.

The dosages for oral administration described above may be administered once daily (QD) or twice daily (BID). In some embodiments, the compound of formula I, or a pharmaceutically acceptable salt or co-crystal thereof, or a pharmaceutical composition thereof, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 75 mg QD, about 100 mg QD, about 125 mg QD, about 150 mg QD, about 175 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments, the compound of formula I, or a pharmaceutically acceptable salt or co-crystal thereof, or a pharmaceutical composition thereof, is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

In some embodiments, for parenteral administration, each dosage unit contains from 0.1 mg to 1 g, 0.1 mg to 700 mg, or 0.1 mg to 100 mg of a compound of Formula I, or a pharmaceutically acceptable salt or co-crystal thereof.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of the compound of Formula I, or a pharmaceutically acceptable salt or co-crystal thereof. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions comprising the compound of Formula I, or a pharmaceutically acceptable salt or co-crystal thereof, may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing Regimen

In the methods provided herein, the compound of Formula I, or a pharmaceutically acceptable salt or co-crystal thereof, or a pharmaceutical composition thereof, is administered in a therapeutically effective amount to achieve its intended purpose. Determination of a therapeutically effective amount is well within the capability of those skilled in the art, especially in light of the detailed disclosure provided herein. In some embodiments (methods of treating cancer), a therapeutically effective amount of the compound of Formula I, or a pharmaceutically acceptable salt or co-crystal thereof, may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

The therapeutically effective amount may vary depending on the subject, and disease or condition being treated, the weight and age of the subject, the severity of the disease or condition, and the manner of administering, which can readily be determined by one or ordinary skill in the art.

The dosing regimen of the compound of Formula I, or a pharmaceutically acceptable salt or co-crystal thereof, in the methods provided herein may vary depending upon the indication, route of administration, and severity of the condition, for example. Depending on the route of administration, a suitable dose can be calculated according to body weight, body surface area, or organ size. The final dosing regimen is determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

The formulation and route of administration chosen may be tailored to the individual subject, the nature of the condition to be treated in the subject, and generally, the judgment of the attending practitioner. For example, the therapeutic index of the compound of Formula I, or a pharmaceutically acceptable salt or co-crystal thereof, may be enhanced by modifying or derivatizing the compound for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992).

The therapeutically effective amount of the compound of Formula I, or a pharmaceutically acceptable salt or co-crystal thereof, may be provided in a single dose or multiple doses to achieve the desired treatment endpoint. As used herein, "dose" refers to the total amount of an active ingredient (e.g., the compound of Formula I, or a pharmaceutically acceptable salt or co-crystal thereof,) to be taken each time by a subject (e.g., a human). The dose administered, for example for oral administration described above, may be administered once daily (QD), twice daily (BID), three times daily, four times daily, or more than four times daily. In some embodiments, the dose of a compound of Formula I, or a pharmaceutically acceptable salt or co-crystal thereof, is administered once daily. In some embodiments, the dose of a compound of Formula I, or a pharmaceutically acceptable salt or co-crystal thereof, is administered twice daily.

In some embodiments, exemplary doses of the compound of Formula I, or a pharmaceutically acceptable salt or co-crystal thereof, for a human subject may be from about 1 mg to about 5000 mg, about 1 mg to about 4000 mg, about 1 mg to about 3000 mg, about 1 mg to about 2000 mg, about 2 mg to about 2000 mg, about 5 mg to about 2000 mg, about 10 mg to about 2000 mg, about 1 mg to about 1000 mg, about 2 mg to about 1000 mg, about 5 mg to about 1000 mg, about 10 mg to about 1000 mg, about 25 mg to about 1000 mg, about 50 mg to about 1000 mg, about 75 mg to about 1000 mg, about 100 mg to about 1000 mg, about 125 mg to about 1000 mg, about 150 mg to about 1000 mg, about 175 mg to about 1000 mg, about 200 mg to about 1000 mg, about 225 mg to about 1000 mg, about 250 mg to about 1000 mg, about 300 mg to about 1000 mg, about 350 mg to about 1000 mg, about 400 mg to about 1000 mg, about 450 mg to about 1000 mg, about 500 mg to about 1000 mg, about 550 mg to about 1000 mg, about 600 mg to about 1000 mg, about 650 mg to about 1000 mg, about 700 mg to about 1000 mg, about 750 mg to about 1000 mg, about 800 mg to about 1000 mg, about 850 mg to about 1000 mg, about 900 mg to about 1000 mg, about 950 mg to about 1000 mg, about 1 mg to about 750 mg, about 2 mg to about 750 mg, about 5 mg to about 750 mg, about 10 mg to about 750 mg, about 25 mg to about 750 mg, about 50 mg to about 750 mg, about 75 mg to about 750 mg, about 100 mg to about 750 mg, about 125 mg to about 750 mg, about 150 mg to about 750 mg, about 175 mg to about 750 mg, about 200 mg to about 750 mg, about 225 mg to about 750 mg, about 250 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 1 mg to about 500 mg, about 2 mg to about 500 mg, about 5 mg to about 500 mg, about 10 mg to about 500 mg, about 25 mg to about 500 mg, about 50 mg to about 500 mg, about 75 mg to about 500 mg, about 100 mg to about 500 mg, about 125 mg to about 500 mg, about 150 mg to about 500 mg, about 175 mg to about 500 mg, about 200 mg to about 500 mg, about 225 mg to about 500 mg, about 250 mg to about 500 mg, about 300 mg to about 500 mg, about 350 mg to about 500 mg, about 400 mg to about 500 mg, about 450 mg to about 500 mg, about 1 mg to about 400 mg, about 2 mg to about 400 mg, about 5 mg to about 400 mg, about 10 mg to about 400 mg, about 25 mg to about 400 mg, about 50 mg to about 400 mg, about 75 mg to about 400 mg, about 100 mg to about 400 mg, about 125 mg to about 400 mg, about 150 mg to about 400 mg, about 175 mg to about 400 mg, about 200 mg to about 400 mg, about 225 mg to about 400 mg, about 250 mg to about 400 mg, about 300 mg to about 400 mg, about 350 mg to about 400 mg, about 1 mg to about 300 mg, about 2 mg to about 300 mg, about 5 mg to about 300 mg, about 10 mg to about 300 mg, about 25 mg to about 300 mg, about 50 mg to about 300 mg, about 75 mg to about 300 mg, about 100 mg to about 300 mg, about 125 mg to about 300 mg, about 150 mg to about 300 mg, about 175 mg to about 300 mg, about 200 mg to about 300 mg, about 225 mg to about 300 mg, about 250 mg to about 300 mg, about 1 mg to about 250 mg, about 2 mg to about 250 mg, about 5 mg to about 250 mg, about 10 mg to about 250 mg, about 25 mg to about 250 mg, about 50 mg to about 250 mg, about 75 mg to about 250 mg, about 100 mg to about 250 mg, about 125 mg to about 250 mg, about 150 mg to about 250 mg, about 175 mg to about 250 mg, about 200 mg to about 250 mg, about 225 mg to about 250 mg, about 1 mg to about 225 mg, about 2 mg to about 225 mg, about 5 mg to about 225 mg, about 10 mg to about 225 mg, about 25 mg to about 225 mg, about 50 mg to about 225 mg, about 75 mg to about 225 mg, about 100 mg to about 225 mg, about 125 mg to about 225 mg, about 150 mg to about 225 mg, about 175 mg to about 225 mg, about 200 mg to about 225 mg, about 1 mg to about 200 mg, about 2 mg to about 200 mg, about 5 mg to about 200 mg, about 10 mg to about 200 mg, about 25 mg to about 200 mg, about 50 mg to about 200 mg, about 75 mg to about 200 mg, about 100 mg to about 200 mg, about 125 mg to about 200 mg, about 150 mg to about 200 mg, about 175 mg to about 200 mg, about 1 mg to about 175 mg, about 2 mg to about 175 mg, about 5 mg to about 175 mg, about 10 mg to about 175 mg, about 25 mg to about 175 mg, about 50 mg to about 175 mg, about 75 mg to about 175 mg, about 100 mg to about 175 mg, about 125 mg to about 175 mg, about 150 mg to about 175 mg, about 1 mg to about 150 mg, about 2 mg to about 150 mg, about 5 mg to about 150 mg, about 10 mg to about 150 mg, about 25 mg to about 150 mg, about 50 mg to about 150 mg, about 75 mg to about 150 mg, about 100 mg to about 150 mg, about 125 mg to about 150 mg, about 1 mg to about 125 mg, about 2 mg to about 125 mg, about 5 mg to about 125 mg, about 10 mg to about 125 mg, about 25 mg to about 125 mg, about 50 mg to about 125 mg, about 75 mg to about 125 mg, about 100 mg to about 125 mg, about 1 mg to about 100 mg, about 2 mg to about 100 mg, about 5 mg to about 100 mg, about 10 mg to about 100 mg, about 25 mg to about 100 mg, about 50 mg to about 100 mg, or about 75 mg to about 100 mg.

In some embodiments, exemplary doses of the compound of Formula I, or a pharmaceutically acceptable salt or co-crystal thereof, for a human subject may be about 1 mg, about 2 mg, about 5 mg, about 10 mg, about 15 mg, about 20 mg, about 25 mg, about 30 mg, about 35 mg, about 40 mg, about 45 mg, about 50 mg, about 75 mg, about 100 mg, about 125 mg, about 150 mg, about 175 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1200 mg, about 1400 mg, about 1600 mg, about 1800 mg, about 2000 mg, about 2200 mg, about 2400 mg, about 2600 mg, about 2800 mg, about 3000 mg, about 3200 mg, about 3400 mg, about 3600 mg, about 3800 mg, about 4000 mg, about 4200 mg, about 4400 mg, about 4600 mg, about 4800 mg, or about 5000 mg.

In other embodiments, the methods provided comprise continuing to treat the subject (e.g., a human) by administering the doses of the compound of Formula I, or a pharmaceutically acceptable salt or co-crystal thereof, at which clinical efficacy is achieved or reducing the doses by increments to a level at which efficacy can be maintained. In some embodiments, the methods provided comprise administering to the subject (e.g., a human) an initial daily dose of 100 mg to 1000 mg of the compound of Formula I, or a pharmaceutically acceptable salt or co-crystal thereof, and administering subsequent daily doses of the compound of Formula I, or a pharmaceutically acceptable salt or co-crystal thereof, over at least 6 days, wherein each subsequent daily dose is increased by 50 mg to 400 mg. Thus, it should also be understood that the dose of the compound of Formula I, or a pharmaceutically acceptable salt or co-crystal thereof, may be increased by increments until clinical efficacy is achieved. Increments of about 25 mg, about 50 mg, about 100 mg, or about 125 mg, or about 150 mg, or about 200 mg, or about 250 mg or about 300 mg can be used to increase the dose. The dose can be increased daily, every other day, two, three, four, five or six times per week, or once per week.

The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data. For example, pharmacokinetic and pharmacodynamic information about the compound of Formula I, or a pharmaceutically acceptable salt or co-crystal thereof, can be collected through preclinical in vitro and in vivo studies, later confirmed in humans during the course of clinical trials. Thus, for the compound of Formula I, or a pharmaceutically acceptable salt or co-crystal thereof, used in the methods provided herein, a therapeutically effective dose can be estimated initially from biochemical and/or cell-based assays. Then, dosage can be formulated in animal models to achieve a desirable circulating concentration range that modulates Syk expression or activity. As human studies are conducted further information will emerge regarding the appropriate dosage levels and duration of treatment for various diseases and conditions.

Toxicity and therapeutic efficacy of the compound of Formula I, or a pharmaceutically acceptable salt or co-crystal thereof, can be determined by standard pharmaceutical procedures in cell cultures or experimental animals, e.g., for determining the $LD_{50}$ (the dose lethal to 50/a of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the $ED_{50}$ with little or no toxicity.

The administration of the compound of Formula I, or a pharmaceutically acceptable salt or co-crystal thereof, may be administered under fed conditions. The term fed conditions or variations thereof refers to the consumption or uptake of food, in either solid or liquid forms, or calories, in any suitable form, before or at the same time when the compounds or pharmaceutical compositions thereof are administered. For example, the compound of Formula I, or a pharmaceutically acceptable salt or co-crystal thereof, may be administered to the subject (e.g., a human) within minutes or hours of consuming calories (e.g., a meal). In some embodiments, the compound of Formula I, or a pharmaceutically acceptable salt or co-crystal thereof, may be administered to the subject (e.g., a human) within 5-10 minutes, about 30 minutes, or about 60 minutes consuming calories.

Articles of Manufacture and Kits

Compositions (including, for example, formulations and unit dosages) comprising the compound of Formula I, or a pharmaceutically acceptable salt or co-crystal thereof, can be prepared and placed in an appropriate container, and labeled for treatment of an indicated condition. Accordingly, provided is also an article of manufacture, such as a container comprising a unit dosage form of the compound of Formula I, or a pharmaceutically acceptable salt or co-crystal thereof, and a label containing instructions for use of the compounds. In some embodiments, the article of manufacture is a container comprising a unit dosage form of the compound of Formula I, or a pharmaceutically acceptable salt or co-crystal thereof, and at least one pharmaceutically acceptable vehicle. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions. It should be understood that the active ingredient may be packaged in any material capable of improving chemical and physical stability, such as an aluminum foil bag. In some embodiments, diseases or conditions indicated on the label can include, for example, treatment of cancer.

Any pharmaceutical composition provided in the present disclosure may be used in the articles of manufacture, the same as if each and every composition were specifically and individually listed for use in an article of manufacture.

Kits comprising a pharmaceutical composition comprising a compound of Formula I, or a pharmaceutically acceptable salt or co-crystal thereof, are also provided. For example, a kit can comprise unit dosage forms of the compound of Formula I, or a pharmaceutically acceptable salt or co-crystal thereof, and a package insert containing instructions for use of the composition in treatment of a medical condition. In some embodiments, the kit comprises a unit dosage form of the compound of Formula I, or a pharmaceutically acceptable salt or co-crystal thereof, and at least one pharmaceutically acceptable vehicle. The instructions for use in the kit may be for treating a cancer, including, for example, a hematologic malignancy. In some embodiments, the instructions are directed to use of the pharmaceutical composition for the treatment of cancer, such as leukemia or lymphoma, including relapsed and refractory leukemia or lymphoma. In some embodiments, the instructions for use in the kit may be for treating a hematologic cancer selected from the group consisting of small lymphocytic lymphoma, non-Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/−villous lymphocytes), Nodal marginal zone lymphoma (+/−monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldestrom's macroglobulinemia. In one embodiment, the instructions for use in the kit may be for treating chronic lymphocytic leukemia or non-Hodgkin's lymphoma. In one embodiment, the NHL is diffuse large B-cell lymphoma, mantle cell lymphoma, follicular lymphoma, small lymphocytic lymphoma, lymphoplasmacytic lymphoma, and marginal zone lymphoma. In one embodiment, the hematologic malignancy is indolent non-Hodgkin's lymphoma. In some embodiments, diseases or conditions indicated on the label can include, for example, treatment of cancer.

In some instances, the instructions are directed to use of the pharmaceutical composition for the treatment of a solid tumor, wherein the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, ACTH-producing tumors.

In some instances, the instructions are directed to use of the pharmaceutical composition for the treatment of an allergic disorder and/or an autoimmune and/or inflammatory disease, and/or an acute inflammatory reaction. In some embodiments, the instructions are directed to use of the pharmaceutical composition for the treatment of an autoimmune disease. in some embodiments, the instructions are directed to use of the pharmaceutical composition for the treatment of an autoimmune disease selected from the group consisting of systemic lupus erythematosus, myestenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease. In some embodiments, the autoimmune disease is selected from the group consisting of asthma, rheumatoid arthritis, multiple sclerosis, chronic obstructive pulmonary disease and systemic lupus erythematosus.

Any pharmaceutical composition provided in the present disclosure may be used in the kits, the same as if each and every composition were specifically and individually listed for use in a kit.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula I, or a pharmaceutically acceptable salt or co-crystal thereof, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain a chiral center. Accordingly, if desired, such compounds can be prepared or isolated as pure stereoisomers, i.e., as individual enantiomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

List of abbreviations and acronyms.

| Abbreviation | Meaning |
| --- | --- |
| ° C. | Degree Celsius |
| anal | Analytical |
| ATP | Adenosine-5'-triphosphate |
| ATX II | Anemonia sulcata toxin |
| AcOH | Acetic acid |
| ACN | Acetonitrile |
| CAN | Ceric ammonium nitrate |
| CDI | 1,1'-carbonyldiimidazole |
| CHO | Chinese hamster ovary |
| conc. | Concentrated |
| d | Doublet |
| DABCO | 1,4-Diazabicyclo[2.2.2] octane |
| DAST | (Diethylamino)sulfur trifluoride |
| dd | Doublet of doublets |
| DCE | 1,2-dichloroethane |
| DCM | Dichloromethane |
| DEAD | Diethyl azodicarboxylate |
| DIPEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| equiv/eq | Equivalents |
| ESI | Electrospray ionization |
| Ac | Acetate |
| Et | Ethyl |
| EtOAc | Ethyl Acetate |
| g | Grams |
| HEPES | (4-(2-Hydroxyethyl)-1-piperazineethanesulfonic acid) |
| HATU | 2-(7-Aza-1H-Benzotriazole-1-yl)-1,1,3,3-tetramethyluronium hexafluorophosphate |
| hERG | human Ether-à-go-go Related Gene |
| HMDS | hexamethyldisilazane(azide) |
| HPLC | High-performance liquid chromatography |
| h | Hours |
| Hz | Hertz |
| IPA | Isopropyl alcohol |
| IC$_{50}$ | The half maximal inhibitory concentration |
| IMR-32 | Human neuroblastoma cell line |
| J | Coupling constant |
| Kg | Kilogram |
| kHz | Kilohertz |
| LAH | Lithium ammonium hydride |
| LCMS/LC-MS | Liquid chromatography-mass spectrometry |
| M | Molar |
| m | multiplet |
| m/z | mass-to-charge ratio |
| M+ | Mass peak |
| M+H | Mass peak plus hydrogen |
| mCPBA | 3-chloroperoxybenzoic acid |

-continued

| Abbreviation | Meaning |
|---|---|
| Me | Methyl |
| MeOH | Methanol |
| mg | Milligram |
| MHz | Megahertz |
| min/m | Minute |
| ml/mL | Milliliter |
| mM | Millimolar |
| mmol | Millimole |
| nmol | Nanomole |
| mOsmol | Milliosmole |
| MRM | Magnetic Resonance Microscopy |
| MS | Mass spectroscopy |
| ms | Millisecond |
| mV | Millivolt |
| mw | Microwave |
| N | Normal |
| mol | Mole |
| NMP | N-methylpyrrolidinone |
| NMR | Nuclear magnetic resonance |
| pA | Picoamps |
| Ph | Phenyl |
| ppm | Parts per million |
| prep | Preparative |
| q.s. | Quantity sufficient to achieve a stated function |
| Rf | Retention factor |
| RP | Reverse phase |
| RT/t | Room temperature |
| s | Second |
| s | Singlet |
| SEM | 2-(Trimethylsilyl)ethoxymethyl |
| t | Triplet |
| TB | Tonic Block |
| TEA | Triethylamine |
| TFA | Trifluoroacetic acid |
| THF | Tetrahydrofuran |
| TLC | Thin layer chromatography |
| TMS | trim ethyl silyl |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |
| μmol | Micromole |

EXAMPLES

Preparation of Common Intermediates

Intermediate 1.01. Preparation of tert-Butyl (6-bromoimidazo[1,2-a]pyrazin-8-yl)(4-(4-(oxetan-3-yl)piperazin-1-yl)phenyl)carbamate IV and tert-butyl 4-(4-(oxetan-3-yl)piperazin-1-yl)phenyl(6-(tributylstannyl)imidazo[1,2-a]pyrazin-8-yl)carbamate V

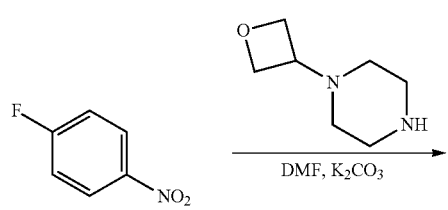

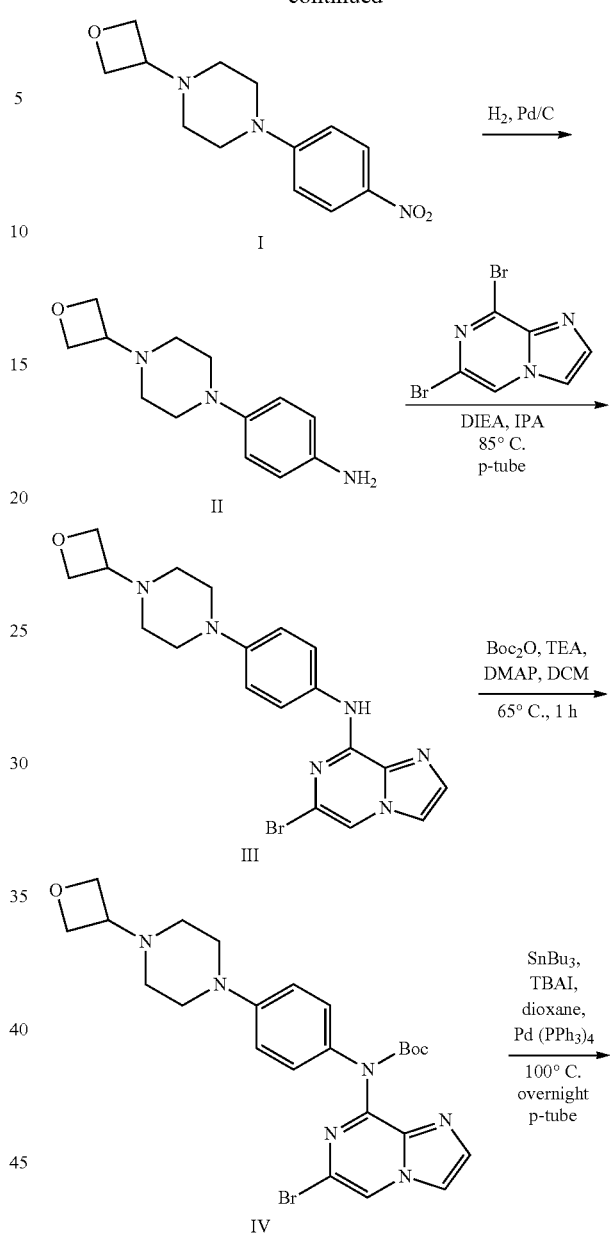

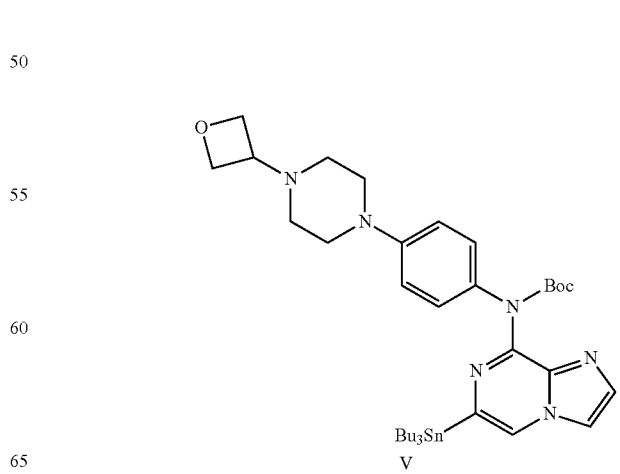

1-(4-Nitrophenyl)-4-(oxetan-3-yl)piperazine I: In a 500 mL round bottom flask, 1-(oxetan-3-yl)piperazine (3.02 g, 21.26 mmoles), potassium carbonate (5.87 g, 42.52 mmoles), 1-fluoro-4-nitrobenzene (3.00 g, 21.26 mmoles) was combined in acetonitrile (33 mL) and stirred under nitrogen overnight at 100° C. The mixture was diluted with water (100 mL) and extracted with DCM (100 mL×3), dried over anhydrous sodium carbonate, filtered and the filtrate was concentrated. The residue was dissolved in minimal DCM using a sonicator and crashed out with hexane. The precipitate was filtered, washed with hexane and dried to provide the title compound I.

4-(4-(Oxetan-3-yl)piperazin-1-yl)aniline II: In a hydrogenation vessel, 1-(4-nitrophenyl)-4-(oxetan-3-yl)piperazine I (4.70 g, 17.85 mmoles) was dissolved as much as possible in MeOH (26 mL) and DCM (5 mL). Pd/C (10%)(2.85 g, 2.68 mmoles) was added and the reaction was stored under nitrogen. The reaction was shaken on the Parr hydrogenator at 45 PSI. After 15 minutes, the reaction was fully recharged to 45 PSI and shaken for an additional hour. The material was filtered over celite, washed with 25% MeOH/DCM and concentrated to provide the title compound II.

6-Bromo-N-(4-(4-(oxetan-3-yl)piperazin-1-yl)phenyl) imidazo[1,2-a]pyrazin-8-amine III: To 4-(4-(oxetan-3-yl) piperazin-1-yl)aniline II (2.00 g, 8.57 mmoles), hunig's base (3.29 mL) and 6,8-dibromoimidazo[1,2-a]pyrazine (2.37 g, 8.57 mmoles) was added in DMF (43 mL). The reaction was stirred at 85° C. in a pressure tube for overnight. The material was quenched with saturated sodium bicarbonate, extracted with DCM (120 mL×3) and the organic layers were combined and washed with water (120 mL×3), dried over anhydrous sodium carbonate and concentrated. The crude material was purified using a 120 g Isco column and eluted off using a stepwise gradient of 0-60% (10% MeOH/DCM). The desired fractions were combined and concentrated to provide the title compound III.

tert-Butyl (6-bromoimidazo[1,2-a]pyrazin-8-yl)(4-(4-(oxetan-3-yl)piperazin-1-yl)phenyl)carbamate IV: 6-bromo-N-(4-(4-(oxetan-3-yl)piperazin-1-yl)phenyl)imidazo[1,2-a] pyrazin-8-amine III (1000 mg, 2.33 mmol), di-tert-butyl dicarbonate (1016.72 mg, 4.66 mmol) and N,N-dimethylpyridin-4-amine (21.34 mg, 0.17 mmol) were stirred in DCM (1.01 ml) and refluxed at 65° C. for 3 h. The reaction was diluted with 100 mL of DCM, washed with H2O (×3), dried, filtered and concentrated. The crude material was dissolved in minimal DCM, loaded onto a preloaded silica loader and eluted off a 40 g column using 0-30% MeOH/DCM over 20 column volumes. The desired fractions were combined and concentrated to provide the title compound. This compound is used in Example 2.

tert-Butyl 4-(4-(oxetan-3-yl)piperazin-1-yl)phenyl(6-(tributylstannyl)imidazo[1,2-a]pyrazin-8-yl)carbamate V: In a 350 mL p-tube, tert-butyl 6-bromoimidazo[1,2-a]pyrazin-8-yl(4-(4-(oxetan-3-yl)piperazin-1-yl)phenyl)carbamate IV (8150 mg, 15.39 mmol), 1,1,1,2,2,2-hexabutyldistannane (11.67 ml, 23.09 mmol), tetrakis(triphenylphosphine)palladium (889.43 mg, 0.77 mmol), and tetrabutylammonium iodide (5686.03 mg, 15.39 mmol) were combined in dioxane (62 ml) and heated to 110° C. overnight. According to LCMS, no starting material remained. The reaction was absorbed onto celite and eluted off a 160 g alumina column using a 0-10-20-30-100% (50% EtOAc/Hex-Hex) gradient holding at 50% for 10-15 column volumes over 50-60 column volumes to provide the title compound V. This compound is used in Examples 1 and 2.

Intermediate 1.02. Preparation tert-butyl (6-bromo-5-methylimidazo[1,2-a]pyrazin-8-yl)(4-(4-(oxetan-3-yl)piperazin-1-yl)phenyl)carbamate X

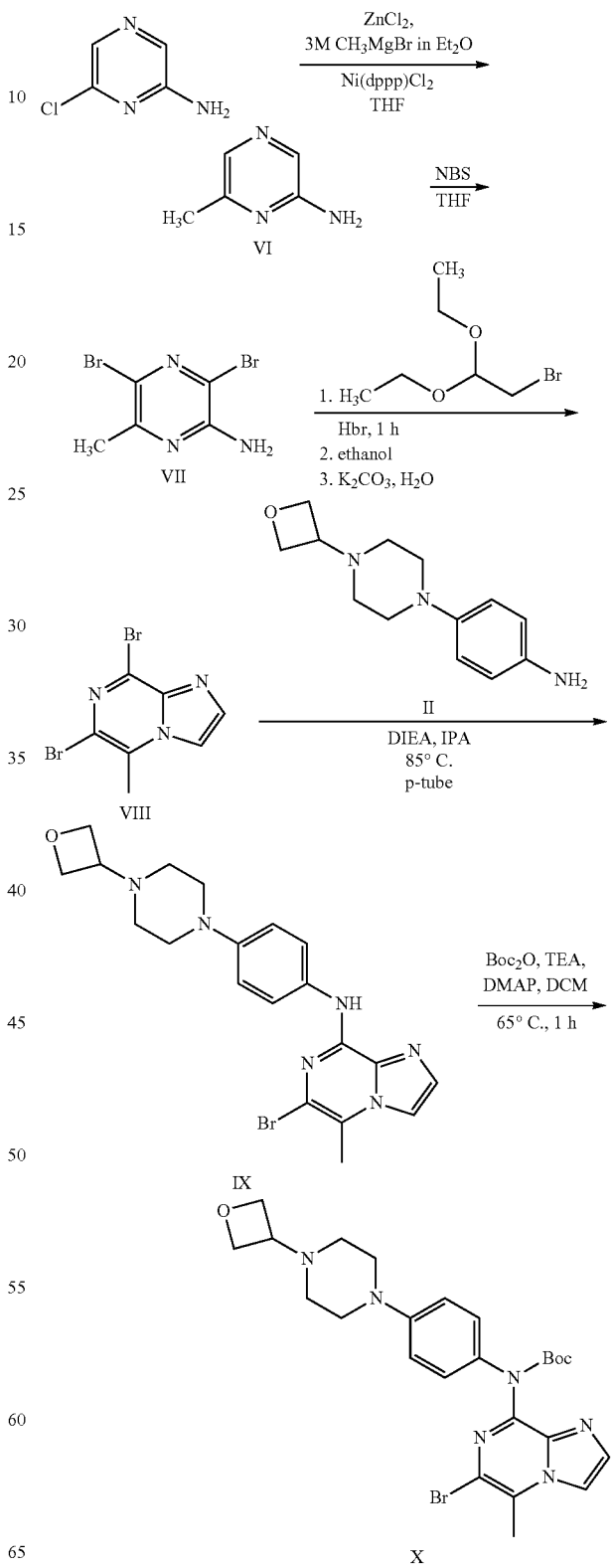

6-Methylpyrazin-2-amine VI: To a solution of anhydrous zinc(II) chloride (26.3 g, 193 mmol) in TI-1 (150 mL) at 0° C., was added 3M methyl magnesium bromide in diethyl ether (129 mL) drop wise over a period of 1 h. [1,3-bis (diphenylphosphino)propane]nickel(II) chloride (2.08 g, 3.85 mmol) was then added and the mixture allowed to warm to room temperature. To the above mixture, a solution of 6-chloro-2-aminopyrazine (5.00 g, 38.6 mmol) in anhydrous TI-1 (25 mL) was added and the reaction stirred, under a nitrogen atmosphere, at reflux for 6 h. After this time, the mixture was cooled to room temperature, then to 0° C. and carefully quenched with saturated aqueous ammonium chloride (50 mL). The organic layer was separated and dried over sodium sulfate. The drying agent was filtered and the filtrate concentrated under reduced pressure to provide crude 6-methylpyrazin-2-amine VI, which was used in the next step without purification: $^1$H NMR (400 MHz, CDCl$_3$) δ: 7.63 (s, 1H), 7.53 (s, 1H), 4.96 (bs, 2H), 2.16 (s, 3H).

3,5-Dibromo-6-methylpyrazin-2-amine VII: To a solution of 6-methylpyrazin-2-amine VI (2.00 g, 18.3 mmol) in THF (40 mL) at 10° C., was added N-bromosuccinimide (6.70 g, 37.6 mmol) portion wise over 15 min and the mixture allowed to warm to room temperature while stirring. After 2 h, the reaction was concentrated under reduced pressure and the resulting residue was purified by column chromatography (silica, gradient, hexanes to EtOAc) to provide 3,5-dibromo-6-methylpyrazin-2-amine VII: $^1$H NMR (400 MHz, CDCl$_3$) δ: 4.93 (bs, 2H), 2.38 (s, 3H).

6,8-Dibromo-5-methylimidazo[1,2-a]pyrazine VIII: A mixture of 2-bromo-1,1-diethoxyethane (3.21 mL, 20.7 mmol) and 48% aqueous hydrobromic acid (1.0 mL) was stirred at reflux for 2 h. The reaction was then cooled to room temperature and treated with sodium bicarbonate until gas evolution ceased. The mixture was filtered and the filtrate diluted with ethanol (15 mL). To this mixture, 3,5-dibromo-6-methylpyrazin-2-amine VII (3.00 g, 11.2 mmol) was added and the reaction stirred at reflux for 16 h. After this time, the reaction was cooled to room temperature and concentrated under reduced pressure to a volume of approximately 10 mL. The suspension was filtered and the filter cake washed with cold ethanol (5 mL). The filter cake was then taken into water (50 mL) and the pH was adjusted to ~8 with potassium carbonate. The resulting suspension was filtered and the filter cake dried to a constant weight under vacuum to provide 6,8-dibromo-5-methylimidazo[1,2-a]pyrazine VIII: $^1$H NMR (400 MHz, CDCl$_3$) δ: 7.90 (s, 1H), 7.72 (s, 1H), 2.74 (s, 3H).

6-Bromo-5-methyl-N-(4-(4-(oxetan-3-yl)piperazin-1-yl) phenyl)imidazo[1,2-a]pyrazin-8-amine IX: The compound IX was prepared from 6,8-dibromo-5-methylimidazo[1,2-a] pyrazine VIII using the method as described for preparing 6-bromo-N-(4-(4-(oxetan-3-yl)piperazin-1-yl)phenyl)imidazo[1,2-a]pyrazin-8-amine III in Intermediate Example 1.01.

tert-Butyl (6-bromo-5-methylimidazo[1,2-a]pyrazin-8-yl) (4-(4-(oxetan-3-yl)piperazin-1-yl)phenyl)carbamate X: The compound X was prepared from 6-bromo-5-methyl-N-(4-(4-(oxetan-3-yl)piperazin-1-yl)phenyl)imidazo[1,2-a] pyrazin-8-amine IX using the method as described for preparing tert-butyl (6-bromoimidazo[1,2-a]pyrazin-8-yl) (4-(4-(oxetan-3-yl)piperazin-1-yl)phenyl)carbamate IV in Intermediate Example 1.01. This compound is used in Example 4.

Synthesis of Examples 1-7

Example 1 Preparation of 6-(6-amino-5-methylpyrazin-2-yl)-N-(4-(4-(oxetan-3-yl)piperazin-1-yl)phenyl)imidazo [1,2-a]pyrazin-8-amine (1)

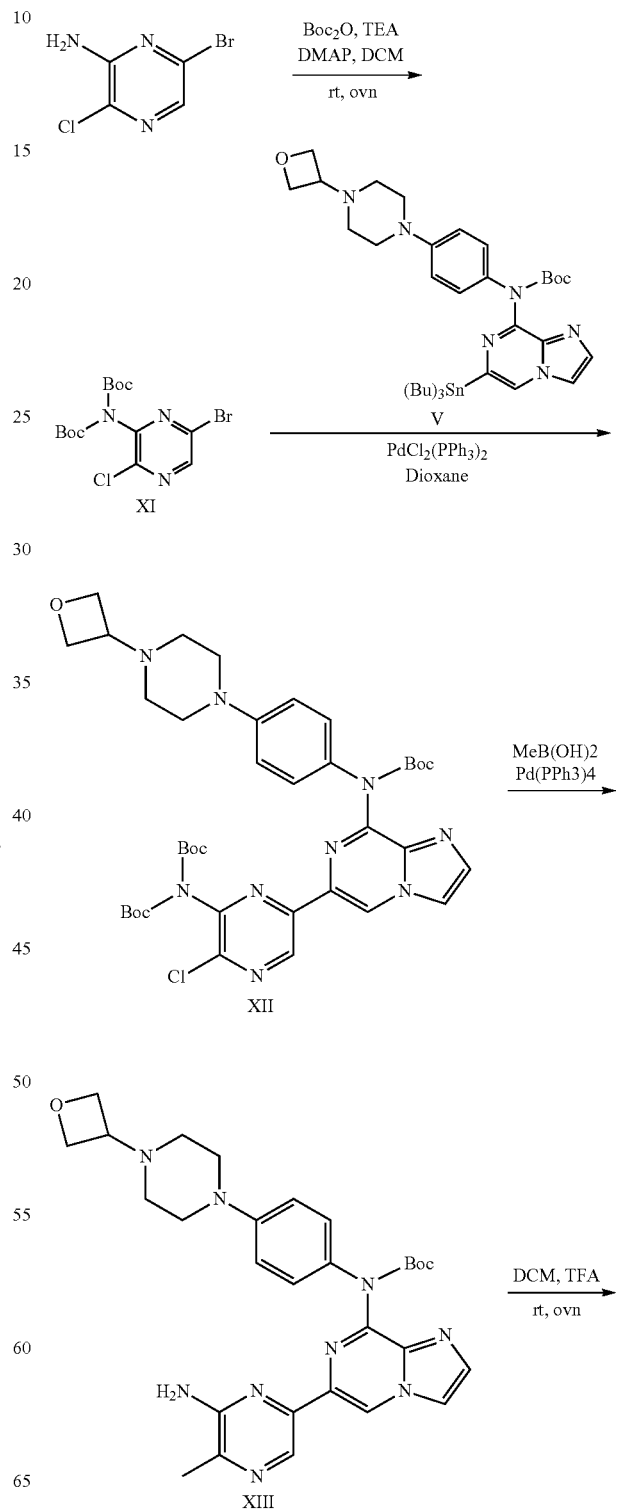

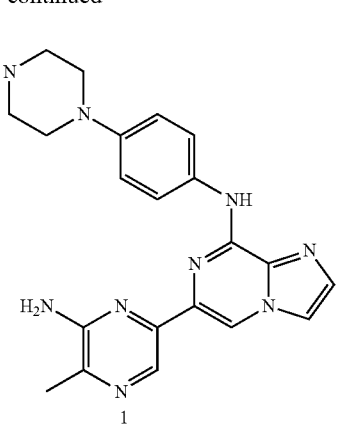

2-Bis(tert-butoxycarbonyl)amino-6-bromo-3-chloropyrazine XI: 6-Bromo-3-chloropyrazin-2-amine (2000 mg, 9.59 mmol) was dissolved in DCM (48 ml) followed by triethylamine (3.99 ml, 28.78 mmol), di-tert-butyl dicarbonate (4188.12 mg, 19.19 mmol), and N,N-dimethylpyridin-4-amine (87.91 mg, 0.72 mmol). The reaction was allowed to stir at room temperature for overnight. The crude material was washed with water, dried, filtered and concentrated. The crude material was dissolved in minimal DCM and loaded onto a 25 g prepacked silica loader and eluted off a 40 g column using 0-30% MeOH/DCM. The title compound XI was isolated and identified by LCMS and NMR. The product was a mix of mono and bis boc-protected material, mainly bis boc-protected as observed by NMR.

tert-Butyl tert-butoxycarbonyl(6-(8-((tert-butoxycarbonyl)(4-(4-(oxetan-3-yl)piperazin-1-yl)phenyl)amino)imidazo[1,2-a]pyrazin-6-yl)-3-chloropyrazin-2-yl)carbamate XII: tert-Butyl 4-(4-(Oxetan-3-yl)piperazin-1-yl)phenyl(6-(tributylstannyl)imidazo[1,2-a]pyrazin-8-yl)carbamate V (1000 mg, 1.4 mmol), 2-Bis(tert-butoxycarbonyl)amino-6-bromo-3-chloropyrazine XI (552 mg, 1.35 mmol), and PdCl$_2$(PPh$_3$)$_2$ (142.77 mg, 0.20 mmol), in 1,4-Dioxane (11.27 ml) was irridated in the microwave for 20 min at 140° C. The reaction was absorbed onto celite and eluted off a 40 g Gold Isco column using 0-10-100% (30% MeOH/DCM) over 20 column volumes. Fractions 34-39 were collected and concentrated. According to NMR, the title compound XII was identified and isolated.

tert-Butyl (6-(6-amino-5-methylpyrazin-2-yl)imidazo[1,2-a]pyrazin-8-yl)(4-(4-(oxetan-3-yl)piperazin-1-yl)phenyl)carbamate XIII: In a microwave vial, tert-butyl tert-butoxycarbonyl(6-(8-((tert-butoxycarbonyl)(4-(4-(oxetan-3-yl)piperazin-1-yl)phenyl)amino)imidazo[1,2-a]pyrazin-6-yl)-3-chloropyrazin-2-yl)carbamate XII (300 mg, 0.44 mmol), methylboronic acid (794.39 mg, 13.27 mmol), tetrakis(triphenylphosphine)palladium (51.12 mg, 0.04 mmol), and 2M Na$_2$CO$_3$ (0.44 ml) were combined in DME (1.77 ml) and irridated in the microwave for 20 min at 150° C. The reaction was worked up using 25% MeOH/DCM and water. The organic layers were combined, dried, filtered and concentrated. The crude material was loaded onto silica and eluted off a 40 g Gold column using 0-5-15-25-50% (30% MeOH/DCM) over 45 column volumes. The desired fractions were concentrated and provided tert-butyl (6-(6-amino-5-methylpyrazin-2-yl)imidazo[1,2-a]pyrazin-8-yl)(4-(4-(oxetan-3-yl)piperazin-1-yl)phenyl)carbamate XIII as the minor product and the desired final compound 1 as an inseparable mixture (208 mg total) and were taken in to the TFA reaction.

6-(6-Amino-5-methylpyrazin-2-yl)-N-(4-(4-(oxetan-3-yl)piperazin-1-yl)phenyl)imidazo[1,2-a]pyrazin-8-amine (1): To a solution of tert-butyl 6-(6-amino-5-methylpyrazin-2-yl)imidazo[1,2-a]pyrazin-8-yl(4-(4-(oxetan-3-yl)piperazin-1-yl)phenyl)carbamate XIII (48 mg, 0.09 mmol) and 6-(6-amino-5-methylpyrazin-2-yl)-N-(4-(4-(oxetan-3-yl)piperazin-1-yl)phenyl)imidazo[1,2-a]pyrazin-8-amine (1, 160 mg, 0.35 mmol) in DCM (2.5 ml) was added TFA (0.16 ml, 2.15 mmol). Additional TFA (0.48 ml, 6.5 mmol) was added to the reaction mixture to ensure reaction completion. The reaction was then cooled to 0° C. and quenched with sat. NaHCO$_3$, then extracted with DCM (5 ml×3), and the combined organic layers were washed with water (5 ml×2), brine (5 ml×1), dried (Na$_2$SO$_4$), and concentrated to give the crude product. The crude material was absorbed onto silica and eluted off a 24 g Gold Isco column using 0-15-25-40-100% (30% MeOH/DCM). The desired fractions were combined and concentrated to provide the desired compound. LCMS-ESI$^+$ (m/z): [M+H]$^+$: 458.22. $^1$H NMR (300 MHz, d$_6$-DMSO) δ: 9.48 (s, 1H), 8.54 (s, 1H), 8.41 (s, 1H), 8.11 (s, 1H), 7.95 (d, 2H), 7.6 (s, 1H), 6.98 (d, 2H), 6.2 (s, 2H), 4.58-4.45 (dt, 4H), 3.3 (m, 1H), 3.14 (t, 4H), 2.50-2.4 (dt, 4H), 2.33 (s, 1H). Alternatively, compound XII could be taken directly to this step and similarly de-protected to provide the 5-chloropyrazine substituted analog.

Example 2. Preparation of 6-(6-aminopyrazin-2-yl)-N-(4-(4-(oxetan-3-yl)piperazin-1-yl)phenyl)imidazo[1,2-a]pyrazin-8-amine (2)

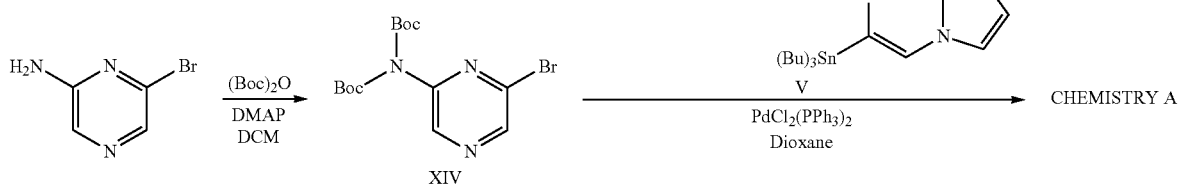

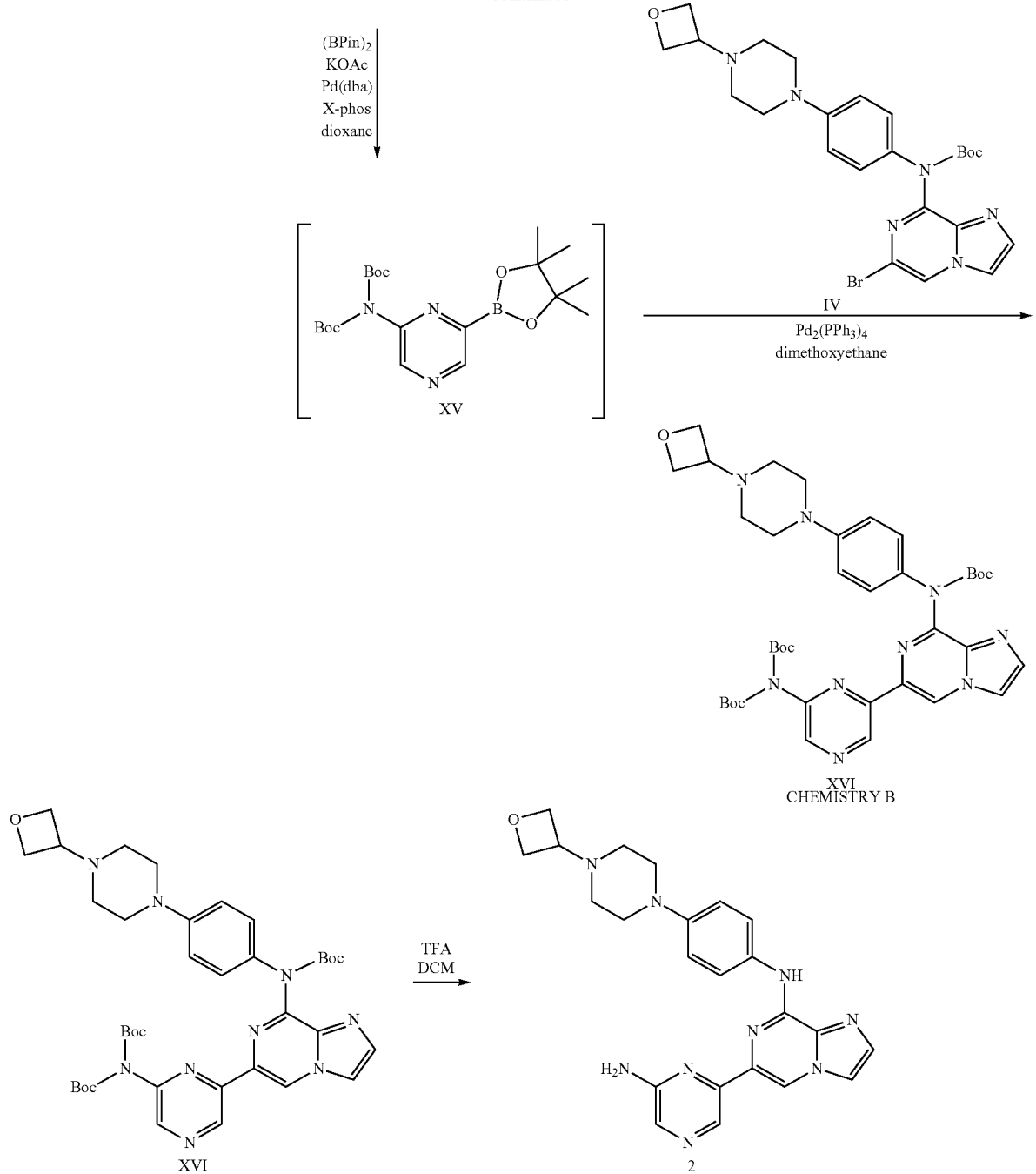

2-Bis(tert-butoxycarbonyl)amino-6-bromopyrazine XIV: To a mixture of 6-bromopyrazin-2-amine (5 g, 28.7 mmol) and di-tert-butyl dicarbonate (25.09 g, 114.94 mmol) was added DCM (10 ml) followed by DMAP (0.351 g, 29 mmol). The reaction was heated to 55° C. for 1 h, cooled to RT, the reaction was partitioned between water and DCM, purified on silica gel and concentrated to provide of 2-bis(tert-butoxycarbonyl)amino-6-bromopyrazine XIV. LCMS-ESI+ (m/z): [M+H]+: 374.14. $^1$H NMR (DMSO) δ: 8.84 (d, 2H), 1.39 (s, 18H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI—CHEMISTRY A route: tert-Butyl 4-(4-(oxetan-3-yl)piperazin-1-yl)phenyl(6-(tributylstannyl)imidazo[1,2-a]pyrazin-8-yl)carbamate V (215 mg, 0.291 mmol), was combined with 2-bis(tert-butoxycarbonyl)amino-6-bromopyrazine XIV (217.58 mg, 0.581 mmol), bis(triphenylphosphine)palladium(II) dichloride (30.61 mg, 0.044 mmol) and 1,4-dioxane (5 ml). The reaction mixture was stirred in a microwave reactor at 120° C. for 30 min. The reaction mixture was quenched with saturated KF, extracted with EtOAc, purified on silica gel, eluted with EtOAc. The desired fractions were combined and concentrated to provide 100 mg (46% yield) of tert-butyl (6-(6-(bis(tert-butoxycarbonyl)amino)pyrazin-2-yl)imidazo[1,2-a]pyrazin-8-yl)(4-(4-(oxetan-3-yl)piperazin-1- yl)phenyl)carbamate XVI. LCMS-ESI+ (m/z). [M+H]+: 744.4. ¹H NMR (300 MHz d$_6$-DMSO) δ: 9.37 (s, 1H), 9.18 (s, 1H), 8.77 (s, 1H), 8.33 (d, 1H), 7.87 (d, 1H), 7.28-7.25 (d, 2H), 6.92-6.89 (d, 2H), 4.55-4.41 (m, 4H), 3.4 (m, 1H), 3.14-3.11 (m, 4H), 2.37-2.34 (m, 4H), 1.37 (s, 18H), 1.3 (s, 9H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI—CHEMISTRY B route: Step 1: To a dry 250 mL round-bottomed flask was added 2-bis(tert-butoxycarbonyl)amino-6-bromopyrazine XIV (1.0 g, 1.0 equiv, 2.67 mmol), KOAc (790 mg, 8.02 mmol, 3.0 equiv), 4,4,4',4',5,5,5',5'-octamethyl-2,2'-bi(1,3,2-dioxaborolane) (750 mg, 2.94 mmol, 1.1 equiv), Pd(dba) (171 mg, 0.187 mmol, 0.07 equiv) and X-phos (128 mg, 0.267 mmol, 0.1 equiv) followed by 1,4-dioxane (25 mL) and the solution was sonicated for 5 min and then purged with N$_2$ gas for 5 min. The flask with contents was then placed under N$_2$ atmosphere and heated at 110° C. for 90 min. Once full conversion to the pinacolboronate was achieved by LCMS, the reaction was removed from heat and allowed to cool to RT. Once cool, the reaction contents were filtered through Celite and the filter cake was washed 3×20 mL EtOAc. The resultant solution was then concentrated down to a deep red-orange syrup providing N, N-BisBoc 6-(4,4,5,5-tetramethyl-1,3,2-dioxaborolan-2-yl)pyrazin-2-amine XV, which was used directly in the next step.

Step 2: The freshly formed N, N-BisBoc 6-(4,4,5,5-tetramethyl-1,3,2-dioxaborolan-2-yl)pyrazin-2-amine XV (2.67 mmol based on 100% conversion, 2.0 equiv based on bromide) was dissolved in 20 Ml of 1,2-dimethoxyethane and to that solution was added tert-butyl (6-bromoimidazo[1,2-a]pyrazin-8-yl)(4-(4-(oxetan-3-yl)piperazin-1-yl)phenyl)carbamate IV (707 mg, 1.34 mmol, 1.0 equiv), Na$_2$CO$_3$ (283 mg, 2.67 mmol, 2.0 equiv), Pd(PPh$_3$)$_4$ (155 mg, 0.134 mmol, 0.1 equiv) and water (10 mL) and the solution was degassed for 5 min using N$_2$ gas. The reaction was then placed under N$_2$ atmosphere and heated at 110° C. for 90 min. LCMS showed complete consumption of the bromide starting material and the reaction was removed from heat and allowed to cool to RT. The reaction was diluted with 100 mL water and 100 mL 20% MeOH/DCM and the organic layer was recovered, extracted 1× sat. NaHCO$_3$, 1× sat brine and then dried over Na$_2$SO$_4$. The solution was then filtered and concentrated down to an orange-red solid. The sample was then slurried in warm MeOH, sonicated then filtered, washing 2×20 mL with cold MeOH and then the cream-colored solid was dried on hi-vacuum overnight to yield 905 mg of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI.

6-(6-Aminopyrazin-2-yl)-N-(4-(4-(oxetan-3-yl)piperazin-1-yl)phenyl)imidazo[1,2-a]pyrazin-8-amine (2): To a solution of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate XVI (200 mg, 0.269 mmol) in DCM (2 ml) was added TFA (0.5 ml, 6.578 mmol). The reaction was stirred at rt for 16 h, saturated sodium bicarbonate was added, extracted with EtOAC and purified on silica gel, eluted with 5% MeOH/EtOAc, 20% MeOH/EtOAc. The desired fractions were combined and concentrated to provide the title compound 2. LCMS-ESI+ (m/z): [M+H]+: 444.2. ¹H NMR (300 MHz d$_6$-DMSO) δ: 9.5 (s, 1H), 8.588 (s, 1H), 8.47 (s, 1H), 8.12 (d, 1H), 7.95-7.92 (d, 2H), 7.88 (s, 1H), 7.62 (s, 1H), 6.99-6.96 (d, 2H), 6.46 (s, 2H), 4.57-4.53 (m, 2H), 4.48-4.44 (m, 2H), 3.43 (m, 1H), 3.15-3.12 (m, 4H), 2.41-2.38 (m, 4H).

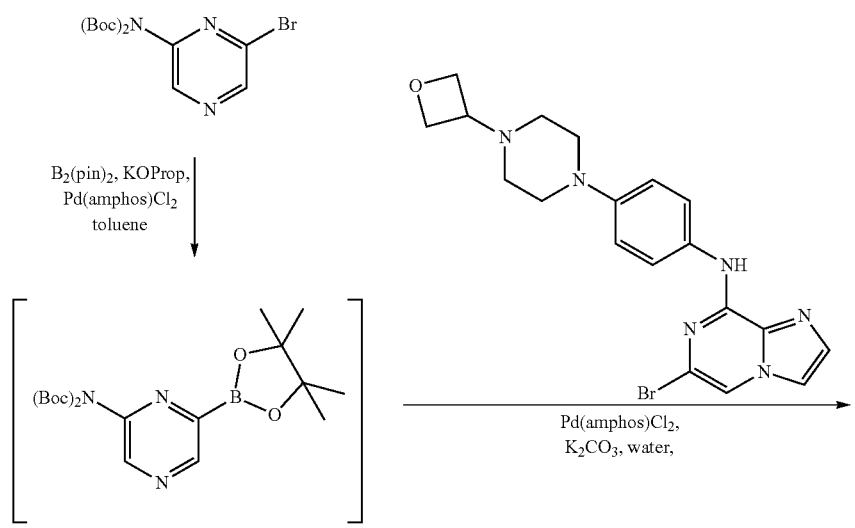

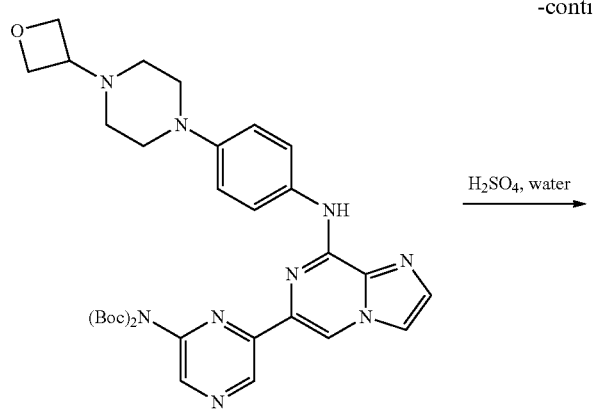

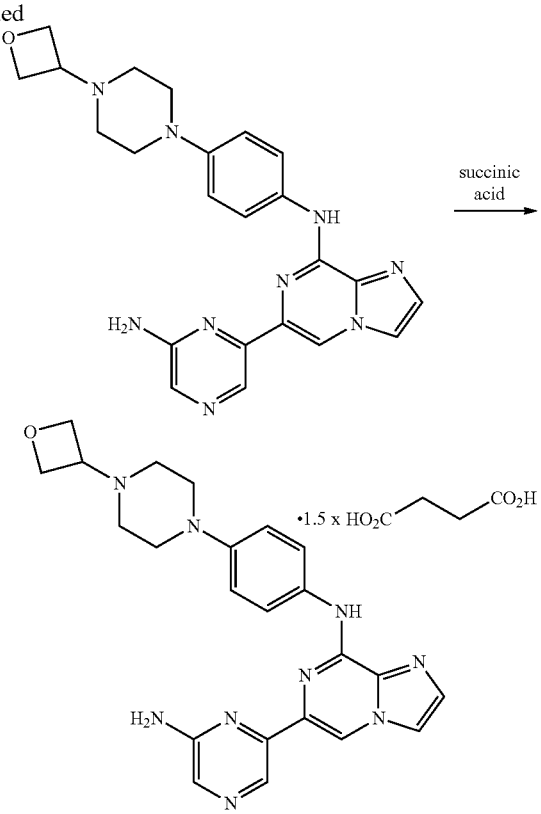

Example 2—Alternate Synthesis

Di-tert-butyl {6-[8-({4-[4-(oxetan-3-yl)piperazin-1-yl]phenyl}amino)imidazo[1,2-a]pyrazin-6-yl]pyrazin-2-yl}imidodicarbonate To a 720 L reactor, was added di-tert-butyl (6-bromopyrazin-2-yl)imidodicarbonate (18.5 kg, 1.41 equiv, 49 mol), bis(pinacolato)diboron (13.8 kg, 1.56 equiv, 54 mol), potassium propionate (11.9 kg, 3.02 equiv, 106 mol), and bis(di-tert-butyl(4-dimethylaminophenyl) phosphine)dichloropalladium (1.07 kg, 0.0043 equiv, 1.5 mol), followed by degassed toluene (173 L). The mixture was degassed then heated at 65° C. until the reaction was deemed complete (0% tert-butyl 2-((6-bromopyrazin-2-yl)(tert-butoxycarbonyl)amino)-2-oxoacetate) by UPLC. Upon completion, the reaction was cooled to 23° C. Once cooled, 6-bromo-N-(4-(4-(oxetan-3-yl)piperazin-1-yl)phenyl)imidazo[1,2-a]pyrazin-8-amine (15.0 kg, 1.00 equiv, 35 mol) was added and the mixture was degassed. A degassed aqueous potassium carbonate solution prepared using water (54 L) and potassium carbonate (20.6 g. 4.26 equiv, 149 mol) was then added to the reaction mixture and the reactor contents was degassed. The reactor contents was heated at 65° C. until reaction was deemed complete (1% 6-bromo-N-(4-(4-(oxetan-3-yl)piperazin-1-yl)phenyl)imidazo[1,2-a]pyrazin-8-amine) by UPLC. Upon completion, the reaction was cooled to 24° C.

The cooled mixture was concentrated and then diluted with dichloromethane (300 L), transferred to a 1900 L reactor and rinsed forward with dichloromethane (57 L). N-acetyl-L-cysteine (3.8 kg) was charged and the mixture was agitated for 15 h. Water (135 L) was then added and the mixture was filtered and rinsed forward with dichloromethane (68 L). The organic layer was recovered and washed with a brine solution prepared using water (68 L) and sodium chloride (7.5 kg).

The resultant organic layer was polish filtered then concentrated and tert-butyl methyl ether (89.9 kg) was slowly charged keeping the temperature at 31° C. The contents was cooled to 0° C. and aged, then filtered and rinsed with tert-butyl methyl ether (32.7 kg) and dried at 40° C. to give 17.2 kg of di-tert-butyl {6-[8-({4-[4-(oxetan-3-yl)piperazin-1-yl]phenyl}amino)imidazo[1,2-a]pyrazin-6-yl]pyrazin-2-yl}imidodicarbonate.

LCMS-ESI$^+$ (m/z): [M+H]$^+$: 644.3. $^1$H NMR (400 MHz, CDCl$_3$) δ: 9.43 (s, 1H), 8.58 (s, 1H), 8.53 (s, 1H), 8.02 (s, 1H), 7.84 (m, 2H), 7.63 (d, 1H), 7.61 (d, 1H), 7.04 (m, 2H), 4.71 (m, 4H), 3.59 (m, 1H), 3.27 (m, 4H), 2.55 (m, 4H), 1.46 (s, 18H).

6-(6-Aminopyrazin-2-yl)-N-(4-(4-(oxetan-3-yl)piperazin-1-yl)phenyl)imidazo[1,2-a]pyrazin-8-amine succinate (Example 2)

To a slurry of di-tert-butyl {6-[8-({4-[4-(oxetan-3-yl)piperazin-1-yl]phenyl}amino)imidazo[1,2-a]pyrazin-6-yl]pyrazin-2-yl}imidodicarbonate (225 g, 0.35 mol, 1 mol eq.) in water (12 parts) was added a solution of sulfuric acid (3.1 parts, 6.99 mol, mol eq.) in water (5 parts). The reaction was heated to ca. 40° C. and stirred at this temperature for ca. 4 h at which point the reaction is deemed complete. The reaction mixture was cooled to ca. 22° C., acetone (3 parts) was charged and a solution of sodium carbonate (4.1 parts, 8.75 mol, 25.0 mol eq.) in water (15 parts) was added. The resulting slurry was filtered and the wet cake was washed with water in portions (4×1 parts), then with tert-butyl methyl ether (4 parts). The wet cake (Example 2 free base) was dried at ca. 60° C. To the slurry of dry Example 2 free base in 2-propanol (2.3 parts) was added a solution of succinic acid (Based on the isolated Example 2 free base: 0.43 parts, 1.6 mol eq.) in 2-propanol (15 parts). The resulting slurry was heated to ca. 40° C. and stirred at this temperature for ca. 2 h and then cooled to ca. 22° C., followed by a stir period of ca. 16 h. The slurry was filtered at ca. 22° C. and the wet cake was washed with 2-propanol (5 parts) and dried at ca. 60° C. to afford the product.

LCMS-ESI$^+$ (m/z): [M+H]$^+$: 620.65. $^1$H NMR (400 MHz d$_6$-DMSO) δ: 12.2 (broad s, 1.5H), 9.58 (s, 1H), 8.63 (s, 1H), 8.50 (s, 1H), 8.15 (s, 1H), 7.95 (d, 2H), 7.90 (s, 1H), 7.64 (s, 1H), 7.00 (d, 2H), 6.50 (s, 2H), 4.52 (dd, 4H), 3.45 (m, 1H), 3.19 (m, 4H), 2.40 (in, 10H).

Example 3. Preparation of (R)-(4-(4-((6-(6-amino-pyrazin-2-yl)imidazo[1,2-a]pyrazin-8-yl)amino)phenyl)morpholin-2-yl)methanol (3)

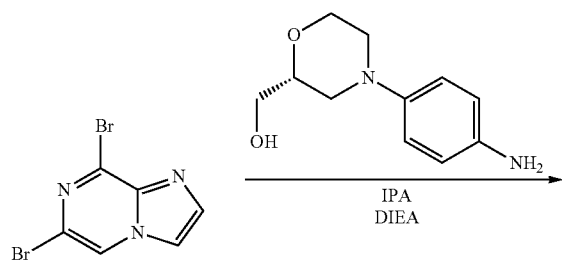

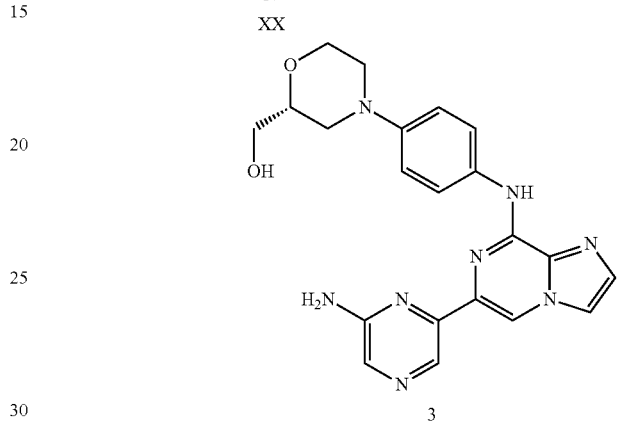

(R)-(4-(4-((6-Bromoimidazo[1,2-a]pyrazin-8-yl)amino) phenyl)morpholin-2-yl)methanol XVII: In a 250 mL round bottom flask equipped with a condenser was placed 6,8-dibromoimidazo[1,2-a]pyrazine (2000 mg, 7.22 mmol) and added 30 mL isopropanol followed by N,N-diisopropylethylamine (2.52 ml, 14.44 mmol) and (R)-(4-(4-aminophenyl)morpholin-2-yl)methanol (1504.12 mg, 7.22 mmol). The reaction was heated to reflux (oil bath 95° C.) overnight. The reaction was cooled and precipitates were collected by filtration and washed with isopropanol followed by hexanes to give the desired compound XVII.

(R)-tert-Butyl (6-bromoimidazo[1,2-a]pyrazin-8-yl)(4-(2-(((tert-butoxycarbonyl)oxy)methyl)morpholino)phenyl) carbamate XVIII: In a 250 mL round bottom flask was placed (R)-(4-(4-((6-bromoimidazo[1,2-a]pyrazin-8-yl) amino)phenyl)morpholin-2-yl)methanol XVII (2.80 g, 6.9 mmol) and added DCM followed by triethylamine (2.9 mL, 2.1 g, 20.8 mmol), DMAP (63 g, 0.52 mmol) and di-tert-butyl dicarbonate (3.8 g, 17.3 mmol). The reaction was stirred overnight then diluted with DCM and water, separated, washed with brine, dried over Na$_2$SO$_4$, filtered and concentrated under reduced pressure. The crude material was purified by chromatography: ISCO 40 g silica with 25 g silica loader, eluting with 0-100/6 EtOAc/hexanes to give compound XVIII.

(R)-tert-Butyl (4-(2-(((tert-butoxycarbonyl)oxy)methyl) morpholino)phenyl)(6-(tributylstannyl)imidazo[1,2-a] pyrazin-8-yl)carbamate XIX: (R)-tert-Butyl (6-bromoimidazo[1,2-a]pyrazin-8-yl)(4-(2-(((tert-butoxycarbonyl)oxy) methyl)morpholino)phenyl)carbamate XVIII was reacted according to the analogous method of Example Intermediate 1.01 to provide (R)-tert-butyl (4-(2-(((tert-butoxycarbonyl) oxy)methyl)morpholino)phenyl)(6-(tributylstannyl)imidazo [1,2-a]pyrazin-8-yl)carbamate XIX.

(R)-tert-Butyl (6-(6-(bis(tert-butoxycarbonyl)amino) pyrazin-2-yl)imidazo[1,2-a]pyrazin-8-yl)(4-(2-(((tert-butoxycarbonyl)oxy)methyl)morpholino)phenyl)carbamate XX: (R)-tert-Butyl (4-(2-(((tert-butoxycarbonyl)oxy)methyl)morpholino)phenyl)(6-(tributylstannyl)imidazo[1,2-a]pyrazin-8-yl)carbamate XIX was reacted with 2-Bis(tert-butoxycarbonyl)amino-6-bromopyrazine XIV according to the analogous method of CHEMISTRY A as described in Example 2 to provide the desired compound (R)-tert-butyl (6-(6-(bis(tert-butoxycarbonyl)amino)pyrazin-2-yl)imidazo [1,2-a]pyrazin-8-yl)(4-(2-(((tert-butoxycarbonyl)oxy) methyl)morpholino)phenyl)carbamate XX.

(d, J=1.2 Hz, 1H), 8.06-7.90 (m, 2H), 7.87 (s, 1H), 7.62 (d, J=1.1 Hz, 1H), 7.05-6.93 (m, 2H), 6.49 (s, 2H), 4.78 (t, J=5.8 Hz, 1H), 3.98-3.87 (m, 1H), 3.71-3.36 (m, 7H), 2.63 (td, J=11.7, 3.4 Hz, 1H), 2.37 (dd, J=12.1, 10.5 Hz, 1H). The corresponding (S) isomer, or racemic mixture of compounds is prepared similarly, using (S)-(4-(4-aminophenyl)morpholin-2-yl)methanol or a racemic mixture of (4-(4-aminophenyl)morpholin-2-yl)methanol, respectively, in the first step.

Example 4. Preparation of 6-(6-aminopyrazin-2-yl)-5-methyl-N-(4-(4-(oxetan-3-yl)piperazin-1-yl)phenyl)imidazo[1,2-a]pyrazin-8-amine (4)

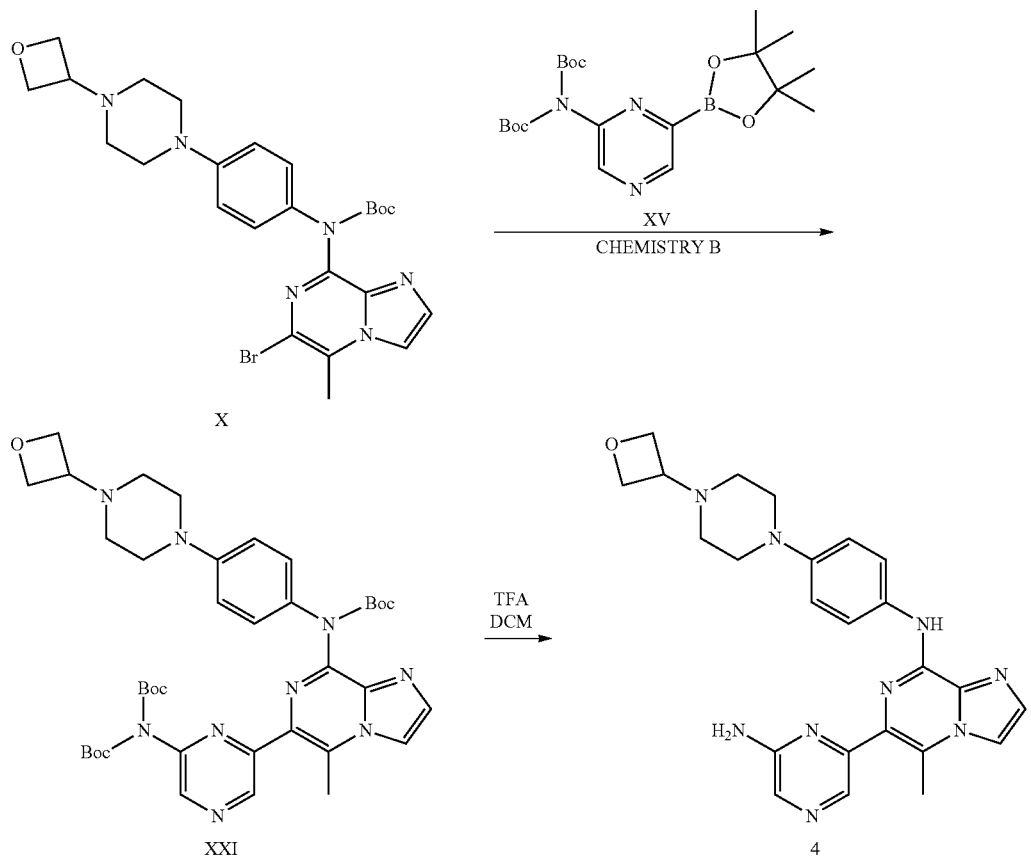

(R)-(4-(4-((6-(6-Amino-5-methylpyrazin-2-yl)imidazo[1,2-a]pyrazin-8-yl)amino)phenyl)morpholin-2-yl)methanol (3): (R)-tert-butyl (6-(6-(bis(tert-butoxycarbonyl)amino) pyrazin-2-yl)imidazo[1,2-a]pyrazin-8-yl)(4-(2-(((tert-butoxycarbonyl)oxy)methyl)morpholino)phenyl)carbamate XX (460 mg, 0.56 mmol) in DCM was added to a round bottom flask, and TFA (1.29 ml, 16.85 mmol) was added. The reaction was partially complete after stirring ~5 hours. Added an additional 10 eq TFA and stirred overnight, then concentrated under reduced pressure. 10% MeOH/DCM (~100 mL) and sat. aq. sodium bicarbonate were added and stirred 15 min, separated, extracted with ~100 mL 10% MeOH/DCM. The organic layers were combined, washed with brine, dried over $Na_2SO_4$, filtered and concentrated under reduced pressure and dried under vacuum. The resulting solid was triturated with DCM, collected solids via filtration and dried under vacuum to give compound 3. LCMS-ESI$^+$ (m % z): [M+H]$^+$: 419.2. $^1$H NMR (300 MHz d$_6$-DMSO) δ: 9.57 (s, 1H), 8.59 (s, 1H), 8.47 (s, 1H), 8.13 tert-Butyl (6-(6-(bis(tert-butoxycarbonyl)amino)pyrazin-2-yl)-5-methylimidazo[1,2-a]pyrazin-8-yl)(4-(4-(oxetan-3-yl)piperazin-1-yl)phenyl)carbamate XXI: tert-Butyl (6-bromo-5-methylimidazo[1,2-a]pyrazin-8-yl)(4-(4-(oxetan-3-yl)piperazin-1-yl)phenyl)carbamate X was reacted with XV according to the methods of CHEMISTRY B as described in Example 2 to provide the desired compound XXI.

6-(6-aminopyrazin-2-yl)-5-methyl-N-(4-(4-(oxetan-3-yl) piperazin-1-yl)phenyl)imidazo[1,2-a]pyrazin-8-amine (4): The compound tert-butyl (6-(6-(bis(tert-butoxycarbonyl) amino)pyrazin-2-yl)-5-methylimidazo[1,2-a]pyrazin-8-yl) (4-(4-(oxetan-3-yl)piperazin-1-yl)phenyl)carbamate XXI was de-protected by the analogous method described in Example 2 to provide the desired compound 4. LCMS-ESI$^+$ (m/z): [M+H]$^+$: 458.32. $^1$H NMR (300 MHz, d$_6$-DMSO) δ: 9.28 (s, 1H), 8.28 (s, 1H), 8.04 (s, 1H), 7.89 (d, 2H), 7.83 (s, 1H), 7.7 (s, 1H), 6.91 (d, 2H), 6.46 (s, 2H), 4.6-4.4 (dt, 4H), 3.43 (m, 1H), 3.1 (t, 4H), 2.49 (s, 3H), 2.4 (t, 4H).

Example 5. Preparation of 2-(5-((6-(6-aminopyrazin-2-yl)imidazo[1,2-a]pyrazin-8-yl)amino)-2-(4-(oxetan-3-yl)piperazin-1-yl)phenoxy)ethanol (5)
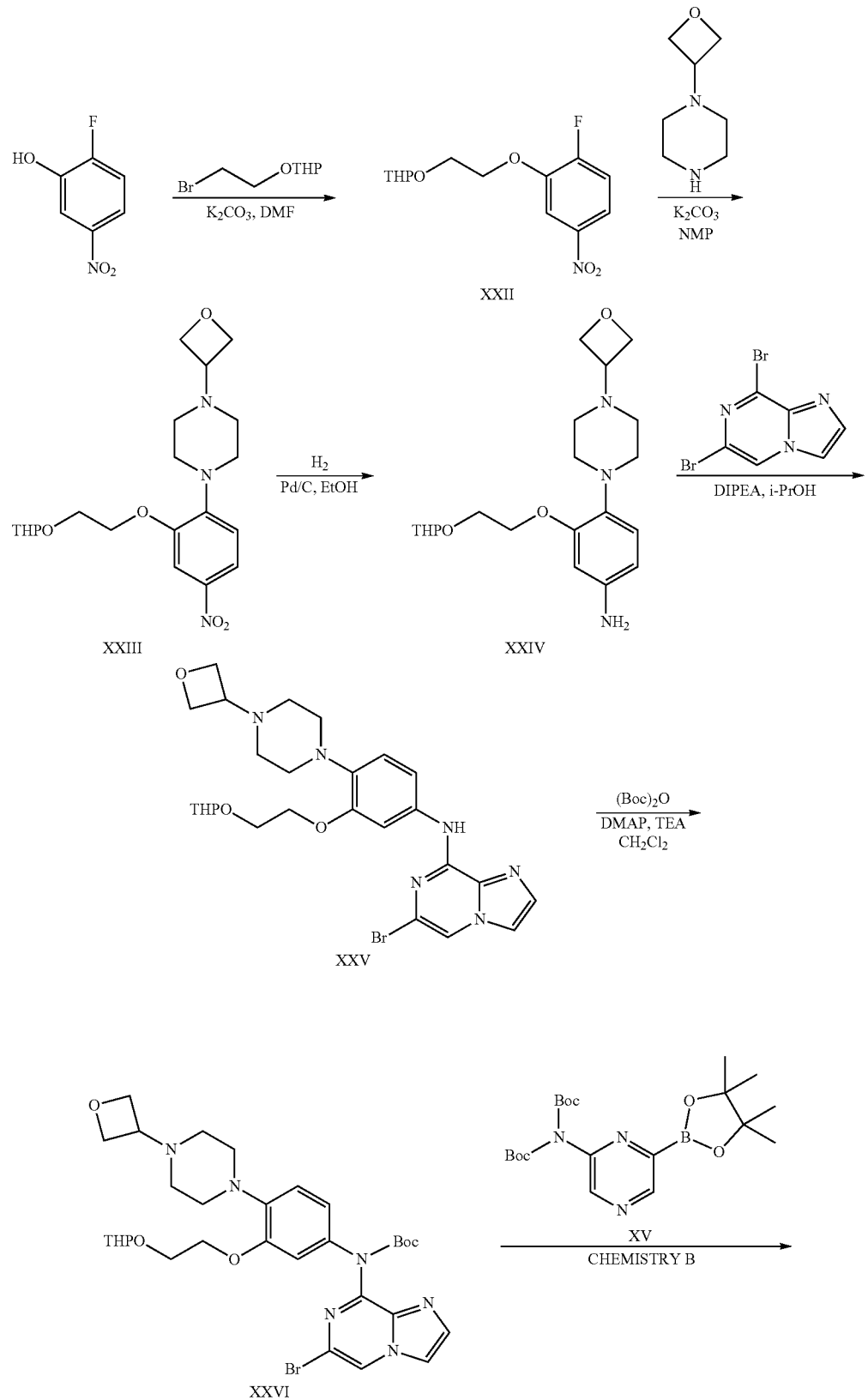

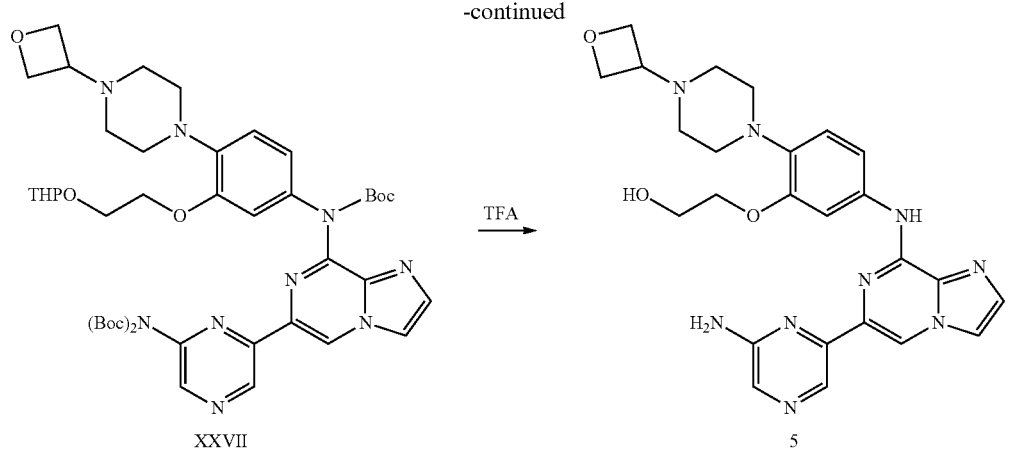

XXVII → 5

2-(2-(2-Fluoro-5-nitrophenoxy)ethoxy)tetrahydro-2H-pyran XXII: A mixture of 2-fluoro-5-nitrophenol (4 g, 25 mmol), 2-(2-bromoethoxy)tetrahydro-2H-pyran (4.4 mL, 28 mmol) and potassium carbonate (4.2 g 30 mmol) in DMF (50 mL) was stirred at 50° C. for 16 h. The reaction was cooled to room temperature, diluted with EtOAc and H₂O. The aqueous layer was separated and extracted with EtOAc. The combined organic extracts were washed with H₂O (5x's to remove DMF) and brine and dried over sodium sulfate. The resulting residue was purified by column chromatography ISCO Rf (40 g column) eluting with a gradient of 100% hexanes—1:1 hexanes:EtOAc to provide 2-(2-(2-fluoro-5-nitrophenoxy)ethoxy)tetrahydro-2H-pyran XXII. 1-(4-Nitro-2-(2-((tetrahydro-2H-pyran-2-yl)oxy)ethoxy)phenyl)-4-(oxetan-3-yl)piperazine XXIII: A mixture of 2-(2-(2-fluoro-5-nitrophenoxy)ethoxy)tetrahydro-2H-pyran XXII (1550 mg, 5.43 mmol), 1-(oxetan-3-yl)piperazine (772 mg, 5.43 mmol) and potassium carbonate (1126.41 mg, 8.15 mmol) in NMP (6 mL) was stirred at 100° C. for 8 h. The aqueous layer was separated and extracted with EtOAc. The combined organic extracts were washed with H2O (5× to remove NMP) and brine and dried over sodium sulfate. The resulting residue was purified by column chromatography ISCO Rf (24 g column) eluting with a gradient of 100% DCM—60:35:5 DCM:Et₂O:MeOH to provide 1-(4-nitro-2-(2-((tetrahydro-2H-pyran-2-yl)oxy)ethoxy)phenyl)-4-(oxetan-3-yl)piperazine XXIII.

4-(4-(Oxetan-3-yl)piperazin-1-yl)-3-(2-((tetrahydro-2H-pyran-2-yl)oxy)ethoxy)aniline XXIV: To a suspension of 1-(4-nitro-2-(2-((tetrahydro-2H-pyran-2-yl)oxy)ethoxy)phenyl)-4-(oxetan-3-yl)piperazine XXIII (2100 mg, 5.1 mmol) in ethanol (50 mL) was added 10% Pd/C (50% wet, 390 mg dry weight) in a 500-mL Parr hydrogenation bottle. The bottle was evacuated, charged with hydrogen gas to a pressure of 50 psi and shaken at rt for 2 h on a Parr hydrogenation apparatus. The reaction mixture was filtered, and washed with ethanol. The filtrate was concentrated in vacuo to give 4-(4-(oxetan-3-yl)piperazin-1-yl)-3-(2-((tetrahydro-2H-pyran-2-yl)oxy)ethoxy)aniline XXIV.

6-Bromo-N-(4-(4-(oxetan-3-yl)piperazin-1-yl)-3-(2-((tetrahydro-2H-pyran-2 yl)oxy)ethoxy)phenyl)imidazo[1,2-a]pyrazin-8-amine XXV: To a solution of 4-(4-(oxetan-3-yl)piperazin-1-yl)-3-(2-((tetrahydro-2H-pyran-2-yl)oxy)ethoxy)aniline XXIV (619 mg, 2.17 mmol) and 6,8-dibromoimidazo[1,2-a]pyrazine (601 mg, 2.2 mmol) in IPA (15 mL) was added N,N-Diisopropylethylamine (0.95 ml, 5.43 mmol). The mixture was stirred at 110° C. for 16 h. After this time, DCM (10 mL) and sat aqueous NaHCO₃ (15 mL) were added. The aqueous layer was separated and extracted with DCM (2×10 mL). The combined organic extracts were washed with brine (10 mL) and dried over sodium sulfate. The resulting residue was purified by column chromatography ISCO Rf (24 g column) eluting with a gradient of 100%/a DCM—60:35:5 DCM:Et₂O:MeOH to provide 6-bromo-N-(4-(4-(oxetan-3-yl)piperazin-1-yl)-3-(2-((tetrahydro-2H-pyran-2-yl)oxy)ethoxy)phenyl)imidazo[1,2-a]pyrazin-8-amine XXV.

tert-Butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI: 6-Bromo-N-(4-(4-(oxetan-3-yl)piperazin-1-yl)-3-(2-((tetrahydro-2H-pyran-2-yl)oxy)ethoxy)phenyl)imidazo[1,2-a]pyrazin-8-amine XXV (1.2 g, 2.4 mmol) was reacted according to the analogous method described in Intermediate Example 1.01 (conversion of III to IV) to provide tert-butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI.

tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVII: tert-Butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI was reacted with XV according to the methods of CHEMISTRY B as described in Example 2 to provide the desired compound tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVII.

2-(5-((6-(6-aminopyrazin-2-yl)imidazo[1,2-a]pyrazin-8-yl)amino)-2-(4-(oxetan-3-yl)piperazin-1-yl)phenoxy)ethanol (5): The compound tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVII (313 mg, 0.35 mmol) was de-protected by the analogous method described in Example 2 to provide 2-(5-((6-(6-aminopyrazin-2-yl)imidazo[1,2-a]pyrazin-8-yl)amino)-2-(4-(oxetan-3-yl)piperazin-1-yl)phenoxy)ethanol (5). LCMS-ESI⁺ (m/z): [M+H]⁺: 504.3. ¹H NMR (300 MHz, d₆-DMSO) δ: 9.52 (s, 1H), 8.61 (s, 1H), 8.51 (s, 1H), 8.14 (d, J=1.1 Hz, 1H), 7.89 (s, 1H), 7.81 (d, J=2.3 Hz, 1H), 7.74-7.60 (m, 2H), 6.90 (d, J=8.6 Hz, 1H), 6.47 (s, 2H), 5.74 (s, 1H), 4.86-4.76 (m, 1H), 4.50 (dt, J=25.6, 6.3 Hz, 4H), 4.04 (t, J=5.1 Hz, 2H), 3.73 (q, J=5.1 Hz, 2H), 3.51-3.42 (m, 1H), 3.02 (s, 4H), 2.40 (s, 4H).

Example 6. Preparation of 2-((4-(4-((6-(6-aminopyrazin-2-yl)imidazo[1,2-a]pyrazin-8-yl)amino)phenyl)piperazin-1-yl)methyl)propane-1,3-diol (6)
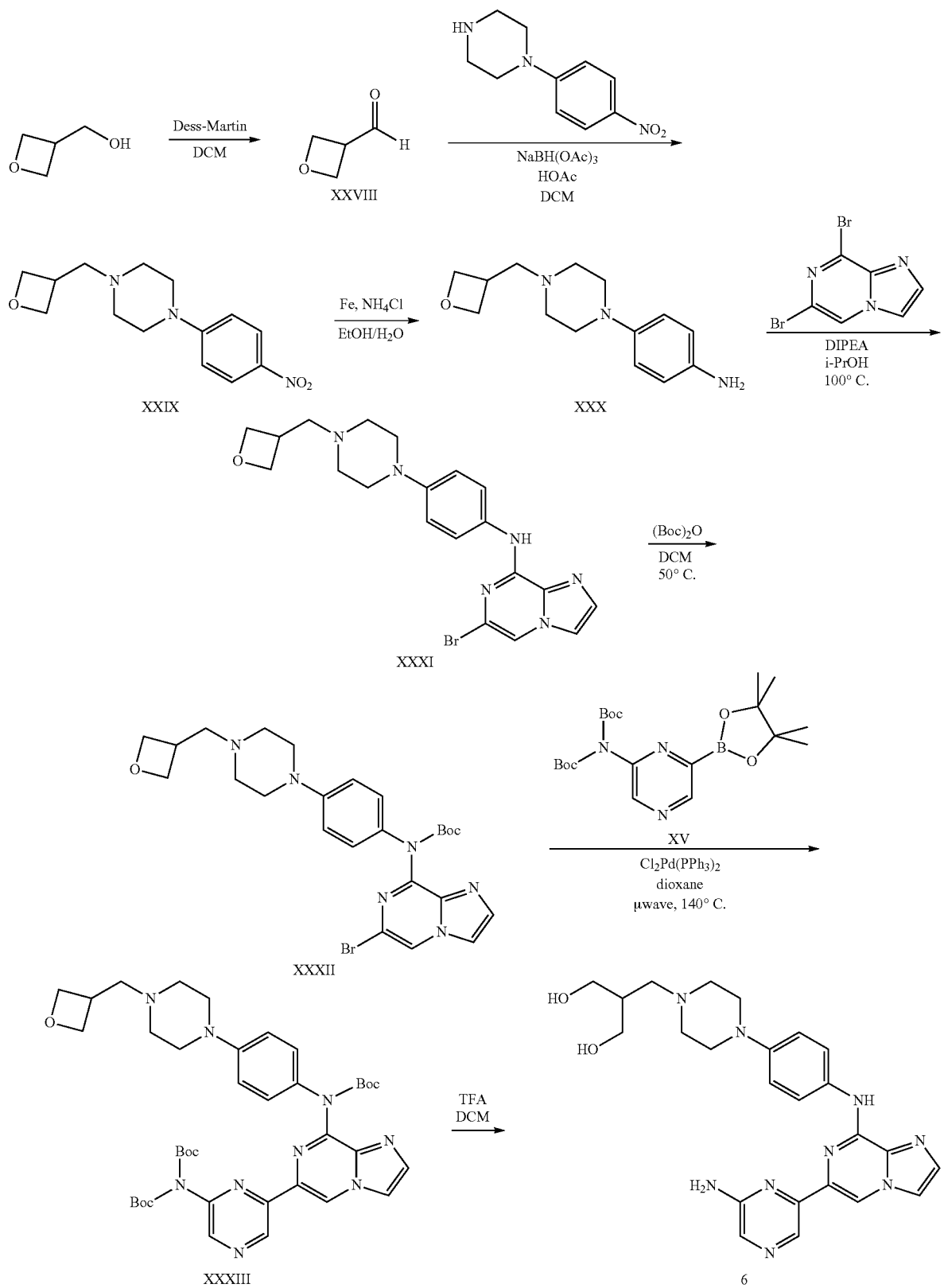

Oxetane-3-carbaldehyde XXVIII: To a round-bottomed flask equipped with a stirring bar, oxetan-3-ylmethanol (2.00 g, 22.7 mmol) was dissolved in DCM (50 mL) and Dess-Martin periodinane (10.67 g, 28.38 mmol) was added in one portion. The reaction mixture was stirred at RT overnight. The solids were filtered through celite, and washed with DCM (3 mL×5). The filtrate was removed and concentrated in vacuo and the resulting crude oxetane-3-carbaldehyde XXVIII was used in the next step directly.

1-(4-Nitrophenyl)-4-(oxetan-3-ylmethyl)piperazine XXIX: To a round-bottomed falsk equipped with a stirring bar, oxetane-3-carbaldehyde XXVIII (0.977 g, 11.35 mmol), 1-(4-nitrophenyl)piperazine (1.18 g, 5.68 mmol) in DCM (100 mL), and HOAc (1.70 g, 28.38 mmol) in DCM (2 mL) were added. After 5 minutes, NaBH(OAc)$_3$ (24.06 g, 113.05 mmol) was added. The resulting mixture was stirred at room temperature for 2 h. Most volatiles were removed in vacuo. DCM (200 mL) was added, followed by saturated NaHCO$_3$ aqeuous solution (20 mL), and the resulting mixture was stirred for 20 minutes. The organic phase was separated and washed with saturated NaHCO$_3$ aqueous solution (20 mL×3), brine (20 mL×1), dried over Na$_2$SO$_4$, filtered and solvents were removed in vacuo. The residue was passed through a silica gel column (MeOH: DCM=0:100 to 5:95 to 25:75) to provide the desired compound XXIX.

4-(4-(Oxetan-3-ylmethyl)piperazin-1-yl)aniline XXX: To a round-bottomed flask equipped with a stirring bar, were added 1-(4-nitrophenyl)-4-(oxetan-3-ylmethyl)piperazine XXIX (3.20 g, 11.54 mmol), ethanol (60 mL) and water (60 mL). Following the addition of iron (4.51 g, 80.77 mmol) and ammonium chloride (4.32 g, 80.77 mmol), the reaction mixture was heated at 80° C. for 1 h, then filtered through Celite and washed with DCM (5 mL×5). The resulting filtrate was extracted with DCM (20 ml×3). The combined organic extracts were washed with water (20 mL×2), brine (20 mL×1), dried over Na$_2$SO$_4$, and concentrated in vacuo. The desired 4-(4-(oxetan-3-ylmethyl)piperazin-1-yl)aniline XXX was obtained.

6-Bromo-N-(4-(4-(oxetan-3-ylmethyl)piperazin-1-yl)phenyl)imidazo[1,2-a]pyrazin-8-amine XXXI: To a seal tube equipped with a stirring bar, 4-(4-(oxetan-3-ylmethyl)piperazin-1-yl)aniline XXX (1.19 g, 4.81 mmol), 6,8-dibromoimidazo[1,2-a]pyrazine (1.33 g, 4.81 mmol), isopropanol (24.1 mL), and diisopropylethylamine (1.37 g, 10.58 mmol) were added, and the reaction mixture was heated at 100° C. overnight. Most solvents were removed in vacuo and DCM (200 mL) was added to the mixture. The solution was washed with H$_2$O (20 mL×2), brine (20 mL×1), dried over Na$_2$SO$_4$, filtered and solvents were removed in vacuo. The resulting residue was passed through a silica gel column (MeOH:DCM=5:95) and light red solids were obtained as the desired compound XXXI, 0.692 g.

tert-Butyl (6-bromoimidazo[1,2-a]pyrazin-8-yl)(4-(1-(oxetan-3-ylmethyl)piperidin-4-yl)phenyl)carbamate XXXII: To a round-bottomed flask equipped with a stirring bar, were added 6-bromo-N-(4-(4-(oxetan-3-ylmethyl)piperazin-1-yl)phenyl)imidazo[1,2-a]pyrazin-8-amine XXXI (560 mg, 1.27 mmol), DCM (11 mL), di-tert-butyl dicarbonate (414.4 mg, 1.90 mmol), and triethylamine (640.5 mg, 6.33 mmol). The reaction mixture was heated at 50° C. overnight. DCM (200 mL) was added, and the resulting solution was washed with water (20 mL×2), brine (20 mL×1), dried over Na$_2$SO$_4$, filtered and solvents were removed in vacuo. Column chromatography gave the desired compound XXXII as yellow solids.

tert-Butyl (6-(6-(bis(tert-butoxycarbonyl)amino)pyrazin-2-yl)imidazo[1,2-a]pyrazin-8-yl)(4-(4-(oxetan-3-ylmethyl)piperazin-1-yl)phenyl)carbamate XXXIII: To a round-bottomed flask equipped with a stirring bar, tert-butyl (6-bromoimidazo[1,2-a]pyrazin-8-yl)(4-(4-(oxetan-3-ylmethyl)piperazin-1-yl)phenyl)carbamate XXXII (150 mg, 0.276 mmol), N, N-BisBoc 6-(4,4,5,5-tetramethyl-1,3,2-dioxaborolan-2-yl)pyrazin-2-amine XV (255.8 mg, 0.607 mmol) in DME (2.3 mL), Pd(PPh$_3$)$_4$ (16.0 mg, 0.14 mmol), Na$_2$CO$_3$ aqueous solution (1.0 N, 0.91 mL, 0.91 mmol), and DME (2 mL) were added. The mixture was heated at 75° C. for 2, then DCM (200 mL) was added and the resulting mixture was washed with water (30 mL×3), brine (30 mL×1), dried over MgSO$_4$, filtered, and solvents were removed in vacuo. Purification by silica gel column (MeOH: DCM=5:95) gave the desired compound XXXIII.

2-((4-(4-((6-(6-aminopyrazin-2-yl)imidazo[1,2-a]pyrazin-8-yl)amino)phenyl)piperazin-1-yl)methyl)propane-1,3-diol (6): To a solution of tert-butyl (6-(6-(bis(tert-butoxycarbonyl)amino)pyrazin-2-yl)imidazo[1,2-a]pyrazin-8-yl)(4-(4-(oxetan-3-ylmethyl)piperazin-1-yl)phenyl)carbamate XXXIII (250 mg, 0.33 mmol) in DCM (30 mL) was added TFA (940.3 mg, 8.25 mmol). The resulting mixture was stirred at room temperature for overnight. More TFA (752.2 mg, 6.60 mmol) was added and stirred at room temperature overnight. Most solvents were removed in vacuo, DCM (200 mL) and saturated NaHCO$_3$ aqueous solution (30 mL) were added and the resulting mixture was stirred for 30 minutes. The organic phase was separated, washed with saturated NaHCO$_3$ aqueous solution (20 mL×4), brine (20 mL×1). The aqueous phase was extracted with DCM (30 mL×2). The combined organic phases were washed with brine (20 mL×1), dried over Na$_2$SO$_4$, filtered, and solvents were removed in vacuo. The crude material was purified on ISCO column, MeOH:DCM=0:100 to 5:95 to 7.5:92.5 to 25:75 to elute the desired compounds. Two compounds were obtained, the first is the oxetane compound; and the other the desired compound 6. LCMS-ESI$^+$ (m/z): [M+H]$^+$: 476. $^1$H NMR (300 MHz, d$_6$-DMSO) δ: 9.51 (s, 1H), 8.60 (s, 1H), 8.49 (s, 1H), 8.14 (d, J=1.5 Hz, 1H), 7.95 (d, J=9 Hz, 2H), 7.90 (s, 1H), 7.64 (s, 1H), 6.99 (d, J=9 Hz, 2H), 6.48 (s, 2H), 4.51 (broad S, 2H), 3.43 (d, J=6 Hz, 4H), 3.12 (broad m, 4H), 2.54 (broad m, 4H), 2.34 (d, J=7.2 Hz, 2H), 1.83 (m, 1H).

Example 7. Preparation of 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol (7)

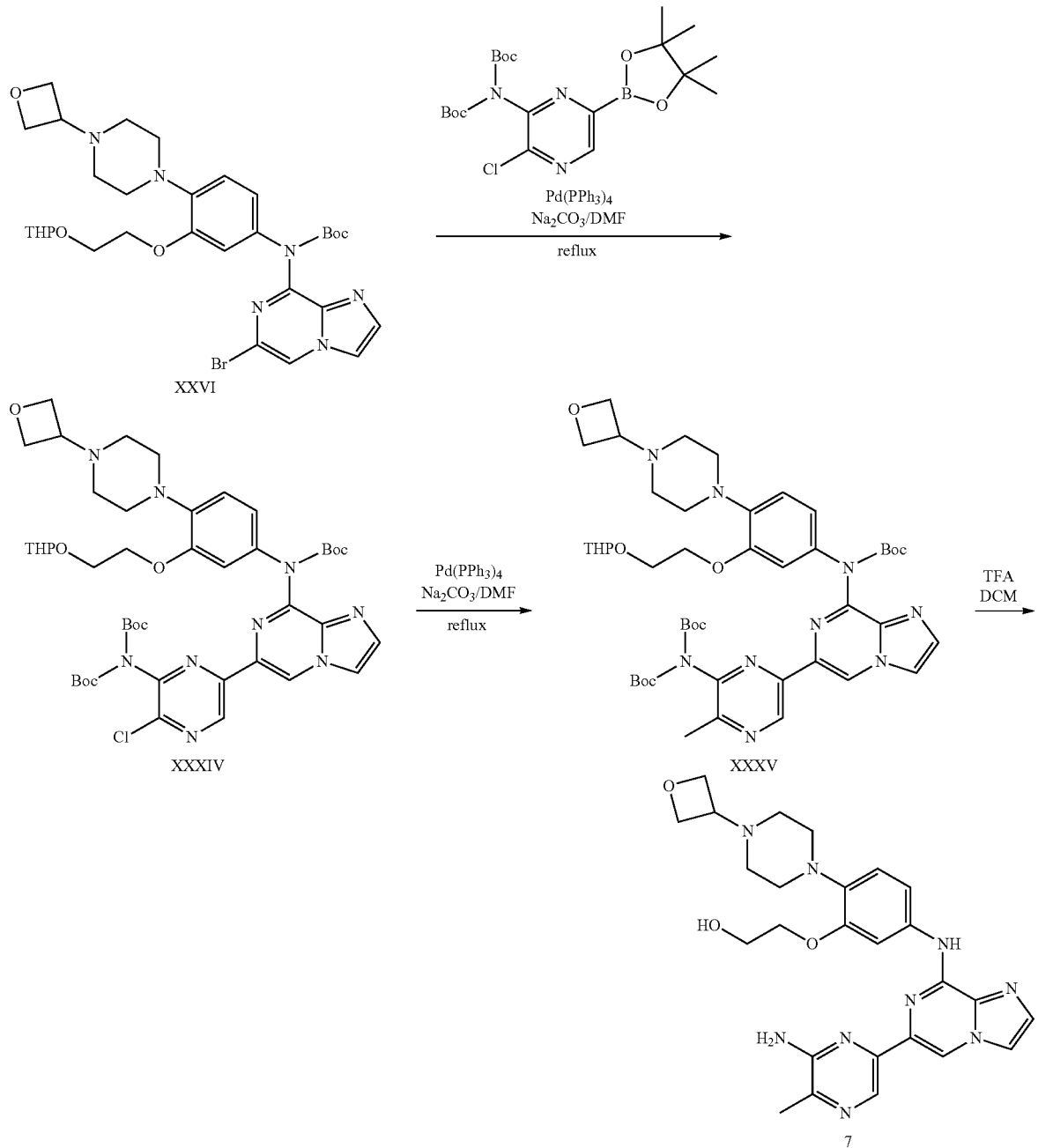

tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-chloropyrazin-2-yl)carbamate XXXIV: A flask equipped with a reflux condenser was charged with tert-butyl (6-bromoimidazo[1,2-a]pyrazin-8-yl)(4-(4-(oxetan-3-yl)piperazin-1-yl)-3-(2-((tetrahydro-2H-pyran-2-yl)oxy)ethoxy)phenyl)carbamate XXVI (prepared as described in Example 5) (352 mg, 0.52 mmol), 2-(bis-boc-amino)-3-chloro-6-(4,4,5,5-tetramethyl-1,3,2-dioxaborolan-2-yl)pyrazine (prepared by analogous method as used in Example 2 for the preparation of compound XV) (500 mg, 1.1 mmol), Pd(PPh$_3$)$_4$ (30 mg, 0.03 mmol) in sodium carbonate (1.6 mL, 1M in H$_2$O) and DME (4.8 mL). The mixture was heated to reflux for 1 h. The reaction was cooled to room temperature, diluted with DCM and H$_2$O. The aqueous layer was separated and extracted with DCM. The combined organic extracts were washed with brine, dried over sodium sulfate, filtered and concentrated under reduced pressure. The resulting residue was purified by column chromatography ISCO Rf (4 g column) eluting with a gradient of 100% DCM—100% 60/35/5 DCM/Et$_2$O/MeOH, appropriate fractions were combined and concentrated to provide the desired compound tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy) phenyl)amino)imidazo[1,2-a]pyrazin-6-yl)-3-chloropyrazin-2-yl)carbamate XXXIV.

tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-methylpyrazin-2-yl)carbamate XXXV: A microwave vial was charged with tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy) phenyl)amino)imidazo[1,2-a]pyrazin-6-yl)-3-chloropyrazin-2-yl)carbamate XXXIV (258 mg, 0.28 mmol), methylboronic acid (503 mg, 8.4 mmol), Pd(PPh$_3$)$_4$ (32 mg, 0.03 mmol) in sodium carbonate (0.8 mL, 1M in H$_2$O) and DME (2.5 mL). The mixture was heated at 150° C. for 20 min. The reaction was cooled to room temperature, diluted with DCM and H$_2$O. The aqueous layer was separated and extracted with DCM. The combined organic extracts were washed with brine, dried over sodium sulfate, filtered and concentrated under reduced pressure. The resulting residue was purified by column chromatography ISCO Rf (4 g column) eluting with a gradient of 100% DCM—100% 75/18/7 DCM/Et$_2$O/MeOH to provide the desired compound tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy)ethoxy)phenyl)amino)imidazo[1,2-a]pyrazin-6-yl)-3-methylpyrazin-2-yl)carbamate XXXV.

2-(5-((6-(6-Amino-5-methylpyrazin-2-yl)imidazo[1,2-a]pyrazin-8-yl)amino)-2-(4-(oxetan-3-yl)piperazin-1-yl)phenoxy)ethanol (7): To a solution of tert-butyl tert-butoxycarbonyl(6-(8-((tert-butoxycarbonyl)(4-(4-(oxetan-3-yl)piperazin-1-yl)-3-(2-((tetrahydro-2H-pyran-2-yl)oxy) ethoxy)phenyl)amino)imidazo[1,2-a]pyrazin-6-yl)-3-methylpyrazin-2-yl)carbamate XXXV (165 mg, 0.18 mmol) in DCM (2.2 mL) was added TFA (1.1 mL, 0.11 mmol). The mixture was stirred at rt for 16 h. The reaction was diluted with 9:1 DCM:MeOH and H$_2$O. The aqueous layer was separated and extracted with 9:1 DCM:MeOH. The combined organic extracts were washed with brine, dried over sodium sulfate, filtered and concentrated under reduced pressure. The resulting residue was purified by column chromatography eluting with a gradient of 100% 75/18/7 DCM/Et$_2$O/MeOH—100% 70/20/10 DCM/Et$_2$O/MeOH to provide the desired compound 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol (7, 56 mg, 59%). LCMS-ESI$^+$ (m/z): [M+H]$^+$: 518.2. $^1$H NMR (300 MHz, d$_6$-DMSO) δ: 9.49 (s, 1H), 8.56 (s, 1H), 8.44 (s, 1H), 8.13 (d, J=1.1 Hz, 1H), 7.85-7.66 (m, 2H), 7.62 (d, J=1.1 Hz, 1H), 6.90 (d, J=8.6 Hz, 1H), 6.25 (s, 2H), 4.87-4.77 (m, 1H), 4.50 (dt, J=25.2, 6.3 Hz, 4H), 4.04 (t, J=5.1 Hz, 2H), 3.74 (q, J=5.2 Hz, 2H), 3.51-3.39 (m, 1H), 3.10-2.95 (m, 4H), 2.45-2.35 (m, 4H), 2.34 (s, 3H). Alternatively, compound XXXIV could be taken directly to this step and similarly de-protected to provide the 5-chloropyrazine substituted analog.

Monomesylate and Succinate Forms

X-ray powder diffraction (XRPD) analysis of the monomesylate (MSA) and succinate forms of the compound of Example 2 herein were conducted on a diffractometer (PANanalytical XPERT-PRO, PANalytical B.V., Almelo, Netherlands) using copper radiation (Cu Kα, λ=1.5418 Å). Samples were prepared for analysis by depositing the powdered sample in the center of an aluminum holder equipped with a zero background plate. The generator was operated at a voltage of 45 kV and amperage of 40 mA. Slits used were Soller 0.02 rad., antiscatter 1.0°, and divergence. The sample rotation speed was 2 sec. Scans were performed from 2 to 40° 2-theta. Data analysis was performed by X'Pert Highscore version 2.2c (PANalytical B.V., Almelo, Netherlands) and X'Pert data viewer version 1.2 d (PANalytical B.V., Almelo, Netherlands). The XRPD patterns for Mono MSA Forms I & II were obtained using the instrument setting as follows: 45 KV, mA, Cu Kα, λ=1.5418 Å, scan range 2.–40°, step size 0.0167°, counting time: 15.875 s. The XRPD patterns for Succinate Forms I & II were obtained using the instrument setting as follows: 45 KV, 40 mA, Cu Kα, λ=1.5418 Å, scan range 2.–40°, step size 0.0084°, counting time: 95.250 s.

$^1$H NMR spectra of the monomesylate (MSA) and succinate forms of the compound of Example 2 were collected on a Varian 400-MR 400 MHz instrument with 7620AS sample changer. The default proton parameters are as follows: spectral width: 14 to −2 ppm (6397.4 Hz); relaxation delay: 1 sec; acquisition time: 2.5559 sec; number of scans or repetitions: 8; temperature: 25 C. Samples were prepared in dimethyl sulfoxide-d$_6$, unless otherwise stated. Off-line analysis was carried out using MNova software.

Example 8—6-(6-aminopyrazin-2-yl)-N-(4-(4-(oxetan-3-yl)piperazin-1-yl)phenyl)imidazo[1,2-a] pyrazin-8-amine monomesylate Form I Methanesulfonic acid (MSA) salt Form I was prepared by dissolving 6-(6-aminopyrazin-2-yl)-N-(4-(4-(oxetan-3-yl) piperazin-1-yl)phenyl)imidazo[1,2-a]pyrazin-8-amine (Example 2) in 11 volumes of acetone/H$_2$O (36:64 vol. %) with 1 molar equivalent of methane sulfonic acid (MSA) at room temperature. The solution was then charged with 19 volumes of acetone over 1 hour and the reactor contents were stirred at room temperature overnight.

XRPD analysis of 6-(6-aminopyrazin-2-yl)-N-(4-(4-(oxetan-3-yl)piperazin-1-yl)phenyl)imidazo[1,2-a]pyrazin-8-amine monomesylate Form I was conducted as described above and provided the diffraction pattern seen in FIG. 1, with the peaks in the table below.

| No. | Pos. [°2Th.] | Rel. Int. [%] |
|---|---|---|
| 1 | 19.6606 | 100 |
| 2 | 17.2746 | 93.07 |
| 3 | 17.8971 | 69.96 |
| 4 | 21.6306 | 65.74 |
| 5 | 25.7805 | 59.16 |
| 6 | 18.7593 | 51.5 |
| 7 | 13.7252 | 48.77 |
| 8 | 15.7206 | 41.91 |
| 9 | 24.7364 | 38.09 |
| 10 | 18.4345 | 36.84 |

In one embodiment 6-(6-aminopyrazin-2-yl)-N-(4-(4-(oxetan-3-yl)piperazin-1-yl)phenyl)imidazo[1,2-a]pyrazin-8-amine monomesylate Form I may be characterized by XRPD peaks 19.7 (19.6606), 17.3 (17.2746), 17.9 (17.8971), 21.6 (21.6306), and 25.8 (25.7805). In a further embodiment 6-(6-aminopyrazin-2-yl)-N-(4-(4-(oxetan-3-yl) piperazin-1-yl)phenyl)imidazo[1,2-a]pyrazin-8-amine monomesylate Form I may be characterized by XRPD peaks 19.7 (19.6606), 17.3 (17.2746), 17.9 (17.8971), and 21.6 (21.6306). In another embodiment 6-(6-aminopyrazin-2-yl)-N-(4-(4-(oxetan-3-yl)piperazin-1-yl)phenyl)imidazo[1,2-a] pyrazin-8-amine monomesylate Form I may be characterized by XRPD peaks 6.0, 6.2, 8.6, and 9.6.

Figure 2:
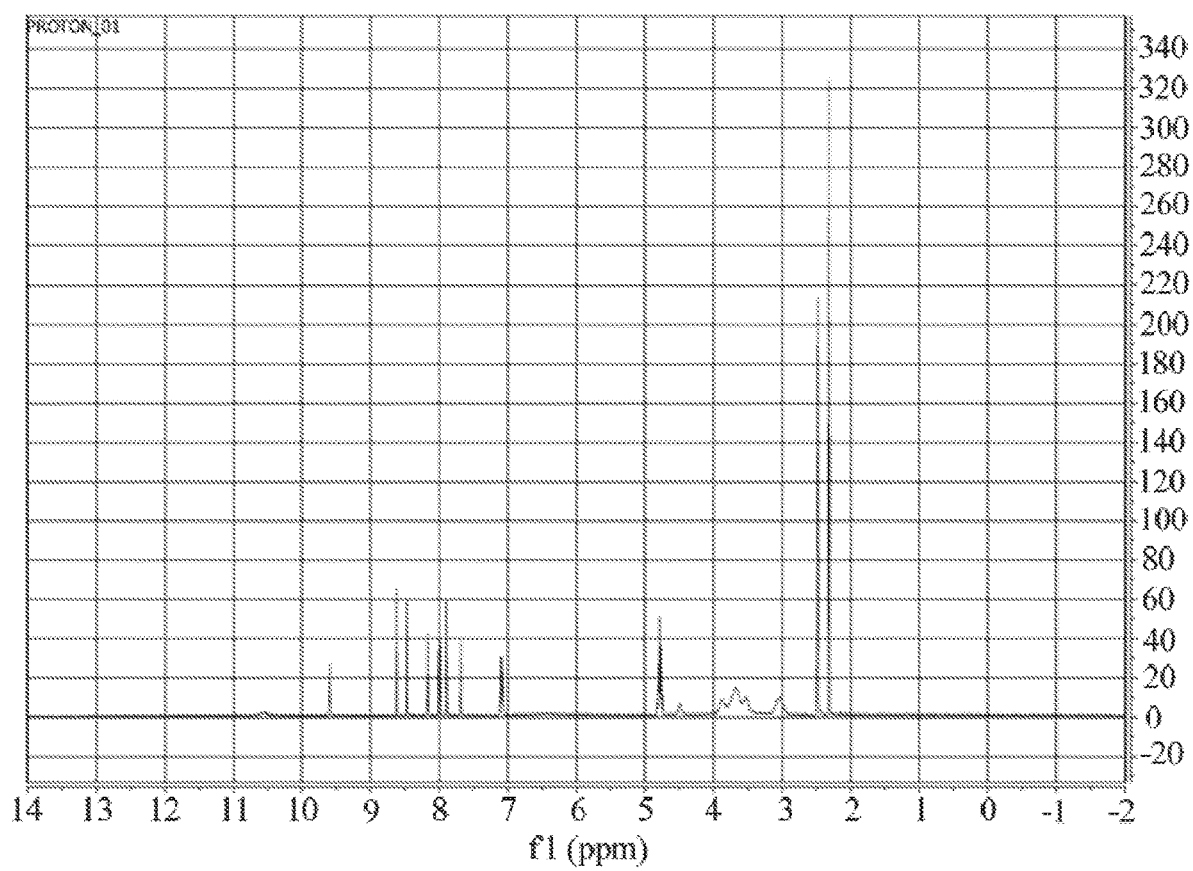
FIG. 2 is an NMR Analysis of Mono MSA Salt Form I of the compound of Example 2.

NMR Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I, conducted as described above, provided the NMR spectrum seen in FIG. 2.

$^1$H NMR (400 MHz, DMSO-d$_6$) δ 10.57 (s, 1H), 9.60 (s, 1H), 8.62 (s, 1H), 8.47 (s, 1H), 8.17 (d, J=1.2 Hz, 1H), 8.03-7.96 (m, 2H), 7.90 (s, 1H), 7.69 (d, J=1.2 Hz, 1H), 7.09 (d, J=9.0 Hz, 2H), 4.78 (p, J=8.0 Hz, 4H), 4.49 (m, 1H), 4.00-2.8 (m, 10H), 2.32 (s, 3H).

Differential scanning calorimetry (DSC): DSC was performed for each of the examples indicated herein using a TA Instruments Q2000 DSC instrument. The sample was placed into an aluminum DSC pan, and the weight accurately recorded. The pan was covered with a lid, and then either crimped or hermetically sealed. The same cell was heated under a nitrogen purge at a rate of 10° C./min, up to a final temperature of 300° C. Indium was used as the calibration standard.

Figure 3:
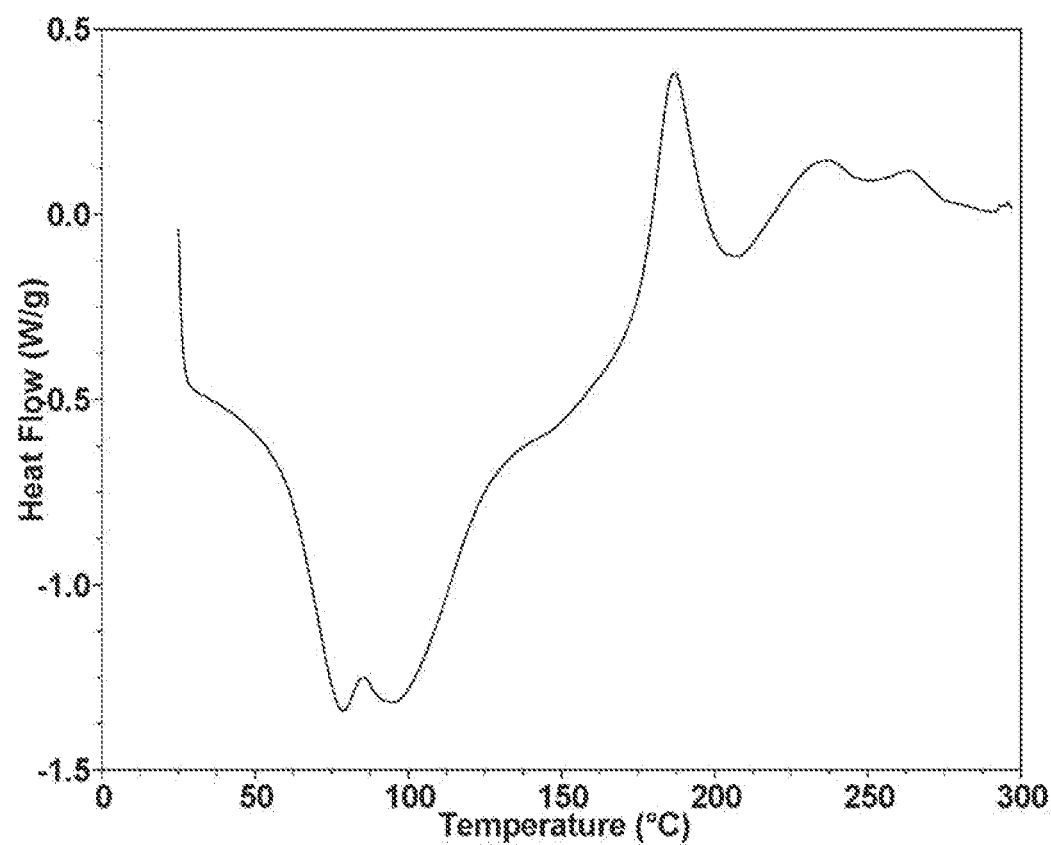
FIG. 3 is a DSC Analysis of Mono MSA Salt Form I of the compound of Example 2.

A DSC analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I, conducted as described above, is seen in FIG. 3.

Thermogravimetric analysis (TGA): TGA was performed for each of the examples indicated herein using a TA Instruments Q5000 TGA instrument. Each sample was placed in an aluminum sample pan and inserted into the TG furnace. The furnace was heated under nitrogen at a rate of 10° C./min, up to a final temperature of 300° C. The TGA furnace was calibrated using the magnetic Curie point method.

Figure 4:
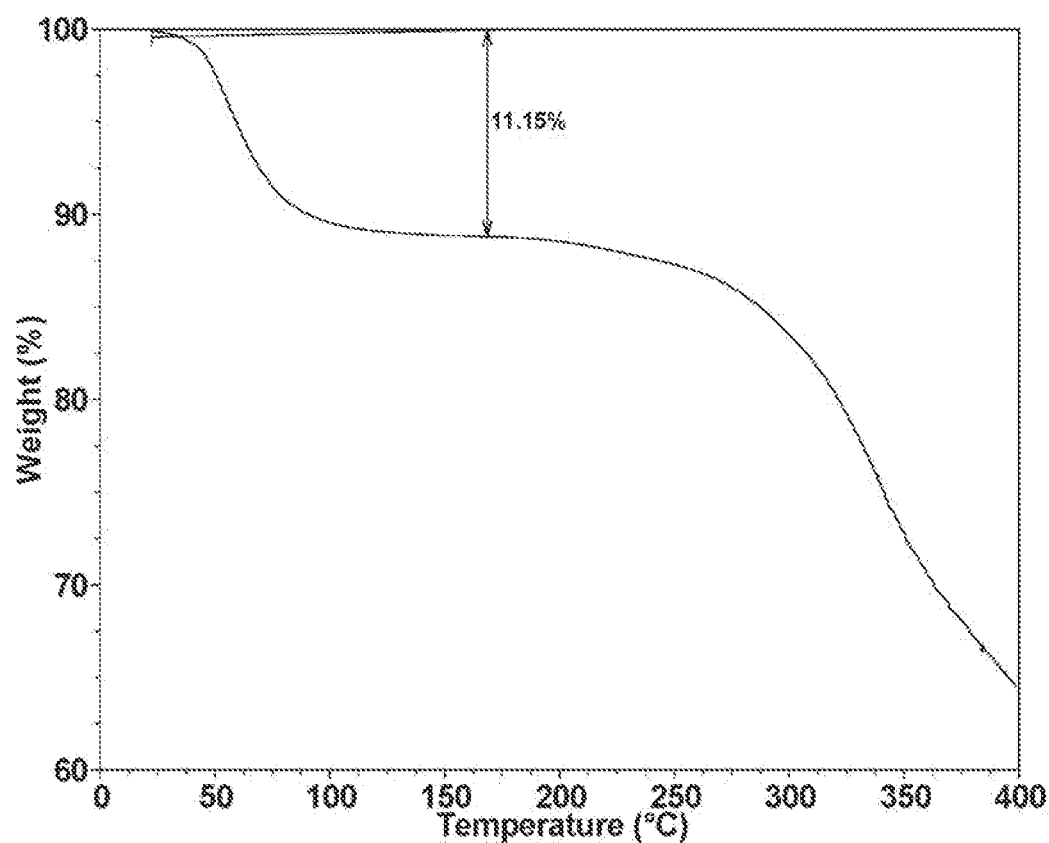
FIG. 4 is a TGA Analysis of Mono MSA Salt Form I of the compound of Example 2.

A TGA analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form I, conducted as described above, is seen in FIG. 4.

Example 9—6-(6-aminopyrazin-2-yl)-N-(4-(4-(oxetan-3-yl)piperazin-1-yl)phenyl)imidazo[1,2-a]pyrazin-8-amine monomesylate Form II 6-(6-aminopyrazin-2-yl)-N-(4-(4-(oxetan-3-yl)piperazin-1-yl)phenyl)imidazo[1,2-a]pyrazin-8-amine Mono MSA Salt Form II was prepared by drying 6-(6-aminopyrazin-2-yl)-N-(4-(4-(oxetan-3-yl)piperazin-1-yl)phenyl)imidazo[1,2-a]pyrazin-8-amine Mono MSA Salt Form I (Example 8) in a vacuum oven at ~40° C. with a N$_2$ purge.

Figure 5:
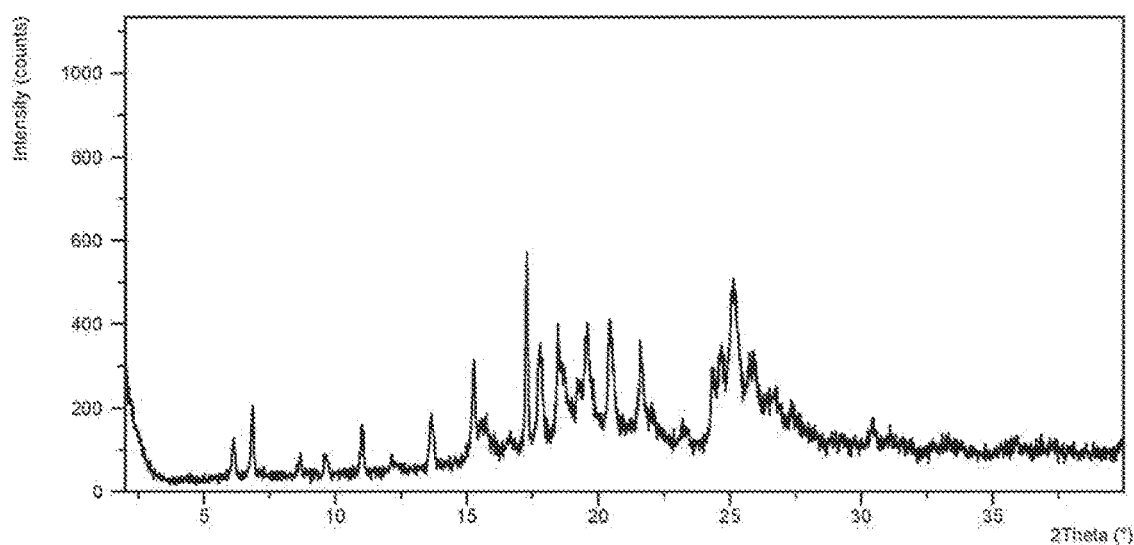
FIG. 5 is an XRPD Analysis Mono MSA Salt Form II of the compound of Example 2.

XRPD analysis of 6-(6-aminopyrazin-2-yl)-N-(4-(4-(oxetan-3-yl)piperazin-1-yl)phenyl)imidazo[1,2-a]pyrazin-8-amine monomesylate Form II was conducted as described above and provided the diffraction pattern seen in FIG. 5, with the peaks in the table below.

| No. | Pos. [°2Th.] | Rel. Int. [%] |
|---|---|---|
| 1 | 17.2698 | 100 |
| 2 | 25.1384 | 67.84 |
| 3 | 20.4423 | 63.66 |
| 4 | 19.5732 | 62.11 |
| 5 | 18.5264 | 50.36 |
| 6 | 17.7884 | 50.07 |
| 7 | 21.6273 | 45.52 |
| 8 | 15.2397 | 44 |
| 9 | 6.855 | 35.01 |
| 10 | 13.65 | 26 |

In one embodiment 6-(6-aminopyrazin-2-yl)-N-(4-(4-(oxetan-3-yl)piperazin-1-yl)phenyl)imidazo[1,2-a]pyrazin-8-amine monomesylate Form TI may be characterized by XRPD peaks 17.3 (17.2698), 25.1 (25.1384), 20.4 (20.4423), 19.6 (19.5732), and 18.5 (18.5264). In an additional embodiment 6-(6-aminopyrazin-2-yl)-N-(4-(4-(oxetan-3-yl)piperazin-1-yl)phenyl)imidazo[1,2-a]pyrazin-8-amine monomesylate Form II may be characterized by XRPD peaks 17.3 (17.2698), 25.1 (25.1384), 20.4 (20.4423), and 19.6 (19.5732). In another embodiment 6-(6-aminopyrazin-2-yl)-N-(4-(4-(oxetan-3-yl)piperazin-1-yl)phenyl)imidazo[1,2-a]pyrazin-8-amine monomesylate Form II may be characterized by XRPD peaks 6.1, 6.9, 11.0, and 13.6.

Figure 6:
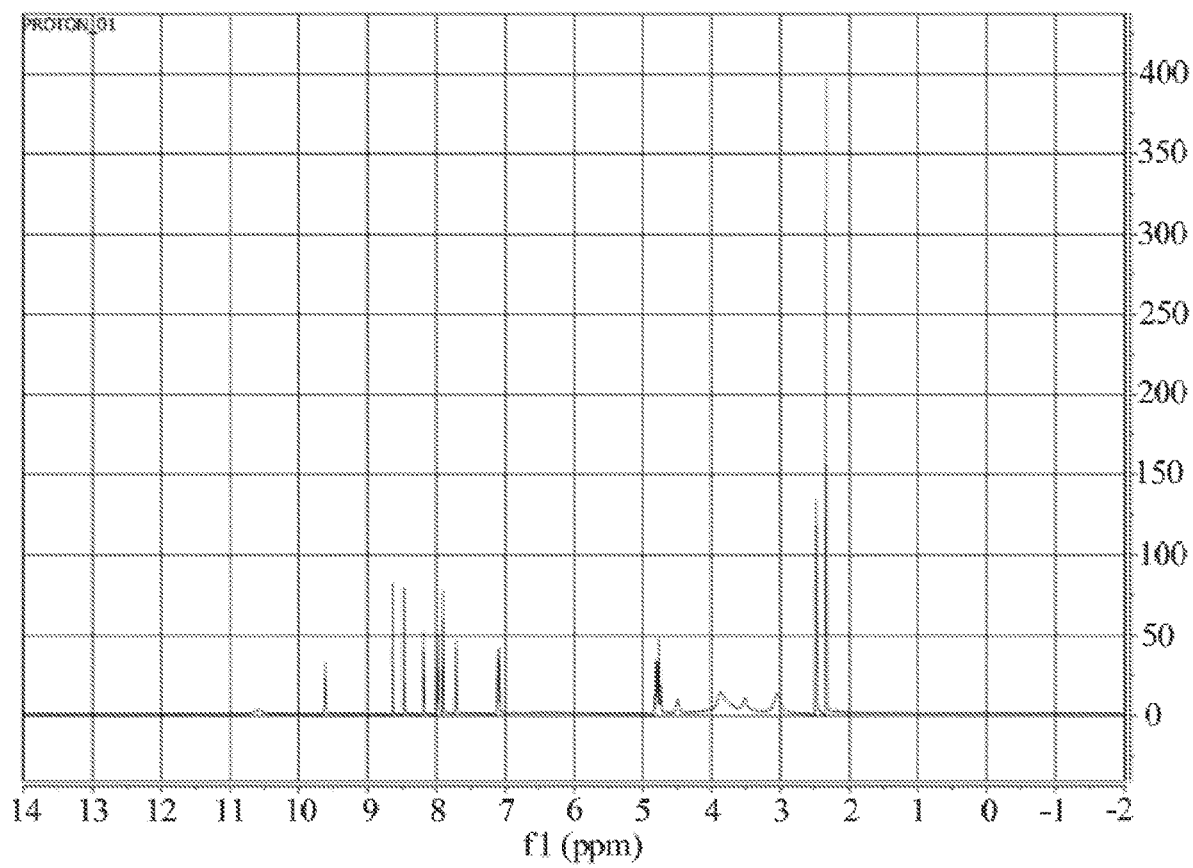
FIG. 6 is an NMR Analysis Mono MSA Salt Form II of the compound of Example 2.

NMR Analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II, conducted as described above, provided the NMR spectrum seen in FIG. 6.

$^1$H NMR (400 MHz, DMSO-d$_6$) δ 9.61 (s, 1H), 8.63 (s, 1H), 8.47 (s, 1H), 8.19 (d, J=1.2 Hz, 1H), 8.02-7.95 (m, 2H), 7.91 (s, 1H), 7.72 (d, J=1.2 Hz, 1H), 7.13-7.06 (m, 2H), 4.85-4.72 (m, 4H), 4.53-4.45 (m, 1H), 4.30-2.75 (m, 10H), 2.34 (s, 3H).

Figure 7:
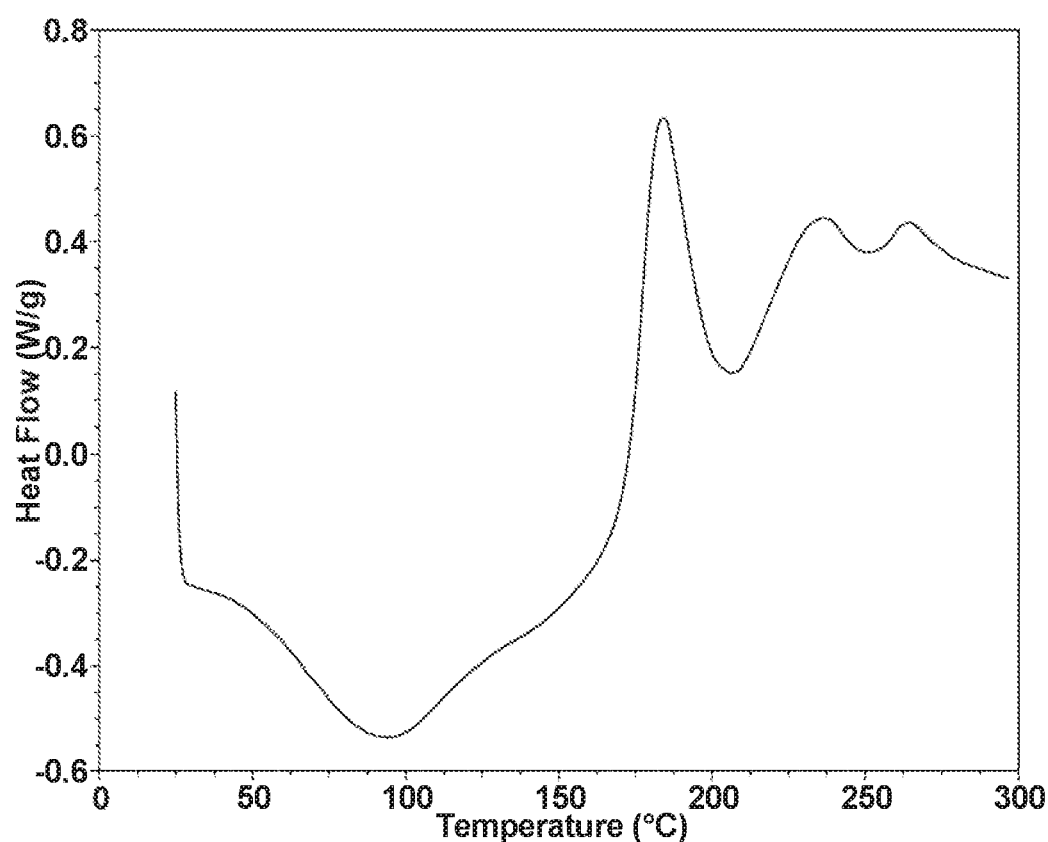
FIG. 7 is a DSC Analysis of Mono MSA Salt Form II of the compound of Example 2.

A DSC analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II, conducted as described above, is seen in FIG. 7.

Figure 8:
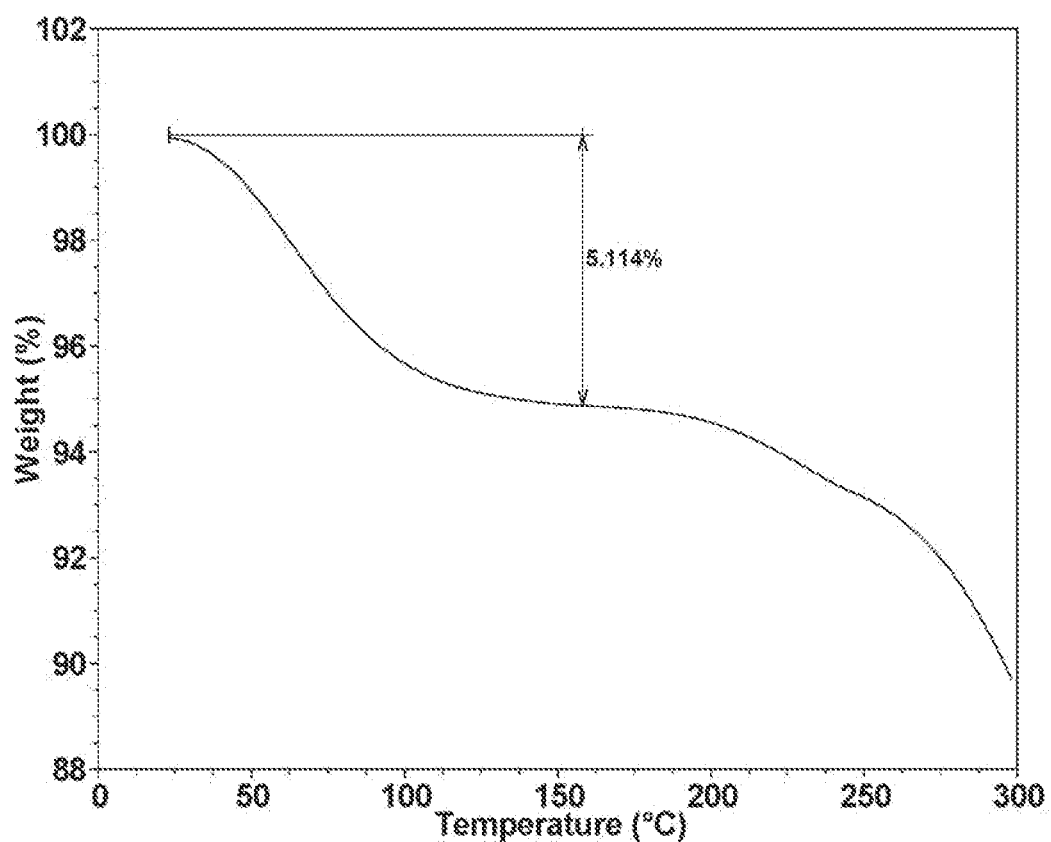
FIG. 8 is a TGA Analysis of Mono MSA Salt Form II of the compound of Example 2.

A TGA analysis of 6-(6-aminopyrazin-2-yl)-N-(4-(4-(oxetan-3-yl)piperazin-1-yl)phenyl)imidazo[1,2-a]pyrazin-8-amine Mono MSA Salt Form II, conducted as described above, is seen in FIG. 8.

Example 10—6-(6-aminopyrazin-2-yl)-N-(4-(4-(oxetan-3-yl)piperazin-1-yl)phenyl)imidazo[1,2-a]pyrazin-8-amine succinate Form I 6-(6-aminopyrazin-2-yl)-N-(4-(4-(oxetan-3-yl)piperazin-1-yl)phenyl)imidazo[1,2-a]pyrazin-8-amine Succinate Form I was prepared by first dissolving 1.6 mol. eq. of succinic acid in THF, and then charging the acidic solution to 6-(6-aminopyrazin-2-yl)-N-(4-(4-(oxetan-3-yl)piperazin-1-yl)phenyl)imidazo[1,2-a]pyrazin-8-amine. The material was then stirred at room temperature with a magnetic stir bar overnight.

Figure 9:
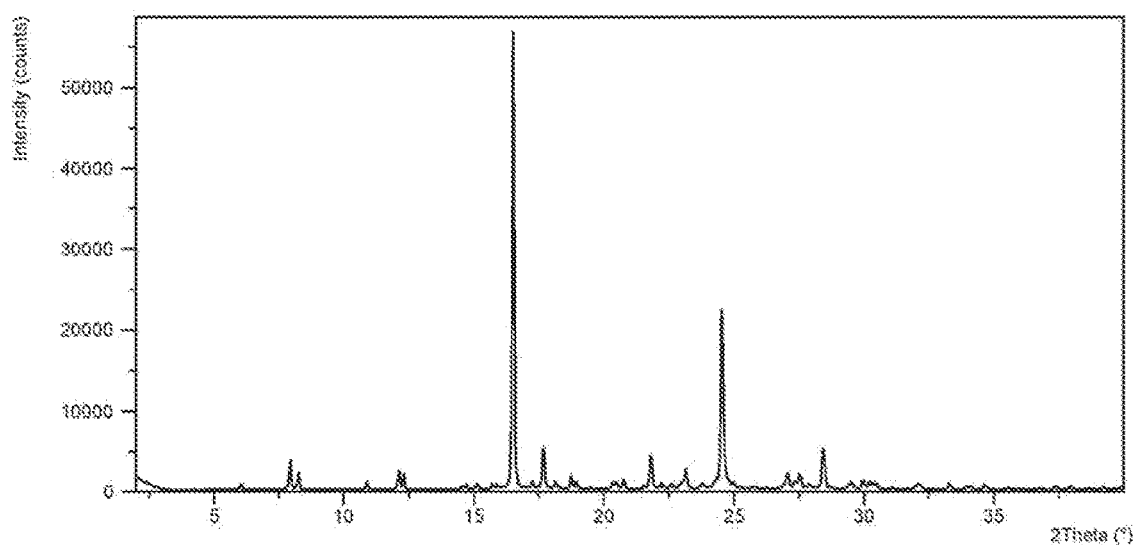
FIG. 9 is an XRPD Analysis of Succinate Form I of the compound of Example 2.

XRPD analysis of 6-(6-aminopyrazin-2-yl)-N-(4-(4-(oxetan-3-yl)piperazin-1-yl)phenyl)imidazo[1,2-a]pyrazin-8-amine succinate Form I was conducted as described above and provided the diffraction pattern seen in FIG. 9, with the peaks in the table below.

| No. | Pos. [°2Th.] | Rel. Int. [%] |
|---|---|---|
| 1 | 16.5 | 100 |
| 2 | 24.5 | 38.64 |
| 3 | 17.7 | 9.27 |
| 4 | 28.4 | 8.68 |
| 5 | 21.8 | 7.57 |
| 6 | 8.0 | 6.53 |
| 7 | 23.1 | 4.59 |
| 8 | 12.1 | 4.38 |
| 9 | 8.3 | 3.78 |
| 10 | 27.1 | 3.65 |

In one embodiment 6-(6-aminopyrazin-2-yl)-N-(4-(4-(oxetan-3-yl)piperazin-1-yl)phenyl)imidazo[1,2-a]pyrazin-8-amine Succinate Form I may be characterized by XRPD peaks 16.5, 24.5, 17.7, 28.4, and 21.8. In another embodiment 6-(6-aminopyrazin-2-yl)-N-(4-(4-(oxetan-3-yl)piperazin-1-yl)phenyl)imidazo[1,2-a]pyrazin-8-amine Succinate Form I may be characterized by XRPD peaks 16.5, 24.5, 8.0 and 8.3.

Figure 10:
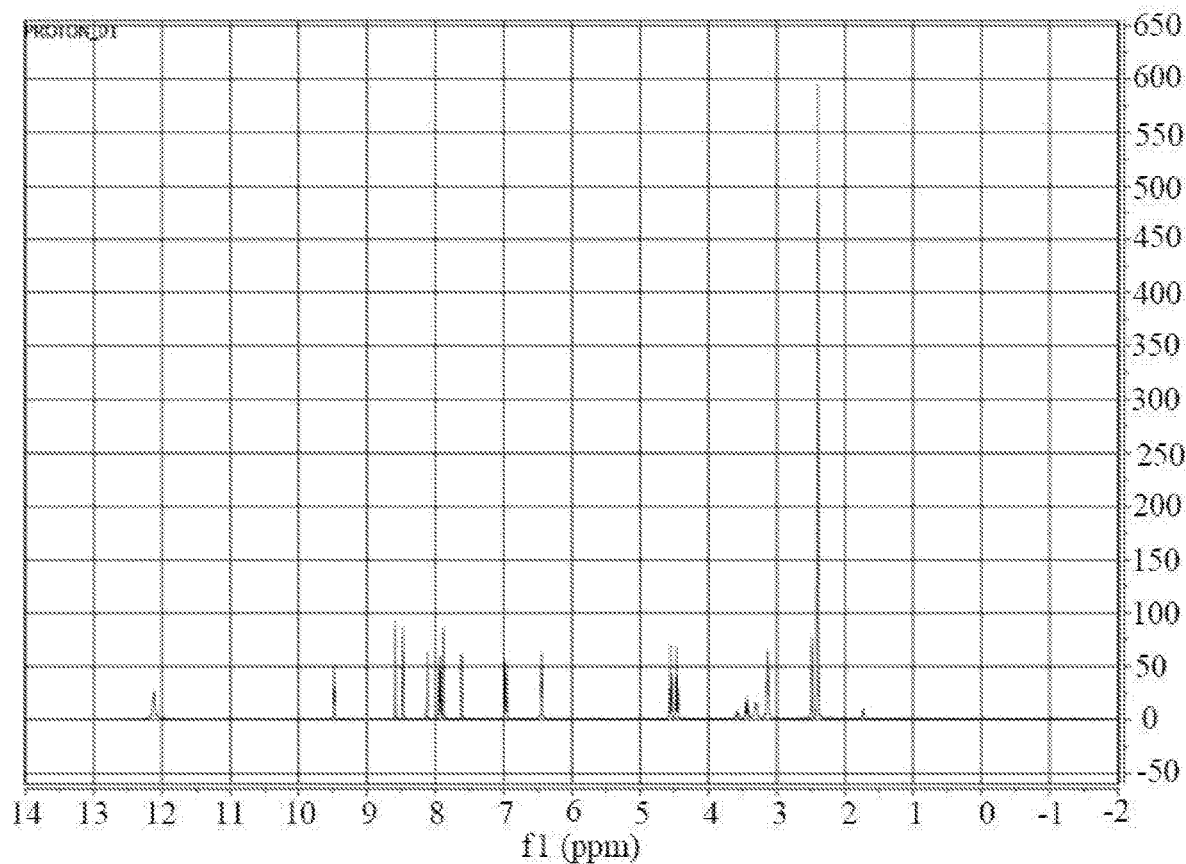
FIG. 10 is an NMR Analysis of Succinate Form I of the compound of Example 2.

NMR Analysis of 6-(6-aminopyrazin-2-yl)-N-(4-(4-(oxetan-3-yl)piperazin-1-yl)phenyl)imidazo[1,2-a]pyrazin-8-amine Succinate Form I, conducted as described above, provided the NMR spectrum seen in FIG. 10.

$^1$H NMR (400 MHz, DMSO-d$_6$) δ 12.12 (s, 2H), 9.48 (s, 1H), 8.59 (s, 1H), 8.48 (s, 1H), 8.12 (d, J=1.1 Hz, 1H), 7.97-7.86 (m, 3H), 7.62 (d, J=1.1 Hz, 1H), 7.01-6.94 (m, 2H), 6.45 (s, 2H), 4.55 (t, J=6.5 Hz, 2H), 4.46 (t, J=6.1 Hz, 2H), 3.49-3.38 (m, 1H), 3.13 (t, J=4.9 Hz, 4H), 2.40 (s, 10H).

Figure 11:
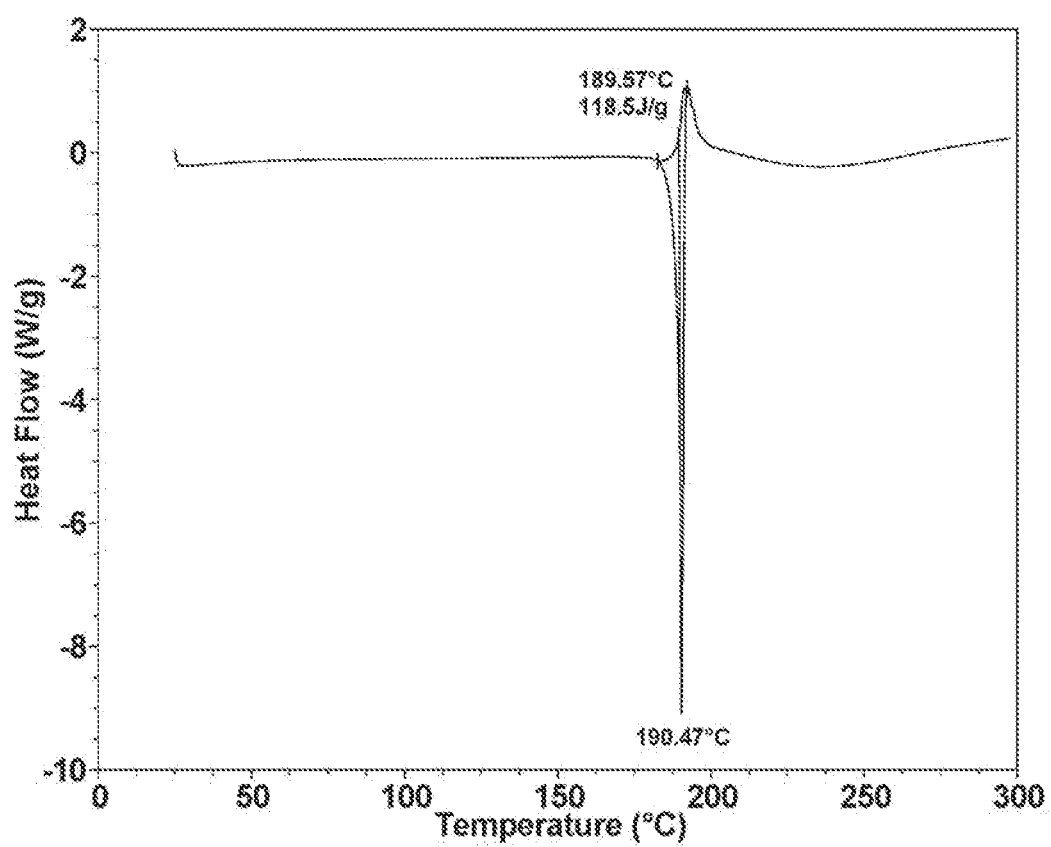
FIG. 11 is a DSC Analysis of Succinate Form I of the compound of Example 2.

A DSC analysis of 6-(6-aminopyrazin-2-yl)-N-(4-(4-(oxetan-3-yl)piperazin-1-yl)phenyl)imidazo[1,2-a]pyrazin-8-amine Succinate Form I, conducted as described above, is seen in FIG. 11.

Figure 12:
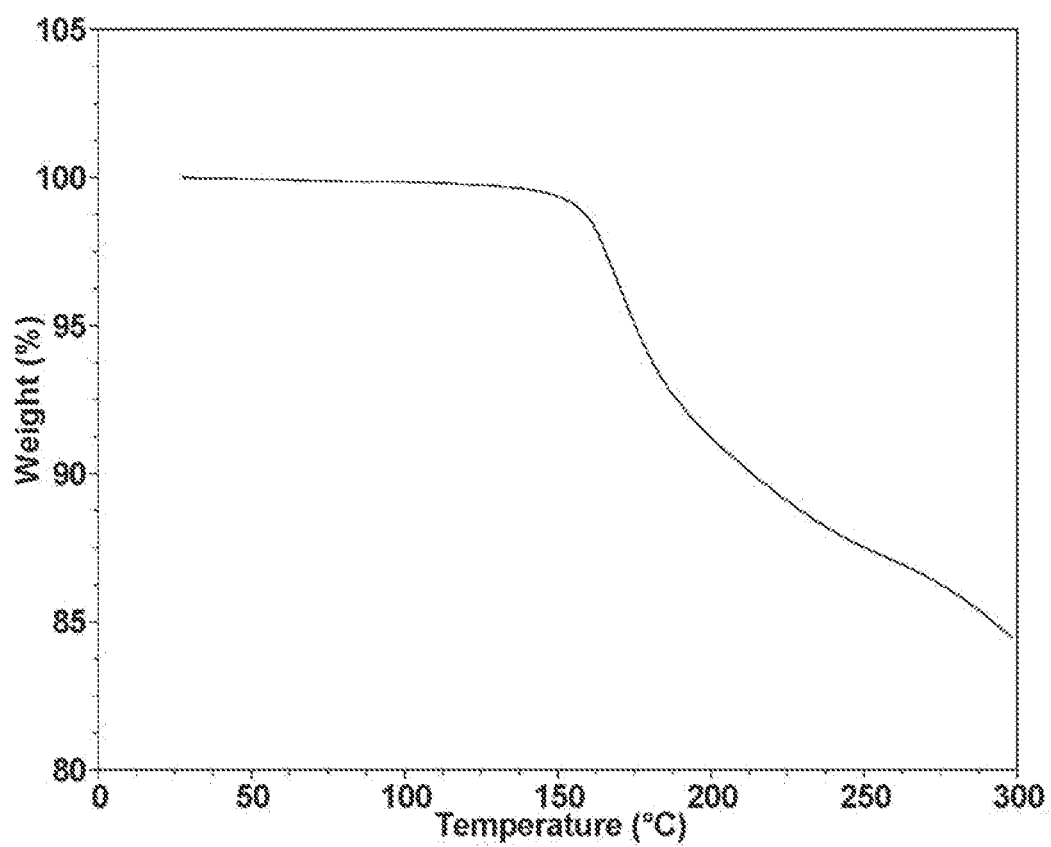
FIG. 12 is a TGA Analysis of Succinate Form I of the compound of Example 2.

A TGA analysis of 6-(6-aminopyrazin-2-yl)-N-(4-(4-(oxetan-3-yl)piperazin-1-yl)phenyl)imidazo[1,2-a]pyrazin-8-amine Succinate Form I, conducted as described above, is seen in FIG. 12.

The process for preparing 6-(6-aminopyrazin-2-yl)-N-(4-(4-(oxetan-3-yl)piperazin-1-yl)phenyl)imidazo[1,2-a]pyrazin-8-amine succinate Form I was also repeated using IPA, Acetone, and 2-MeTHF as solvents.

Example 11—6-(6-aminopyrazin-2-yl)-N-(4-(4-(oxetan-3-yl)piperazin-1-yl)phenyl)imidazo[1,2-a]pyrazin-8-amine succinate Form II 6-(6-aminopyrazin-2-yl)-N-(4-(4-(oxetan-3-yl)piperazin-1-yl)phenyl)imidazo[1,2-a]pyrazin-8-amine free base was charged with 10.0 parts 2-propanol, followed by rapid agitation, to form a slurry. A separate solution of succinic acid (0.43 parts, 1.6 mol eq.) in 2-propanol (15 parts) was prepared at ambient temperature and was added to the slurry. The resulting slurry was then agitated at ambient temperature for about 1 day Another solution of succinic acid (0.09 parts, 0.3 mol eq.) in 2-propanol (3 parts) was added to the slurry and the resulting slurry was agitated at ambient temperature for about two days. An additional solution of succinic acid (0.27 parts, 1.0 mol eq.) in 2-propanol (8 parts) was prepared at ambient temperature and added to the slurry and the resulting slurry was agitated for about 2 days. Then the content temperature was adjusted to 40° C. and the slurry was agitated for about two hours. The content was then returned to ambient temperature and agitated for about 16 hours. The resulting slurry was then filtered, rinsed with 2-propanol (7.0 parts), and dried at 60° C.

Figure 13:
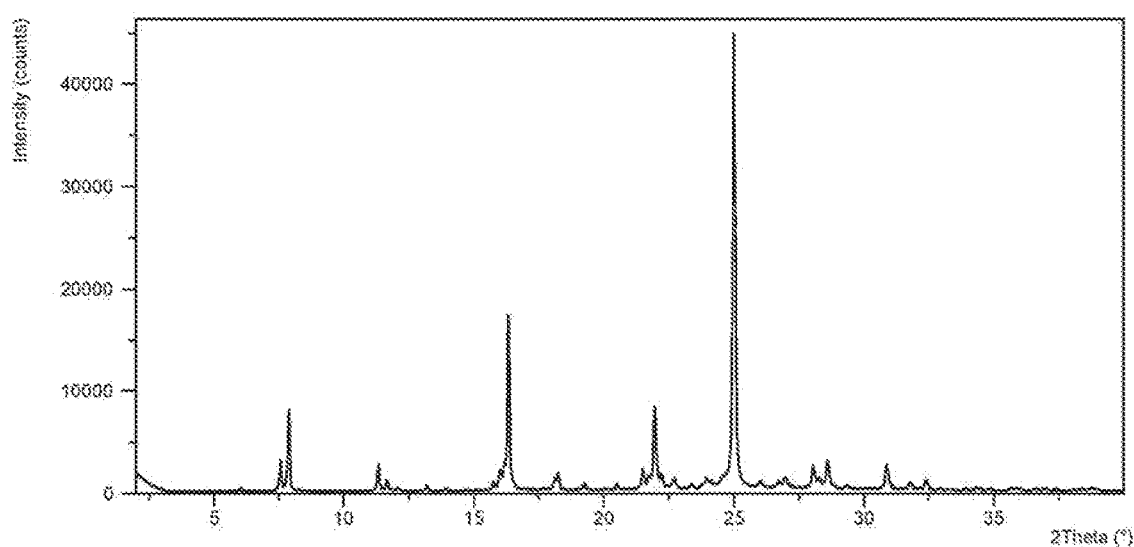
FIG. 13 is an XRPD Analysis of Succinate Form II of the compound of Example 2.

XRPD analysis of 6-(6-aminopyrazin-2-yl)-N-(4-(4-(oxetan-3-yl)piperazin-1-yl)phenyl)imidazo[1,2-a]pyrazin-8-amine succinate Form II was conducted as described above and provided the diffraction pattern seen in FIG. 13, with the peaks in the table below.

| No. | Pos. [°2Th.] | Rel. Int. [%] |
|---|---|---|
| 1 | 24.9821 | 100 |
| 2 | 16.3186 | 38.39 |
| 3 | 21.952 | 18.44 |
| 4 | 7.8958 | 17.62 |
| 5 | 7.5828 | 6.9 |
| 6 | 28.5998 | 6.52 |
| 7 | 11.3329 | 5.73 |
| 8 | 30.8568 | 5.48 |
| 9 | 28.0273 | 5.21 |
| 10 | 21.5026 | 4.73 |

In one embodiment 6-(6-aminopyrazin-2-yl)-N-(4-(4-(oxetan-3-yl)piperazin-1-yl)phenyl)imidazo[1,2-a]pyrazin-8-amine Succinate Form II may be characterized by XRPD peaks 25.0 (24.9821), 16.3 (16.3186), 22.0 (21.952), 7.9 (7.8958), and 7.6 (7.5828). In a further embodiment 6-(6-aminopyrazin-2-yl)-N-(4-(4-(oxetan-3-yl)piperazin-1-yl)phenyl)imidazo[1,2-a]pyrazin-8-amine Succinate Form II may be characterized by XRPD peaks 25.0 (24.9821), 16.3 (16.3186), 7.9 (7.8958), and 7.6 (7.5828).

Figure 14:
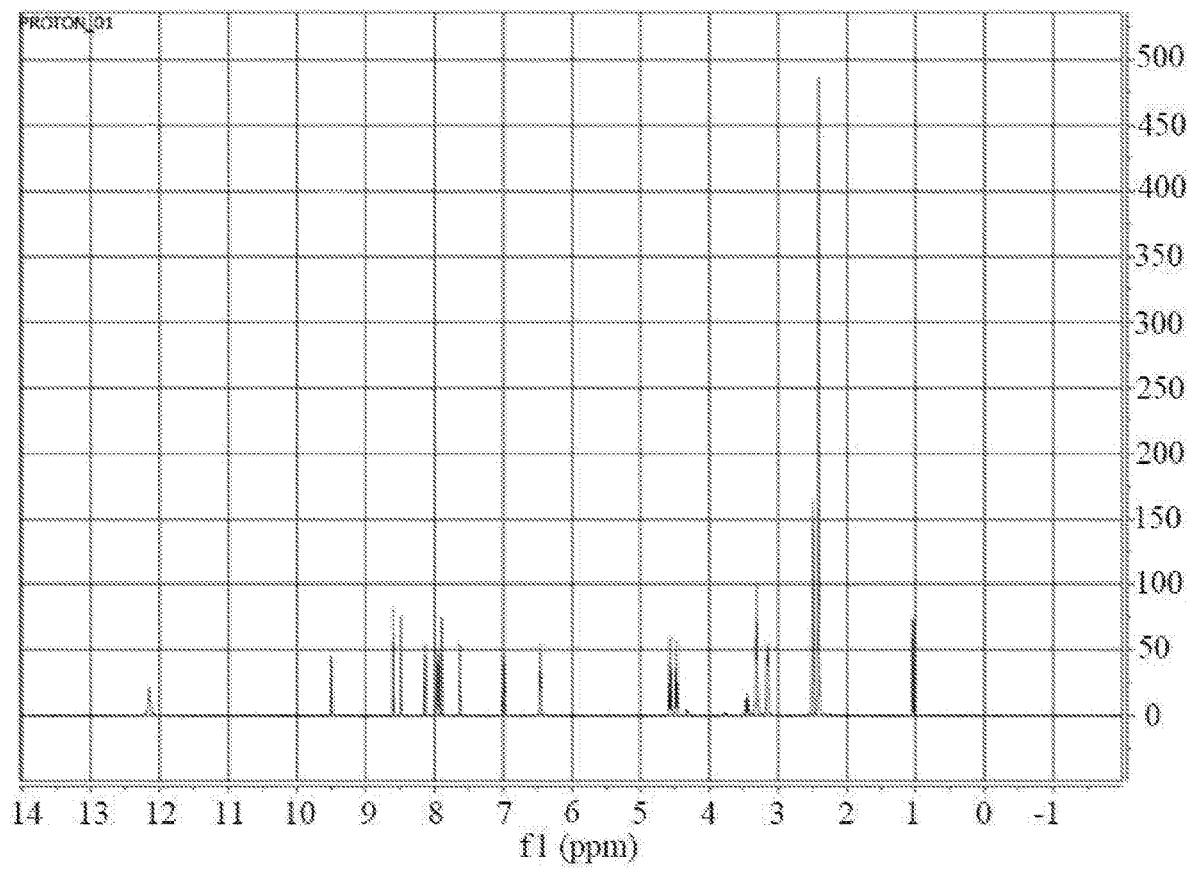
FIG. 14 is an NMR Analysis of Succinate Form II of the compound of Example 2.

NMR Analysis of 6-(6-aminopyrazin-2-yl)-N-(4-(4-(oxetan-3-yl)piperazin-1-yl)phenyl)imidazo[1,2-a]pyrazin-8-amine Succinate Form II, conducted as described above, provided the NMR spectrum seen in FIG. 14.

$^1$H NMR (400 MHz, DMSO-d$_6$) δ 12.13 (s, 2H), 9.48 (s, 1H), 8.58 (s, 1H), 8.47z (s, 1H), 8.12 (d, J=1.1 Hz, 1H), 7.97-7.86 (m, 3H), 7.62 (d, J=1.1 Hz, 1H), 7.02-6.94 (m, 2H), 6.45 (s, 2H), 4.55 (t, J=6.5 Hz, 2H), 4.46 (t, J=6.0 Hz, 2H), 3.44 (p, J=6.3 Hz, 1H), 3.17-3.10 (m, 4H), 2.40 (s, 10H), 1.02 (d, J=6.1 Hz, 2H).

Figure 15:
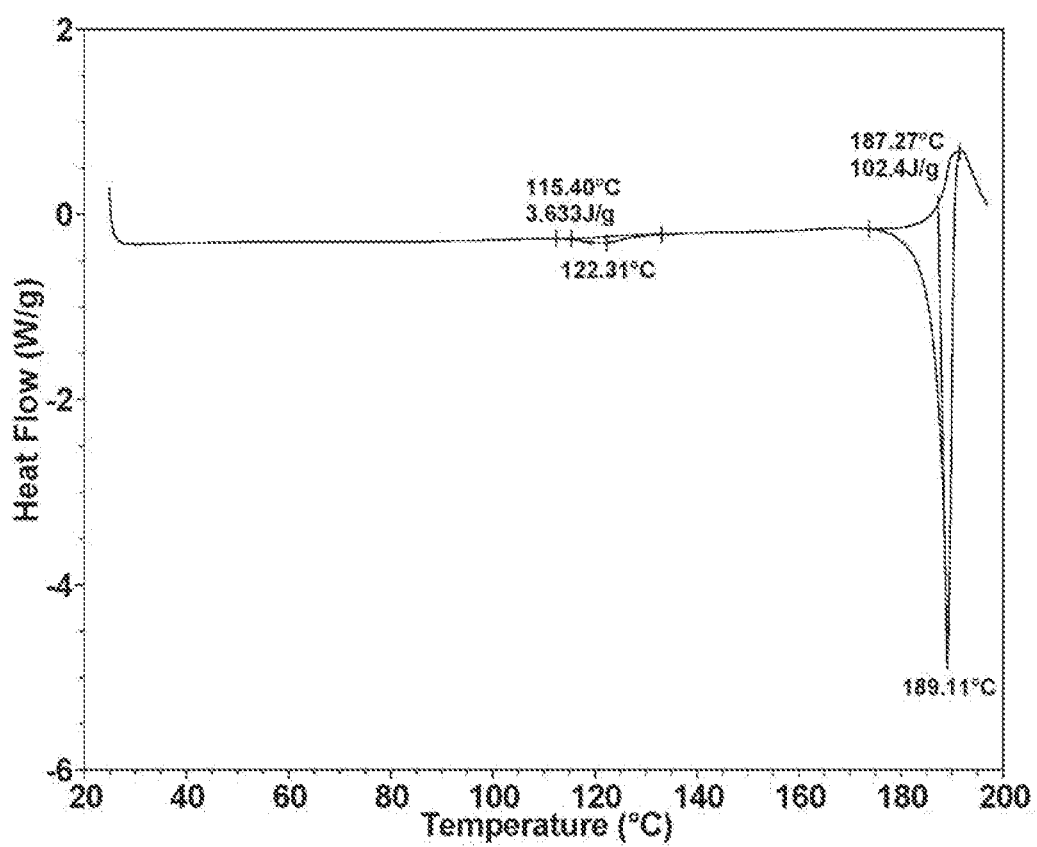
FIG. 15 is a DSC Analysis of Succinate Form II of the compound of Example 2.

A DSC analysis of 6-(6-aminopyrazin-2-yl)-N-(4-(4-(oxetan-3-yl)piperazin-1-yl)phenyl)imidazo[1,2-a]pyrazin-8-amine Succinate Form II, conducted as described above, is seen in FIG. 15.

Figure 16:
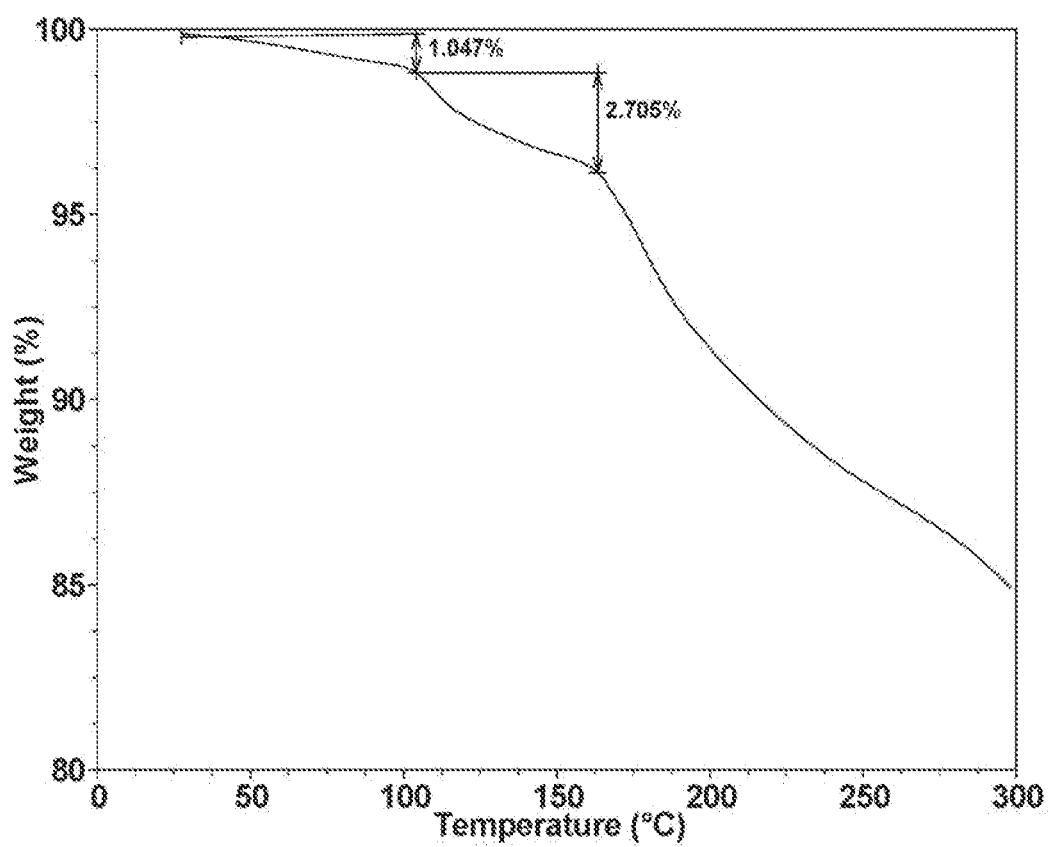
FIG. 16 is a TGA Analysis of Succinate Form II of the compound of Example 2.

A TGA analysis of 6-(6-aminopyrazin-2-yl)-N-(4-(4-(oxetan-3-yl)piperazin-1-yl)phenyl)imidazo[1,2-a]pyrazin-8-amine Succinate Form II, conducted as described above, is seen in FIG. 16.

BIOLOGICAL EXAMPLES

Example 12: High Throughput Syk Biochemical Assay

Syk activity was measured using KinEASE (Cisbio), a time-resolved fluorescence resonance energy transfer (TR-FRET) immunoassay. In this assay, Syk-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. In brief, test compounds serially diluted in DMSO were delivered into Corning white, low volume, non-binding 384 well plates using the Echo 550 acoustic liquid dispenser (Labcyte®). Syk enzyme and substrates were dispensed into assay plates using a Multi-Flo (Bio-Tek Instruments). The standard 5 μL reaction mixture contained 20 μM ATP, 1 μM biotinylated peptide, 0.015 nM of Syk in reaction buffer (50 mM Hepes, pH 7.0, 0.02% NaN$_3$, 0.1% BSA, 0.1 mM Orthovanadate, 5 mM MgCl$_2$, 1 mM DTT, 0.025% NP-40). After 30 minutes of incubation at room temperature, 5 μL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows: % Inhibition=100×(Ratio$_{Sample}$−Ratio$_{0\%Inhibition}$)/(Ratio$_{100\% Inhibition}$−Ratio$_{0\% Inhibition}$) where 0.1% DMSO (0% inhibition) was the negative control and 1 µM K252a (100% inhibition) was used as the positive control. Activity of the compounds of Examples 1-7 are provided in the following table, demonstrating the compounds are Syk inhibitors with IC$_{50}$ below 50 nM.

| Example No.: Compound Name | Syk IC$_{50}$ (nM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 6.2 |
| Ex.-2: 6-(6-aminopyrazin-2-yl)-N-(4-(4-(oxetan-3-yl)piperazin-1-yl)phenyl)imidazo[1,2-a]pyrazin-8-amine | 13.5 |
| Ex.-3: (R)-(4-(4-((6-(6-aminopyrazin-2-yl)imidazo[1,2-a]pyrazin-8-yl)amino)phenyl)morpholin-2-yl)methanol | 13.3 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 44 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 12.2 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 14.5 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 8.7 |

Example 13: 384-well HTBS Whole Blood CD63 Basophil Assay

Syk activity was assessed in relation to reduced activation of basophils as measured by the expression of CD63 in a human whole blood basophil cellular assay (25% blood). Basophil activation was measured in human whole blood using the Flow CAST kit (Buhlmann Laboratories AG, Baselstrasse, Switzerland) following the protocol provided by the manufacturer with minor modifications. Fresh human whole blood in heparin was collected and delivered same day (AllCells, Emeryville, CA). Whole blood samples were incubated with either DMSO (1% final) or serial diluted compounds in DMSO for 60 minutes at 37° C. Basophils were activated using the anti-FceRI mAb and stained with anti-CD63-FITC and anti-CCR3-PE for 20 minutes at 37° C. (per well: 50 µL of whole blood was mixed with 113 µL of stimulation buffer, 8.5 µL anti-FceRI mAb, 8.5 µL Ab stain CCR3-PE/CD63-FITC). Cells were centrifuged at 1000×g for 18 minutes and 150 µL/well of supernatant removed. Red blood cells were lysed and cells fixed by 2 rounds of cell lysing: resuspending cell pellets with 150 µL/well 1× lysis buffer, incubating at room temperature for 10 minutes, and collecting cell pellets by centrifuging for 1200 rpms for 5 minutes. Cells were washed with 150 µL/well wash buffer twice, and resuspended in a final volume of 75 µL/well of wash buffer for either immediate flow cytometry analysis or overnight incubation at 4° C. followed by flow cytometry analysis. Degranulation (basophil activation) was detected by CD63 surface expression on CCR3 positive cells. The percent CD63 positive cells within the gated basophil population were determined and normalized to the DMSO (negative control) and control compound (positive control). Activity of the compounds of Examples 1-7 are provided in the following table, demonstrating the compounds are effective in reducing the activation of basophils, with EC$_{50}$ below 200 nM.

| Example No.: Compound Name | CD63 EC$_{50}$ (nM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 51 |
| Ex.-2: 6-(6-aminopyrazin-2-yl)-N-(4-(4-(oxetan-3-yl)piperazin-1-yl)phenyl)imidazo[1,2-a]pyrazin-8-amine | 80 |
| Ex.-3: (R)-(4-(4-((6-(6-aminopyrazin-2-yl)imidazo[1,2-a]pyrazin-8-yl)amino)phenyl)morpholin-2-yl)methanol | 63 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 157 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 120 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 128 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 167 |

Example 14: Kinetic Solubility

The kinetic solubility of compounds in phosphate buffer at pH 7.4 was assessed. The compounds to be tested were dissolved in dimethylsulfoxide at a 10 mM concentration. Stock samples were diluted, 3 µl with 297 µl of the phosphate buffer at pH 7.4 (DulBecco's phosphate buffered saline (Sigma-Aldrich D8662), overall molarity is 0.149M and pH 7.43). The samples were then incubated for 24 hours at 37° C. with shaking, the centrifuged and an aliquot taken and tested relative to a known standard concentration of 0.1 mM. The kinetic solubility of the compounds of Examples 1-7 are provided in the following table, demonstrating the compounds have kinetic solubility at pH 7.4 of greater than 90 µM.

| Example No.: Compound Name | Solubility pH 7.4 (µM) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 95 |
| Ex.-2: 6-(6-aminopyrazin-2-yl)-N-(4-(4-(oxetan-3-yl)piperazin-1-yl)phenyl)imidazo[1,2-a]pyrazin-8-amine | 95 |
| Ex.-3: (R)-(4-(4-((6-(6-aminopyrazin-2-yl)imidazo[1,2-a]pyrazin-8-yl)amino)phenyl)morpholin-2-yl)methanol | 91 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 100 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 97 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 99 |

Example 15: Human Hepatocyte Stability Assay

The human hematocyte stability of the compounds as predicted hepatocyte clearance in L/hr/kg was assessed. Compounds to be tested were diluted to 200 µM (4 µl of 10 mM DMSO stock into 196 µl ACN:H$_2$O (50:50). Propranolol was used as a positive control, and buffer only without hepatocytes as 0% control. These were further diluted 4 µl with 891 µl KHB buffer (InVitroGRO catalog number Z99074) to provide 2× dosing solution. To each well of 24 well plate, 250 µl of the 2× dosing solution was added to each well with 250 µl of hepatocytes cells (1×10$^6$ viable cells/ml per well) or KHB for control samples to achieve a final compound concentration of 1 µM during incubation. The final solvent concentration was 0.01% DMSO and 0.25% ACN. The culture plate was placed on a rocker and incubated at 37° C., 5% $CO_2$. Samples were collected at time 0, 1, 3, and 6 hours. The loss of parent compound was determined using LC-MS methods against a standard curve. Activity of the compounds of Examples 1-7 are provided in the following table, showing hepatocyte clearance of about 0.12 L/hr/kg or less.

| Example No.: Compound Name | Hheps CL (L/hr/kg) |
|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 0.12 |
| Ex.-2: 6-(6-aminopyrazin-2-yl)-N-(4-(4-(oxetan-3-yl)piperazin-1-yl)phenyl)imidazo[1,2-a]pyrazin-8-amine | 0.055 |
| Ex.-3: (R)-(4-(4-((6-(6-aminopyrazin-2-yl)imidazo[1,2-a]pyrazin-8-yl)amino)phenyl)morpholin-2-yl)methanol | 0.09 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 0.08 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 0.07 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 0.08 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 0.05 |

Example 16: Comparison to Known Syk Inhibitors

The assays of Examples 8-11 were used to compare the compounds as described herein with compounds known in the art. The data comparing the compounds of Examples 1-7 to previously described compounds is provided in the following table. From these results, it is clear that compounds as described herein are desirable as Syk inhibitors, with improved Syk and CD63 activity relative to the known compounds, improved kinetic solubility (at least about 9-fold more soluble) and hepatocyte clearance (at least about 2-fold less clearance). As such, the combination of improved Syk and CD63 inhibitory activity with improved kinetic solubility and clearance provides compounds that are expected to be effective at treating diseases as described herein with improved pharmacokinetic properties.

| Compound Name | Syk $IC_{50}$ (nM) | CD63 $IC_{50}$ (nM) | Solubility pH 7.4 (µM) | Hheps CL (units) |
|---|---|---|---|---|
| Ex.-1: 6-(6-amino-5-methylpyrazin-2-yl)-N-(4-(4-(oxetan-3-yl)piperazin-1-yl)phenyl)imidazo[1,2-a]pyrazin-8-amine | 6.2 | 51 | 95 | 0.12 |
| Ex.-2: 6-(6-aminopyrazin-2-yl)-N-(4-(4-(oxetan-3-yl)piperazin-1-yl)phenyl)imidazo[1,2-a]pyrazin-8-amine | 13.5 | 80 | 95 | 0.055 |
| Ex.-3: (R)-(4-(4-((6-(6-aminopyrazin-2-yl)imidazo[1,2-a]pyrazin-8-yl)amino)phenyl)morpholin-2-yl)methanol | 13.3 | 63 | 91 | 0.09 |
| Ex.-4: 6-(6-aminopyrazin-2-yl)-5-methyl-N-(4-(4-(oxetan-3-yl)piperazin-1-yl)phenyl)imidazo[1,2-a]pyrazin-8-amine | 44 | 157 | 100 | 0.08 |
| Ex.-5: 2-(5-((6-(6-aminopyrazin-2-yl)imidazo[1,2-a]pyrazin-8-yl)amino)-2-(4-(oxetan-3-yl)piperazin-1-yl)phenoxy)ethanol | 12.2 | 120 | 97 | 0.07 |
| Ex.-6: 2-((4-(4-((6-(6-aminopyrazin-2-yl)imidazo[1,2-a]pyrazin-8-yl)amino)phenyl)piperazin-1-yl)methyl)propane-1,3-diol | 14.5 | 128 | 99 | 0.08 |
| Ex.-7: 2-(5-((6-(6-amino-5-methylpyrazin-2-yl)imidazo[1,2-a]pyrazin-8-yl)amino)-2-(4-(oxetan-3-yl)piperazin-1-yl)phenoxy)ethanol | 8.7 | 167 | nd | 0.05 |
| Known compounds: | | | | |
| 6-(5-aminopyridin-3-yl)-N-(4-morpholinophenyl)imidazo[1,2-a]pyrazin-8-amine | 31 | 101 | 5 | 0.68 |
| 6-(3-aminophenyl)-N-(3,4-dimethoxyphenyl)imidazo[1,2-a]pyrazin-8-amine | 188 | 809 | 3 | 0.24 |
| 6-(5-amino-6-methylpyridin-3-yl)-N-(4-morpholinophenyl)imidazo[1,2-a]pyrazin-8-amine | 16 | 250 | 5 | 0.80 |
| 6-(6-aminopyridin-3-yl)-N-(3,4-dimethoxyphenyl)imidazo[1,2-a]pyrazin-8-amine | 53 | 734 | 10 | 0.90 |

Throughout this specification, various patents, patent applications and other types of publications (e.g., journal articles) are referenced. The disclosure of all patents, patent applications, and publications cited herein are hereby incorporated by reference in their entirety for all purposes.

What is claimed:

1. A crystalline form of a succinate salt of Compound 2:

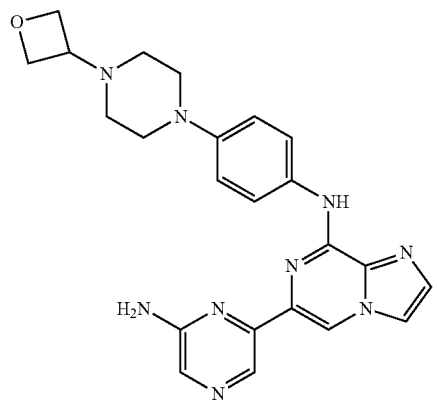

2 wherein the crystalline form is succinate Form II; and
wherein crystalline succinate Form II is characterized by an X-ray powder diffractogram comprising characteristic peaks (° 2θ) at 7.6°±0.2° 2θ, 7.9°±0.2° 2θ, 16.3°±0.2° 2θ, 22.0°±0.2° 2θ, and 25.0°±0.2 °2θ.

2. The crystalline form of claim 1, wherein the crystalline form is further characterized by an X-ray powder diffractogram comprising additional characteristic peaks (° 2θ) at 11.3°±0.2° 2θ and 28.6°±0.2° 2θ.

3. A pharmaceutical composition comprising the crystalline form of claim 1 and at least one pharmaceutically acceptable vehicle.

4. A method for inhibiting spleen tyrosine kinase activity in a subject, wherein the method comprises administering to the subject in need thereof an effective amount of the crystalline form of claim 1.

5. The method of claim 4, wherein the subject suffers from a disorder or disease selected from the group consisting of acute disseminated encephalomyelitis, acute hypersensitivity, acute respiratory distress syndrome, Addison's disease, allergic conjunctivitis, allergic rhinitis, allograft rejection, alveolitis, Alzheimer's disease, appendicitis, asthma, atherosclerosis, atopic dermatitis, autoimmune hemolytic anemia, autoimmune thyroiditis, Behcet's disease, brain injury due to minor trauma, bronchiectasis, cholocystitis, chronic bronchitis, chronic idiopathic thrombocytopenic purpura, chronic inflammatory bowel disease, contact dermatitis, coryza, Crohn's disease, cystic fibrosis, cytokine-induced toxicity, delayed hypersensitivity, dermatomyositis, diabetes, a disease involving leukocyte diapedesis, a disease state due to leukocyte dyscrasia, a disease state due to leukocyte metastasis, eczema, emphysema, encephalitis, endotoxic shock, enteritis, eosinophilic granuloma, essential thrombocythemia, fever due to infection, a food allergy, gastritis, gingivitis, glomerulonephritis, Goodpasture's syndrome, gouty arthritis, graft-versus-host disease, a granulocyte transfusion-associated syndrome, hay fever, a hemorrhage, hepatitis, hyperacute rejection of transplanted organs, hypovolemic shock, inflammatory pelvic disease, irritable bowel syndrome, keloid formation, meningitis, monoarticular arthritis, multiple organ injury syndrome secondary to septicemia, multiple sclerosis, myalgia due to infection, myasthenia gravis, myocarditis, myositis, necrotizing enterocolitis, nephritis, osteoarthritis, osteomyelitis, pancreatitis, Parkinson's disease, pleurisy, pneumonia, pneumonitis, polycystic kidney disease, polycythemia vera, psoriasis, psoriatic arthritis, pulmonary oxygen toxicity, pulmonary sarcoidosis, reperfusion injury of the brain, reperfusion injury of the extremities, reperfusion injury of the myocardium, Reynaud's syndrome, rheumatoid arthritis, scar tissue formation, scleroderma, sepsis, septic shock, silicosis, sinusitis, Sjögren's syndrome, skin sunburn, spinal cord injury due to minor trauma, spondylitis, systemic lupus erythematosus, thermal injury, thyroid-associated ophthalmopathy, tissue graft rejection, toxic shock syndrome, trauma, ulcerative colitis, urethritis, urticaria, uveitis, vasculitis, and vernal conjunctivitis.

6. The method of claim 5, wherein the asthma, diabetes, hemorrhage, hepatitis, pneumonia, or sepsis is selected from the group consisting of bronchial asthma, type I diabetes mellitus, pulmonary hemorrhage, alcoholic hepatitis, bacterial pneumonia, gram negative sepsis, and gram positive sepsis.

7. The method of claim 4, wherein:
(a) the subject suffers from a solid tumor; and
(b) the solid tumor is due to a cancer selected from the group consisting of an adrenocorticotropic hormone (ACTH)-producing tumor, bladder cancer, bone cancer, a brain tumor, breast cancer, a cancer of the adrenal cortex, central nervous system cancer, cervical cancer, colon cancer, colorectal cancer, endometrial cancer, esophageal cancer, gall bladder cancer, gastric cancer, head and neck cancer, hemangiopericytoma, hepatocellular cancer, Kaposi's sarcoma, lung cancer, malignant pleural effusion, melanoma, mesothelioma, myxoid carcinoma, neuroblastoma, neuroendocrine cancer, oral carcinoma, ovarian cancer, pancreatic cancer, peritoneal effusion, prostate cancer, renal cancer, retinoblastoma, round cell carcinoma, soft tissue sarcoma, squamous cell carcinoma, thyroid cancer, a trophoblastic neoplasm, urological cancer, and Wilms tumor.

8. The method of claim 7, wherein the brain tumor is selected from the group consisting of adult anaplastic astrocytoma, adult glioblastoma multiforme, anaplastic oligodendroglioma, and a glioma.

9. The method of claim 7, wherein the lung cancer is selected from the group consisting of non-small cell lung cancer and small cell lung cancer.

10. The method of claim 7, wherein the squamous cell carcinoma is esophageal squamous cell carcinoma.

11. The method of claim 4, wherein the subject suffers from a disorder or disease selected from the group consisting of acute lymphocytic leukemia, acute myeloid leukemia, anaplastic large cell lymphoma, angioimmunoblastic T-cell lymphoma, B-cell acute lymphoblastic leukemia, B-cell lymphoma, B-cell prolymphocytic leukemia, Burkitt's lymphoma, chronic lymphocytic leukemia, chronic myeloid leukemia, cutaneous T-cell lymphoma, extranodal T-cell lymphoma, follicular lymphoma, hairy cell leukemia, immunoblastic large cell lymphoma, juvenile myelomonocytic leukemia, lymphoblastic lymphoma, lymphoplasmacytic lymphoma, mantle cell lymphoma, marginal zone lymphoma, minimal residual disease, multiple myeloma, myelodysplastic syndrome, a myeloproliferative disease, nodal marginal zone lymphoma (+/−monocytoid B-cells), non-Hodgkin's lymphoma, plasmacytoma, primary effusion lymphoma, primary myelofibrosis, secondary myelofibrosis, small lymphocytic lymphoma, small non-cleaved cell lymphoma, T-cell acute lymphoblastic leukemia, and Waldestrom's macroglobulinemia.

12. The method of claim 11, wherein the B-cell lymphoma, cutaneous T-cell lymphoma, or non-Hodgkin's lymphoma is selected from the group consisting of diffuse large B-cell lymphoma, extranodal marginal zone B-cell lymphoma of mucosa-associated lymphoid tissue type, intravascular large B-cell lymphoma, mediastinal large B-cell lymphoma, splenic marginal zone B-cell lymphoma (+/−villous lymphocytes), mycosis fungoides, and indolent non-Hodgkin's lymphoma.

13. The method of claim 12, wherein the indolent non-Hodgkin's lymphoma is refractory indolent non-Hodgkin's lymphoma.

14. The method of claim 4, wherein the subject suffers from a disorder or disease selected from the group consisting of acute disseminated encephalomyelitis, asthma, autoimmune hemolytic anemia, chronic obstructive pulmonary disease, Crohn's disease, idiopathic thrombocytopenic purpura, irritable bowel disease, multiple sclerosis, myasthenia gravis, psoriasis, rheumatoid arthritis, Sjögren's syndrome, systemic lupus erythematosus, and ulcerative colitis.

15. The method of claim 4, wherein the subject suffers from a disorder or disease selected from the group consisting of asthma, chronic obstructive pulmonary disease, multiple sclerosis, rheumatoid arthritis, and systemic lupus erythematosus.

16. The method of claim 4, wherein the subject suffers from a disorder or disease selected from the group consisting of an allergic disorder, an autoimmune disease, a cancer, and an inflammatory disorder.

17. The method of claim 4, wherein the subject suffers from a cancer selected from the group consisting of a hematologic malignancy and a solid tumor.

18. The method of claim 4, wherein the subject suffers from a hematologic malignancy selected from the group consisting of leukemia, lymphoma, and multiple myeloma.

19. The method of claim 4, wherein the subject suffers from an inflammatory disorder.

\* \* \* \* \*